US008058418B2

(12) United States Patent
Boyle et al.

(10) Patent No.: US 8,058,418 B2
(45) Date of Patent: Nov. 15, 2011

(54) POLYNUCLEOTIDES ENCODING HEAVY AND LIGHT CHAINS OF ANTIBODIES TO OPGL

(75) Inventors: William J. Boyle, Thousand Oaks, CA (US); Francis H. Martin, Newbury Park, CA (US); Jose R. Corvalan, Foster City, CA (US); C. Geoffrey Davis, Burlingame, CA (US)

(73) Assignees: Amgen Inc., Thousand Oaks, CA (US); Amgen Fremont Inc., Fremont, CA (US)

( * ) Notice: Subject to any disclaimer, the term of this patent is extended or adjusted under 35 U.S.C. 154(b) by 504 days.

(21) Appl. No.: 11/981,664

(22) Filed: Oct. 30, 2007

(65) Prior Publication Data
US 2009/0274688 A1 Nov. 5, 2009

Related U.S. Application Data

(63) Continuation of application No. 10/180,648, filed on Jun. 25, 2002, now Pat. No. 7,364,736.

(60) Provisional application No. 60/301,172, filed on Jun. 26, 2001.

(51) Int. Cl.
*C12N 15/11* (2006.01)

(52) U.S. Cl. ............... 536/23.53; 435/326; 435/328; 435/336; 435/69.6; 424/133.1; 424/141.1; 424/145.1; 530/387.3; 530/388.24

(58) Field of Classification Search .................. None
See application file for complete search history.

(56) References Cited

U.S. PATENT DOCUMENTS

| 4,710,457 | A |   | 12/1987 | Dupont et al. |
|---|---|---|---|---|
| 5,693,762 | A | * | 12/1997 | Queen et al. ............ 530/387.3 |
| 5,886,152 | A |   | 3/1999 | Nakatani et al. |
| 5,891,438 | A |   | 4/1999 | Silverman |
| 6,015,938 | A |   | 1/2000 | Boyle et al. |
| 6,017,729 | A |   | 1/2000 | Anderson et al. |
| 6,242,213 | B1 |   | 6/2001 | Anderson |
| 6,271,349 | B1 |   | 8/2001 | Dougall et al. |
| 6,316,408 | B1 |   | 11/2001 | Boyle |
| 6,419,929 | B1 |   | 7/2002 | Anderson |
| 6,479,635 | B1 |   | 11/2002 | Anderson et al. |
| 6,528,482 | B1 |   | 3/2003 | Anderson et al. |
| 6,537,763 | B2 |   | 3/2003 | Dougall et al. |
| 6,562,948 | B2 |   | 5/2003 | Anderson |
| 6,569,430 | B1 |   | 5/2003 | Waldmann et al. |
| 6,645,500 | B1 |   | 11/2003 | Halkier et al. |
| 6,740,522 | B2 |   | 5/2004 | Anderson |
| 7,097,834 | B1 |   | 8/2006 | Boyle |
| 7,364,736 | B2 |   | 4/2008 | Boyle et al. |
| 7,411,050 | B2 |   | 8/2008 | Anderson |
| 7,449,185 | B2 |   | 11/2008 | Yamaguchi et al. |
| 7,527,790 | B2 |   | 5/2009 | Yamaguchi et al. |
| 7,718,776 | B2 |   | 5/2010 | Boyle et al. |
| 7,744,886 | B2 |   | 6/2010 | Anderson |
| 7,923,008 | B2 |   | 4/2011 | Boyle |
| 2002/0150555 | A1 |   | 10/2002 | Gillispie et al. |
| 2003/0017151 | A1 |   | 1/2003 | Dougall et al. |
| 2003/0021785 | A1 |   | 1/2003 | Dougall |
| 2003/0175840 | A1 |   | 9/2003 | Anderson et al. |
| 2003/0176647 | A1 |   | 9/2003 | Yamaguchi et al. |
| 2003/0208045 | A1 |   | 11/2003 | Yamaguchi et al. |
| 2004/0086503 | A1 | * | 5/2004 | Cohen et al. ............... 424/143.1 |
| 2005/0003457 | A1 |   | 1/2005 | Yamaguchi et al. |

FOREIGN PATENT DOCUMENTS

| AR | 032028 A1 | 10/2003 |
|---|---|---|
| AU | 2002231368 B2 | 7/2002 |
| EP | 0 911 342 A | 4/1999 |
| WO | WO 97/23614 A1 | 7/1997 |
| WO | WO 98/28424 A2 | 7/1998 |
| WO | WO 98/28426 A3 | 7/1998 |
| WO | WO 98/46644 A1 | 10/1998 |
| WO | WO 98/46751 A1 | 10/1998 |
| WO | WO 99/29865 A2 | 6/1999 |
| WO | WO 99/58674 A2 | 11/1999 |
| WO | WO 00/15807 A1 | 3/2000 |
| WO | WO 00/37504 A2 | 6/2000 |
| WO | WO 01/23549 A1 | 4/2001 |
| WO | WO 01/44472 A1 | 6/2001 |
| WO | WO 01/62932 A1 | 8/2001 |
| WO | WO 01/91793 A1 | 12/2001 |
| WO | WO 02/15846 A2 | 2/2002 |
| WO | WO 02/16551 A2 | 2/2002 |
| WO | WO 02/053596 A2 | 7/2002 |

OTHER PUBLICATIONS

Janeway et al., Immunobiology, 3rd edition, 1997, Garland Press, pp. 3:1 to 3:11.*
William E. Paul, M.D. ed., Fundamental Immunology, 3d ed. 1993, p. 242.*
Portolano et al., J. Immunol., 1993, 150:880-887.*
Rudikoff et al., Proc Natl Acad Sci U S A. Mar. 1982;79(6):1979-83.*
Anderson et al., "A homologue of the TNF receptor and its ligand enhance T-cell growth and dendritic-cell function," *Nature*, 390:175-179 (1997).
Body et a., "A Study of the Biological Receptor Activator of Nuclear Factor-κB Ligand Inhibitor, Denosumab, in Patients with Multiple Myeloma or Bone Metastases from Breast Cancer," *Clin. Cancer Res.* 2006, 12(4):1221-1228 (2006).
Hofbauer et al., "The Role of Receptor Activator of Nuclear Factor -κB Ligand and Osteoprotegerin in the Pathogenesis and Treatment of Metabolic Bone Disease," *J. of Clin. Endocrin. Metab.*, 85:2355-2363 (2000).
Kinpara et al., "Osteoclast differentiation factor in human osteosarcoma cell line," *J. Immunoassay*, 21:327-340 (2000).
Kodaira et al., "Cloning and characterization of the gene encoding mouse osteoclast differentiation factor," *Gene*, 230:121-127 (1999).

(Continued)

*Primary Examiner* — Michael Szperka
(74) *Attorney, Agent, or Firm* — Finnegan, Henderson, Farabow, Garrett, and Dunner, LLP

(57) ABSTRACT

Compositions comprising polynucleotides encoding heavy and light chains of antibodies that interact with osteoprotegerin ligand (OPGL) are described. Methods of making such antibodies are described.

40 Claims, 11 Drawing Sheets

OTHER PUBLICATIONS

Kong et al., "OPGL is a key regulator of osteoclastogenesis, lymphocyte development and lymph-node organogenesis," *Nature*, 397:315-323 (1999).
Kong et al., "Osteoprotegerin ligand: a regulator of immune responses and bone physiology," *Immun. Today*, 21(10): 495-502 (2000).
Lacey et al., "Osteoprotegerin Ligand Is a Cytokine that Regulates Osteoclast Differentiation and Activation," *Cell*, 93:165-176 (1998).
Lacey et al., "Osteoprotegerin Ligand Modulates Murine Osteoclast Survival in Vitro and in Vivo," *Am. J. Pathol.*, 157:435-448 (2000).
Nakagawa et al., "RANK is the Essential Signaling Receptor for Osteoclast Differentiation Factor in Osteoclastogenesis," *Biochem. Biophys. Res. Comm.*, 253:395-400 (1998).
Stressgen product use sheet for product No. AAM-425AF, Mouse Anti-TRANCE Monoclonal Antibody clone No. 12A668, revised Jun. 27, 2005.
Takahashi et al., "A New Member of Tumor Necrosis Factor Ligand Family, ODF/OPGL/TRANCE/RANKL, Regulates Osteoclast Differentiation and Function," *Biochem. Biophys. Res. Comm.*, 256(3):449-455 (1999).
Tsukii et al., "Osteoclast Differentiation Factor Mediates an Essential Signal for Bone Resorption Induced by 1 alpha, 25-Dihydroxyvitamin $D_3$, Prostaglandin $E_2$, or Parathyroid Hormone in the Microenvironment of Bone," *Biochem. Biophys. Res. Comm.*, 246(2):337-341 (1998).
Wong et al., "TRANCE Is a Novel Ligand of the Tumor Necrosis Factor Receptor Family that Activates c-Jun N-Terminal Kinase in T Cells," *J. Biol. Chem.*, 272:25190-25194 (1997).
Wong et al., "TRANCE (Tumor Necrosis Factor [TNF]-related Activation-Induced Cytokine), a New TNF Family Member Predominantly Expressed in T Cells, Is a Dentritic Cell-specific Survival Factor, " *J. Exp. Med.*, 186:2075-2080 (1997).
Yasuda et al., "Osteoclast differentiation factor is a ligand for osteoprotegerin/ osteoclastogenesis-inhibitory factor and is identical to TRANCE/RANKL," *Proc. Natl. Acad. Sci. USA*, 95:3597-3602 (1998).
Response with Exhibits A and B filed in U.S. Appl. No. 09/211,315 on Aug. 18, 2000.
Office Action in U.S. Appl. No. 09/718,726 mailed on Jun. 4, 2003.
Office Action in U.S. Appl. No. 09/211,297 mailed on Mar. 27, 2003.
Preliminary Amendment filed in U.S. Appl. No. 09/466,496 on Dec. 17, 1999.
Office Action in U.S. Appl. No. 09/466,496 mailed on Jul. 31, 2001.
Amendment and Response to Office Action filed in U.S. Appl. No. 09/466,496 on Nov. 29, 2001.
Supplemental Amendment filed in U.S. Appl. No. 09/466,496 on Feb. 22, 2002.
Amendment and Response to Office Action filed in U.S. Appl. No. 09/466,496 on Aug. 6, 2002.
Preliminary Amendment filed in U.S. Appl. No. 09/577,800 on May 24, 2000.
Third Preliminary Amendment filed in U.S. Appl. No. 09/577,800 on Jul. 26, 2001.
Preliminary Amendment filed in U.S. Appl. No. 09/871,856 on May 31, 2001.
Second Preliminary Amendment filed in U.S. Appl. No. 09/871,856 on Dec. 12, 2002.
Amendment and Response to Paper No. 12 with Exhibits A to D, filed in U.S. Appl. No. 09/705,985 on Apr. 3, 2003.
Communication pursuant to Article 96(2) EPC in European Patent Application No. 02 749 660.3—1222 dated Jun. 9, 2006.
First Office Action and Text of the First Office Action in Chinese Patent Application No. 02816680.9, dated Feb. 24, 2006, with English translation.
English Translation of Office Action in Taiwan Patent Application No. 91114055, dated Sep. 7, 2005.
Examiner's first report dated Jan. 30, 2007, in Australian Patent Application No. 2002320157.
Official Notification on the necessity of submitting additional materials dated Sep. 4, 2006, in Eurasian Patent Application No. 200400063/28, with English translation.
Office Action in U.S. Appl. No. 10/180,648 mailed on Apr. 29, 2005.
Amendment and Response to Office Action (Restriction Requirement) filed in U.S. Appl. No. 10/180,648 on Jul. 29, 2005.
Examiner-Initiated Interview Summary in U.S. Appl. No. 10/180,648 mailed on Sep. 27, 2005.
Applicant Statement of Interview Summary filed in U.S. Appl. No. 10/180,648 on Oct. 14, 2005.
Office Action in U.S. Appl. No. 10/180,648 mailed on Oct. 21, 2005.
Amendment and Response filed in U.S. Appl. No. 10/180,648 on Jan. 25, 2006.
Office Action in U.S. Appl. No. 10/180,648 mailed on Apr. 18, 2006.
Amendment After Final filed in U.S. Appl. No. 10/180,648 on Jul. 18, 2006.
Advisory Action Before the Filing of an Appeal Brief in U.S. Appl. No. 10/180,648 mailed on Aug. 7, 2006.
Amendment filed in U.S. Appl. No. 10/180,648 on Sep. 18, 2006.
Office Action in U.S. Appl. No. 10/180,648 mailed on Dec. 13, 2006.
Amendment and Response and Interview Summary filed in U.S. Appl. No. 10/180,648 on Mar. 13, 2007.
Office Action in U.S. Appl. No. 10/180,648 mailed on Jun. 19, 2007.
Amendment and Response After Final filed in U.S. Appl. No. 10/180,648 on Sep. 18, 2007.
Notice of Allowance and Fee(s) Due in U.S. Appl. No. 10/180,648 mailed on Oct. 18, 2007.
Application for Patent Term Adjustment Under 37 C.F.R. § 1.705(b) filed in U.S. Appl. No. 10/180,648 on Dec. 7, 2007.
Decision Granting Petition in U.S. Appl. No. 10/180,648 mailed on Mar. 17, 2008.
Office Action, including Taiwan IPO Search Report, in Taiwan Patent Application No. 95103780, dated Sep. 8, 2008.
English Translation of Office Action, including Taiwan IPO Search Report, in Taiwan Patent Application No. 95103780, dated Sep. 8, 2008, provided by Taiwanese counsel.
Nagai et al., "Cancer Cells Responsible for Humoral Hypercalcemia Express mRNA Encoding a Secreted Form of ODF/TRANCE that Induces Osteoclast Formation," *Biochem. Biophys. Res. Comm.*, 269:532-536 (2000).
Oyajobi et al., "Therapeutic Efficacy of a Soluble Receptor Activator of Nuclear Factor κB-IgG Fc Fusion Protein in Suppressing Bone Resorption and Hypercalcemia in a Model of Humoral Hypercalcemia of Malignancy," *Cancer Res.*, 61: 2572-2578 (2001).
"Appendix" from *Monoclonal Antibodies: Practical Approach*, Shepherd and Dean (Eds.), Oxford University Press, New York, pp. 58-65 (2000).
Translation of Notice of Rejection ($1^{st}$ Official Action), mailed Jan. 8, 2008, for Japanese Patent Application No. 2003-509075 (8 pages).
Examiner's report No. 2, dated Jun. 6, 2008, for Australian Patent Application No. 2002320157 (2 pages).
Translation of Second Office Action, dated Feb. 1, 2008, for Chinese Patent Application No. 02816680.9 (8 pages).
Translation of Decision on Rejection dated Jan. 16, 2009, for Chinese Patent Application No. 02816680.9 (8 pages).
Translation of Reexamination Decision (Decision No. 18367), dated Jul. 1, 2009, for Chinese Patent Application No. 02816680.9 (1 page).
Translation of Official Notification on the necessity of submitting additional materials, dated Nov. 19, 2007, for Eurasian Patent Application No. 200400063/28 (7 pages).
Communication pursuant to Article 96(2) EPC, dated Jul. 3, 2007, for European Patent Application No. 02749660.3 (8 pages).
Summons to attend oral proceedings pursuant to Rule 115(1) EPC, dated Nov. 25, 2008, for European Patent Application No. 02749660.3 (7 pages).
Invitation pursuant to Article 94(3) and Rule 71(1) EPC, dated Mar. 30, 2009, for European Patent Application No. 02749660.3 (2 pages).
Translation of Notice of Provisional Refusal, dated Nov. 24, 2008, for Korean Patent Application No. 10-2003-7017009 (3 pages).
Substantive Examination Adverse Report (Section 30(1)/30(2)), dated Sep. 26, 2008, for Malaysian Patent Application No. PI 20022368 (2 pages).
Substantive Examination Adverse Report (Section 30(1)/30(2)), dated May 5, 2009, for Malaysian Patent Application No. PI 20022368 (2 pages).

Translation of the Requirements Stated by the Examiner for Mexican Patent Application No. PA/a/2004/000134 (2 pages).
First Action, mailed Apr. 24, 2007, for Philippine Patent Application No. 1-2003-501360 (2 pages).
Subsequent Action, mailed Aug. 22, 2008, for Philippine Patent Application No. 1-2003-501360 (2 pages).
Examination Report, dated Jun. 15, 2006, for New Zealand Patent Application No. 547695 (1 page).
Examination Report, dated Mar. 3, 2008, for New Zealand Patent Application No. 547695 (1 page).
Examination Report, dated Jun. 3, 2008, for New Zealand Patent Application No. 568552 (2 pages).
Extended European Search Report, dated Jul. 13, 2009, for European Patent Application No. 09156995.4 (10 pages).
Response to Office Action, filed Oct. 14, 2008, for U.S. Appl. No. 09/211,297 (18 pages).
Final Office Action, mailed Jan. 13, 2009, for U.S. Appl. No. 09/211,297 (9 pages).
Request for Continued Examination and Response, with Exhibits A-H, filed Feb. 16, 2010, for U.S. Appl. No. 09/211,297 (75 pages).
Notice of Allowance and Fee(s) Due, mailed Mar. 22, 2010, for U.S. Appl. No. 09/211,297 (6 pages).
Petition to Revive under 37 CFR 1.137(b) and Response to Restriction Requirement, filed Dec. 19, 2007, for U.S. Appl. No. 09/791,153 (6 pages).
Notice of Non-compliant Amendment, mailed Jul. 22, 2009, for U.S. Appl. No. 09/791,153 (3 pages).
Response to Notice of Non-compliant Amendment and Preliminary Amendment, filed Aug. 21, 2009, for U.S. Appl. No. 09/791,153 (5 pages).
Non-final Office Action, mailed Sep. 23, 2009, for U.S. Appl. No. 09/791,153 (7 pages).
Amendment, filed Mar. 23, 2010, for U.S. Appl. No. 09/791,153 (10 pages).
Amendment and Response, filed Aug. 19, 2008, for U.S. Patent Application No. 11/336,067 (41 pages).
Final Office Action, mailed Oct. 28, 2008, for U.S. Appl. No. 11/336,067 (6 pages).
Request for Continued Examination, Amendment, Information Disclosure Statement, and Terminal Disclaimer to Obviate a Double-patenting Rejection Over a Prior Patent, filed Nov. 30, 2009, for U.S. Appl. No. 11/336,067 (20 pages).
Final Office Action, mailed Jan. 12, 2010, for U.S. Appl. No. 11/336,067 (6 pages).
Request for Continued Examination, Letter Transmitting (Terminal) Disclaimer, and Terminal Disclaimer to Obviate, a Provisional Double Patenting Rejection Over a Prior Patent, and Information Disclosure Statement, filed Apr. 20, 2010, for U.S. Appl. No. 11/336,067 (12 pages).
Notice of Allowance and Fee(s) Due, mailed Mar. 21, 2008, for U.S. Appl. No. 10/802,133 (6 pages).
Final Office Action, mailed Aug. 8, 2008, for U.S. Appl. No. 10/825,898 (10 pages).
Request for Continued Examination, Information Disclosure Statement, and Amendment to the Sequence Listing and Attorney's Statement Pursuant to 37 CFR 1.821, filed Sep. 3, 2009, for U.S. Appl. No. 10/825,898 (7 pages).
Final Office Action, mailed Sep. 17, 2009, for U.S. Appl. No. 10/825,898 (9 pages).
Amendment and Response, filed Mar. 17, 2010, for U.S. Appl. No. 10/825,898 (10 pages).
Non-final Office Action, mailed May 11, 2009, for U.S. Appl. No. 12/214,914 (7 pages).
Amendment and Response to Office Action, Information Disclosure Statement before Mailing Date of Either a Final Action or Notice of Allowance (37 CFR 1.97(c)), and Terminal Disclaimer to Obviate a Provisional Double Patenting Rejection Over a Prior Patent, filed Oct. 12, 2009, for U.S. Appl. No. 12/214,914 (12 pages).
Terminal Disclaimer to Obviate a Provisional Double Patenting Rejection Over a Prior Patent and Communication, filed Jan. 7, 2010, for U.S. Appl. No. 12/214,914 (5 pages).
Notice of Allowance and Fee(s) Due, mailed Feb. 5, 2010, for U.S. Appl. No. 12/214,914 (6 pages).
Request for Continued Examination and Information Disclosure Statement, filed Apr. 6, 2010, for U.S. Appl. No. 12/214,914 (5 pages).
Notice of Allowance and Fee(s) Due, mailed Apr. 12, 2010, for U.S. Appl. No. 12/214,914 (6 pages).
Supplemental Preliminary Amendment, filed Jul. 7, 2003, for U.S. Appl. No. 10/167,182 (16 pages).
Supplemental Preliminary Amendment, filed Apr. 16, 2004, for U.S. Appl. No. 10/167,182 (8 pages).
Restriction Requirement, mailed Mar. 14, 2005, for U.S. Appl. No. 10/167,182 (5 pages).
Interview Summary, mailed Mar. 23, 2005, for U.S. Appl. No. 10/167,182 (4 pages).
Response to Election Requirement, filed Mar. 30, 2005, for U.S. Appl. No. 10/167,182 (6 pages).
Non-final Office Action, mailed Jun. 22, 2005, for U.S. Appl. No. 10/167,182 (21 pages).
Amendment and Response to Office Action mailed Jun. 22, 2005, filed Aug. 3, 2005, for U.S. Appl. No. 10/167,182 (11 pages).
Non-final Office Action, mailed Nov. 6, 2006, for U.S. Appl. No. 10/167,182 (8 pages).
Amendment and Response to Office Action mailed Nov. 6, 2006, filed Apr. 17, 2007, for U.S. Appl. No. 10/167,182 (12 pages).
Final Office Action, mailed May 31, 2007, for U.S. Appl. No. 10/167,182 (10 pages).
Request for Continued Examination Transmittal and Amendment and Response to Final Office Action with Request for Continued Examination, filed Oct. 31, 2007, for U.S. Appl. No. 10/167,182 (15 pages).
Interview Summary, mailed Dec. 13, 2007, for U.S. Appl. No. 10/167,182 (4 pages).
Non-final Office Action, mailed Jan. 25, 2008, for U.S. Appl. No. 10/167,182 (13 pages).
Interview Summary, mailed Apr. 10, 2008, for U.S. Appl. No. 10/167,182 (4 pages).
Response to Office Action, filed May 21, 2008, for U.S. Appl. No. 10/167,182 (17 pages).
Notice of Allowance and Fee(s) Due, mailed Jul. 28, 2008, for U.S. Appl. No. 10/167,182 (4 pages).
Preliminary Amendment and Request for Interference with U.S. Application U.S. Appl. No. 09/211,297 ('297 Application), U.S. Appl. No. 09/079,569 ('569 Application), and U.S. Appl. No. 09/791,153 ('153 Application), filed May 27, 2004, for U.S. Appl. No. 10/854,300 (44 pages).
Restriction Requirement, mailed Mar. 14, 2005, for U.S. Appl. No. 10/854,300 (6 pages).
Response to Restriction Requirement, filed Apr. 11, 2005, for U.S. Appl. No. 10/854,300 (5 pages).
Non-final Office Action, mailed Jun. 22, 2005, for U.S. Appl. No. 10/854,300 (24 pages).
Amendment and Response to Office Action mailed Jun. 22, 2005, filed Oct. 24, 2005, for U.S. Appl. No. 10/854,300 (8 pages).
Final Office Action, mailed Jan. 11, 2006, for U.S. Appl. No. 10/854,300 (7 pages).
Notice of Appeal from the Examiner to the Board of Patent Appeals and Interferences, mailed Jul. 7, 2006, for U.S. Appl. No. 10/854,300 (1 page).
Appellant's Brief, filed Nov. 22, 2006, for U.S. Appl. No. 10/854,300 (24 pages).
Notification of Non-compliant Appeal Brief, mailed Dec. 28, 2006, for U.S. Appl. No. 10/854,300 (2 pages).
Revised Appellant's Brief, filed Jan. 5, 2007, for U.S. Appl. No. 10/854,300 (27 pages).
Non-final Office Action, mailed May 7, 2007, for U.S. Appl. No. 10/854,300 (12 pages).
Response and Amendment to Office Action, filed Nov. 7, 2007, for U.S. Appl. No. 10/854,300 (8 pages).
Interview Summary, mailed Dec. 13, 2007, for U.S. Appl. No. 10/854,300 (4 pages).
Final Office Action, mailed Jan. 25, 2008, for U.S. Appl. No. 10/854,300 (10 pages).
Interview Summary, mailed Apr. 10, 2008, for U.S. Appl. No. 10/854,300 (2 pages).

Response and Amendment to Final Office Action, filed May 21, 2008, for U.S. Appl. No. 10/854,300 (16 pages).
Notice of Allowance and Fee(s) Due, mailed Jul. 1, 2008, for U.S. Appl. No. 10/854,300 (4 pages).
Examiner's First Report, mailed Sep. 7, 2009, for Australian Patent Application No. 2008202516 (8 pages).
Communication pursuant to Article 94(3) EPC, mailed Nov. 24, 2008, for European Patent Application No. 06015956.3 (4 pages).
Translation of Official action, for Brazilian Patent Application No. PI9808545-0, issued on Jun. 17, 2008 (7 pages).
Translation of Office Action, for Brazilian Patent Application No. PI9808545-0, published Dec. 9, 2008 (4 pages).
Technical Examination Report—Third Technical Report, including translation, for Brazilian Patent Application No. PI9808545-0, dated May 26, 2009 (10 pages).
Technical Examination Report—Fourth Technical Report, including translation, for Brazilian Patent Application No. PI9808545-0, dated Jan. 7, 2010 (18 pages).
Examination report for Canadian Patent Application No. 2,285,746, mailed Jun. 11, 2008 (3 pages).
Fifth Office Action, including translation, issued Nov. 6, 2009, for Chinese Patent Application No. 98806073.6 (8 pages).
Sixth Office Action, including translation, issued Apr. 30, 2010, for Chinese Patent Application No. 98806073.6 (10 pages).
Notice of Reexamination, including translation, issued Oct. 23, 2008, for Chinese Patent Application No. 98806073.6 (8 pages).
Reexamination Decision (Decision No. 17505), including translation of cover pages, issued Jun. 18, 2009, for Chinese Patent Application No. 98806073.6 (9 pages).
Translation of Examiner's Report, dated Jan. 31, 2008, for Czech Patent Application No. PV 1999-3598 (4 pages).
Translation of Official Letter, dated Oct. 6, 2008, for Romanian Patent Application No. 99-01101 (2 pages).
Examiner's First Report, mailed May 20, 2005, for Australian Patent Application No. 2001238680 (2 pages).
Examination report, mailed Jul. 30, 2007, for Canadian Patent Application No. 2,400,929 (4 pages).
Examination report, mailed Oct. 2, 2006, for Canadian Patent Application No. 2,400,929 (6 pages).
Examination report, mailed Oct. 6, 2008, for Canadian Patent Application No. 2,400,929 (5 pages).
Examination report, mailed Dec. 18, 2009, for Canadian Patent Application No. 2,400,929 (1 page).
Notice of Rejection (1st Official Action), including translation, mailed Mar. 18, 2008, for Japanese Patent Application No. 2001-562706 (5 pages).
Translation of Notice of Rejection (2nd Official Action), mailed Jan. 13, 2009, for Japanese Patent Application No. 2001-562706 (3 pages).
Translation of the requirements stated by the Examiner, sent Mar. 12, 2008, for Mexican Patent Application No. Pa/a/2002/0008144 (3 pages).
Translation of the requirements stated by the Examiner, sent Jun. 27, 2006, for Mexican Patent Application No. Pa/a/2002/0008144 (7 pages).
Office Action of the IPO, including translation, received Apr. 9, 2009, for Taiwanese Patent Application No. 090104205 (10 pages).
Decision of the Intellectual Property Office, including translation, received Dec. 30, 2002, for Taiwanese Patent Application No. 090104205 (5 pages).
Examiner's Re-examination report, mailed May 20, 2008, for Australian Patent Application No. 735355 (2 pages).
Examination report, mailed May 17, 2004, for Canadian Patent Application No. 2,257,247 (5 pages).
Examination report, mailed Jul. 13, 1999, for Canadian Patent Application No. 2,257,247 (1 page).
Examination report, mailed Nov. 27, 2008, for Canadian Patent Application No. 2,257,247 (3 pages).
Examination report, mailed Dec. 2, 2002, for Canadian Patent Application No. 2,257,247 (7 pages).
English translation of the Second Office Action, dispatched May 23, 2003, for Chinese Patent Application No. 98800477.1 (7 pages).

English translation of the First Office Action, dispatched Sep. 6, 2002, for Chinese Patent Application No. 98800477.1 (12 pages).
Resolution, including translation, mailed Feb. 19, 2008, for Hungarian Patent Application No. P0000717/10 (7 pages).
Notification on the performance of novelty search, including translation, mailed Sep. 19, 2006, for Hungarian Patent Application No. P0000717/8 (5 pages).
English translation of Notification of Defects, dated Apr. 29, 2008, for Israeli Patent Application No. 127115 (1 page).
English translation of Notice of Preliminary Rejection, dispatched Apr. 13, 2004, for Korean Patent Application No. 10-2003-7009671 (2 pages).
English translation of Notice of Preliminary Rejection, dispatched Oct. 10, 2003, for Korean Patent Application No. 10-2003-7009671 (1 page).
English translation of Notice of Preliminary Rejection, dispatched Nov. 30, 2004, for Korean Patent Application No. 10-2003-7009671 (1 page).
English translation of Final Rejection, dated Apr. 4, 2003, for Korean Patent Application No. 10-1998-071094 (1 page).
English translation of Notice of Preliminary Rejection, dispatched May 31, 2002, for Korean Patent Application No. 10-1998-071094 (1 page).
English translation of Notice of Preliminary Rejection, dispatched Sep. 19, 2003, for Korean Patent Application No. 10-1998-071094 (1 page).
Notice of Opposition to a European patent by Opponent Schering Corporation, filed Apr. 9, 2009, opposing European Patent No. 0951551 B1 (1408 pages).
Notice of Opposition to a European patent by Opponent Ablynx NV, filed Apr. 15, 2009, opposing European Patent No. 0951551 B1 (898 pages).
Communication of notices of opposition, mailed May 28, 2009, for European Patent No. 0951551 B1 (1 page).
Proprietor's Observations Filed in response to the Communication pursuant to Rule 79(1) EPC dated May 28, 2009, filed Feb. 8, 2010, for European Patent No. 0951551 B1 (254 pages).
Notice of Opposition by Opponent Amgen Inc., filed Feb. 28, 2007, opposing European Patent No. 0911342 (424 pages).
Notice of Opposition by Opponent Schering-Plough Corporation, filed Feb. 28, 2007, opposing European Patent No. 0911342 (128 pages).
Withdrawal of Opposition filed by Opponent Amgen Inc., filed Oct. 1, 2007, for European Patent No. 0911342 (1 page).
Reply to oppositions filed by Schering-Plough Corporation and Amgen on Feb. 28, 2007, filed Dec. 14, 2007, for European Patent No. 0911342 (25 pages).
Response to the Submission of the Proprietor dated Dec. 14, 2007, filed Aug. 11, 2008, for European Patent No. 0911342 (37 pages).
Notice of Opposition to a European patent by Opponent Schering Corporation, filed Feb. 28, 2008, opposing European Patent No. 0975754 B1 (869 pages).
Notice of Opposition to a European patent by Opponent Ablynx N.V., filed Mar. 3, 2008, opposing European Patent No. 0975754 B1 (901 pages).
Response of the Patentee Amgen Inc. to the Oppositions filed by Schering Corporation and Ablynx NV, filed Dec. 16, 2008, for European Patent No. 0975754 B1 (17 pages).
Summons to attend oral proceedings pursuant to Rule 115(1) EPC, mailed Sep. 14, 2009, for European Patent No. 0975754 B1 (12 pages).
Notice of Opposition to a European patent by Opponent Eli Lilly and Company, filed Mar. 17, 2009, opposing European Patent No. 1257648 (764 pages).
Communication of notices of opposition (R. 79(1) EPC), mailed May 15, 2009, for European Patent No. 1257648 (1 page).
Response to the opposition brief dated Mar. 17, 2009, filed Jan. 25, 2010, for European Patent No. 1257648 (36 pages).
Bendele et al., "Effects of Interleukin 1 Receptor Antagonist Alone and in Combination with Methotrexate in Adjuvant Arthritic Rats," *J. Rheumatol.*, 26(6): 1225-1229 (1999).
Substantive Examination, including translation, issued Jan. 4, 2010, for Argentine Patent Application No. P20020102401 (7 pages).

Examination report, mailed Mar. 9, 2010, for Canadian Patent Application No. 2,451,955 (5 pages).
Third Report, with translation, stamped Apr. 16, 2008, for Chilean Patent Application No. 1407-2002 (9 pages).
Official Notification of the necessity of submitting additional materials, with translation, dispatched Jul. 10, 2009, for Eurasian Patent Application No. 200400063/28 (21 pages).
Invitation pursuant to Article 94(3) and Rule 71(1) EPC, mailed Sep. 7, 2009, for European Patent Application No. 02749660.3 (4 pages).
Communication under Rule 71(3) EPC, mailed Jan. 19, 2010, for European Patent Application No. 02749660.3 (6 pages).
Communication pursuant to Article 94(3) EPC, mailed Mar. 8, 2010, for European Patent Application No. 09156995.4 (1 page).
Official Action, with translation, mailed Mar. 5, 2009, for Israeli Patent Application No. 159512 (4 pages).
English translation of Decision for Final Refusal, mailed Sep. 25, 2009, for Korean Patent Application No. 10-2003-7017009 (2 pages).
English translation of Substantive Examination Adverse Report (Section 30(1)/30(2)) mailed Nov. 30, 2009, for Malaysian Patent Application No. PI20022368 (2 pages).
Examination Report, mailed Dec. 8, 2009, for New Zealand Patent Application No. 581637 (2 pages).
Office Action, Paper No. 19, mailed Oct. 14, 2009, for Philippine Patent Application No. 1-2003-501360 (2 pages).
Office Action, with translation, mailed Nov. 23, 2009, for Serbian Patent Application No. P-1030/2003 (5 pages).
Invitation to Respond to Written Opinion, mailed Nov. 12, 2009, for Singaporean Patent Application No. 200508119-5 (8 pages).
Office Action, with translation, mailed Sep. 15, 2009, for Taiwanese Patent Application No. 95103780 (13 pages).
Notice of Provisional Refusal, dated May 31, 2010, received Aug. 3, 2010, with translation, for Korean Patent Application No. 10-2010-7002067 (5 pages).
Official Notification on the necessity of submitting additional materials, dated Jun. 18, 2010, received Jul. 29, 2010, with translation, for Eurasian Patent Application No. 200400063/28 (19 pages).
Office Action, Paper No. 28, mailed Jul. 30, 2010, for Philippine Patent Application No. 1-2003-501360 (2 pages).
Official Action, with translation, mailed Aug. 24, 2010, for Israeli Patent Application No. 159512 (3 pages).
Communication including the Extended European Search Report, mailed Jan. 28, 2011, for European Patent Application No. 10181323.6 (15 pages).
Communication including the Extended European Search Report, mailed Feb. 11, 2011, for European Patent Application No. 10185344.8 (14 pages).
Maini et al., "Infliximab (chimeric anti-tumour necrosis factor α monoclonal antibody) versus placebo in rheumatoid arthritis patients receiving concomitant methotrexate: a randomised phase III trial," The Lancet, 354: 1932-1939 (1999).
Pavlinkova et al., "Pharmacokinetics and Biodistribution of Engineered Single-Chain Antibody Constructs of MAb CC49 in Colon Carcinoma Xenografts," J. Nuclear Medicine, 40(9): 1536-1546 (1999).
Welschof et al., "The Antigen Binding Domain of Non-idiotypic Human Anti-F(ab')$_2$ Autoantibodies: Study of their interaction with IgG hinge region epitopes," Human Immunology, 60: 282-290 (1999).
Request for Continued Examination and Information Disclosure Statement, filed Apr. 20, 2010, for U.S. Appl. No. 09/211,297 (7 pages).
Notice of Allowance and Fee(s) Due, mailed May 10, 2010, for U.S. Appl. No. 09/211,297 (8 pages).
Response to Notice of Improper Request for Continued Examination (RCE), with attachments, filed Jul. 12, 2010, for U.S. Appl. No. 11/336,067 (17 pages).
Notice of Allowance and Fee(s) Due, mailed Aug. 6, 2010, for U.S. Appl. No. 11/336,067 (27 pages).
Request for Continued Examination (RCE) Transmittal and Information Disclosure Statement, filed Nov. 8, 2010, for U.S. Appl. No. 11/336,067 (9 pages).
Notice of Allowance and Fee(s) Due, mailed Nov. 30, 2010, for U.S. Appl. No. 11/336,067 (10 pages).
Office Action, mailed May 25, 2010, for U.S. Appl. No. 10/825,898 (4 pages).
Response to Restriction Requirement, filed Nov. 23, 2010, for U.S. Appl. No. 10/825,898 (4 pages).
Office Action, mailed Dec. 2, 2010, for U.S. Appl. No. 10/825,898 (11 pages).
Response to Notice of Non-compliant Amendment (37 CFR 1.121), filed Aug. 17, 2010, for U.S. Appl. No. 09/791,153 (4 pages).
Office Action, mailed Nov. 9, 2010, for U.S. Appl. No. 09/791,153 (14 pages).
Interview Summary, mailed Apr. 4, 2011, for U.S. Appl. No. 09/791,153 (3 pages).
Office Action mailed Jun. 1, 2010, for U.S. Appl. No. 12/340,327 (6 pages).
Response to Restriction Requirement, filed Nov. 1, 2010, for U.S. Appl. No. 12/340,327 (6 pages).
Office Action, mailed Dec. 17, 2010, for U.S. Appl. No. 12/340,327 (23 pages).
Office Action, mailed May 19, 2008, for U.S. Appl. No. 11/513,178 (7 pages).
Notice of Abandonment, mailed Jan. 2, 2009, for U.S. Appl. No. 11/513,178 (2 pages).
Summons to attend oral proceedings pursuant to Rule 115(1) EPC, mailed Oct. 22, 2010, for European Patent No. 1257648 (19 pages).
Written Submissions in preparation of Oral Proceedings scheduled for Apr. 15, 2011, filed Feb. 15, 2011, for European Patent No. 1257648 (59 pages).
Letter filed in preparation for oral proceedings pursuant to Rule 116 EPC, filed Feb. 15, 2011, for European Patent No. 1257648 (59 pages).
Letter requesting accelerated grant, filed Feb. 25, 2010, for European Patent Application No. 02749660.3 (13 pages).
Amendment or correction of the text intended for grant, mailed Mar. 12, 2010, for European Patent Application No. 02749660.3 (1 page).
Decision to grant a European patent pursuant to Article 97(1) EPC, mailed Mar. 18, 2010, for European Patent Application No. 02749660.3 (3 pages).
Notice of opposition to a European patent by opponent Teva Pharmaceutical Industries Ltd., filed Jan. 14, 2011, for European Patent No. 1409016 (462 pages).
Summons to attend oral proceedings pursuant to Rule 115(1) EPC, mailed Mar. 7, 2011, for European Patent No. 0911342 (13 pages).
Summons to attend oral proceedings pursuant to Rule 115(1) EPC, mailed Jan. 3, 2011, for European Patent No. 0951551 (13 pages).
Proprietor's Observations under Rule 116 EPC Prior to Oral Proceedings on Sep. 23, 2010, filed Jul. 23, 2010, for European Patent No. 0975754 (64 pages).
Letter filed in preparation of the oral proceedings scheduled for Sep. 23, 2010, by opponent Schering Corporation, filed Jul. 23, 2010 for European Patent No. 0975754 (65 pages).
Further submissions of O2, Ablynx N.V., filed Jul. 23, 2010, for European Patent No. 0975754 (42 pages).
Provision of the minutes in accordance with Rule 124(4) EPC, mailed Oct. 15, 2010, for European Patent No. 0975754 (28 pages).
Decision revoking the European Patent (Art 101(2) and 101(3)(b) EPC), mailed Oct. 15, 2010, for European Patent No. 0975754 (51 pages).
Notice of Appeal, filed in the name of and on behalf of Amgen Inc., filed Nov. 23, 2010, for European Patent No. 0975754 (2 pages).
Grounds of Appeal, filed in the name of and on behalf of Amgen Inc., filed Feb. 25, 2011, for European Patent No. 0975754 (273 pages).
Translation of Decision on Rejection, issued Feb. 24, 2011, for Chinese Patent Application No. 98806073.6 (19 pages).

Translation of Examiner's opinion, mailed Dec. 22, 2010, for Estonian Patent Application No. 199900611 (2 pages).
Communication of the extended European search report, mailed May 23, 2007, for European Patent Application No. 06015956.3 (16 pages).
Communication pursuant to Article 94(3) EPC, mailed Feb. 19, 2008, for European Patent Application No. 06015956.3 (8 pages).
Response to the communication of Feb. 19, 2008, filed Aug. 29, 2008, for European Patent Application No. 06015956.3 (5 pages).
Noting of loss of rights pursuant to Rule 112(1) EPC, mailed Jul. 13, 2009, for European Patent Application No. 06015956.3 (1 page).
Response to the communication of Nov. 24, 2008, filed Sep. 23, 2009, for European Patent Application No. 06015956.3 (6 pages).
Decision on the request for further processing under Rule 135(3) EPC, mailed Oct. 5, 2009, for European Patent Application No. 06015956.3 (1 page).
Communication pursuant to Article 94(3) EPC, mailed Jan. 19, 2011, for European Patent Application No. 06015956.3 (5 pages).
Reply to Invitation to Remedy Deficiencies Pursuant to Rule 58 EPC, dated Nov. 17, 2010, filed Jan. 26, 2011, for European Patent Application No. 10184791.1 (6 pages).
Letter filed in response to the Official Communication of Nov. 11, 2010, filed Jan. 13, 2011, for European Patent Application No. 10013041.8 (5 pages).
Letter filed in response to the Official Communication of Oct. 28, 2010, filed Jan. 7, 2011, for European Patent Application No. 10010586 (5 pages).
Publication details for Hong Kong Patent No. 1136308 from the Hong Kong Intellectual Property Journal No. 377, published Jun. 25, 2010, pp. 117-118 of 297.
Translation of Resolution, mailed Sep. 2, 2010, for Hungarian Patent Application No. P0000717/15 (5 pages).
Letter filed in Reply to the Invitation to remedy deficiencies (R. 58 EPC) dated Nov. 17, 2010, filed Jan. 26, 2011, for European Patent Application No. 10186133.4 (10 pages).
Notice of Allowance, mailed Sep. 21, 2010, for Canadian Patent Application No. 2,400,929 (1 page).
Communication of the extended European search report, mailed Jan. 18, 2006, for European Patent Application No. 05017241.0 (8 pages).
Communication pursuant to Article 96(2) EPC, mailed Nov. 9, 2006, for European Patent Application No. 05017241.0 (1 page).
Letter filed in reply to the Communication of Nov. 9, 2006, filed Mar. 13, 2007, for European Patent Application No. 05017241.0 (7 pages).
Communication pursuant to Article 96(2) EPC, mailed Nov. 23, 2007, for European Patent Application No. 05017241.0 (3 pages).
Letter filed in reply to the Communication of Nov. 23, 2007, filed May 30, 2008, for European Patent Application No. 05017241.0 (10 pages).
Communication pursuant to Article 94(3) EPC, mailed Sep. 22, 2009, for European Patent Application No. 05017241.0 (5 pages).
Noting of loss of rights pursuant to Rule 112(1) EPC, mailed May 10, 2010, for European Patent Application No. 05017241.0 (1 page).
Reply to Communication Noting of Loss of rights Pursuant to Rule 112(1) EPC of May 10, 2010 and to the Communication Pursuant to Article 94(3) EPC dated Sep. 22, 2009, filed Jul. 20, 2010, for European Patent Application No. 05017241.0 (14 pages).
Decision on the request for further processing under Rule 135(3) EPC, mailed Aug. 4, 2010, for European Patent Application No. 05017241.0 (1 page).
Examiner's First Report, mailed Sep. 3, 2010, for Australian Patent Application No. 2008200700 (3 pages).
Notice of Opposition, filed Oct. 5, 2001, for Australian Patent No. 735355 (4 pages).
Statement of Grounds and Particulars in support of opposition, filed Jan. 4, 2002, for Australian Patent No. 735355 (28 pages).
Statutory Declaration of Nigel John Parker, signed May 1, 2003, for Australian Patent No. 735355 (80 pages).
Statutory Declaration of Mathew Alexander Vadas, signed May 1, 2003, for Australian Patent No. 735355 (71 pages).

Declaration of Rodney Ian Lindsay Cruise, signed May 2, 2003, for Australian Patent No. 735355 (16 pages).
Statutory Declaration of Thomas John Martin, signed Apr. 2, 2004, for Australian Patent No. 735355 (33 pages).
Withdrawal of Opposition, filed Feb. 15, 2008, for Australian Patent No. 735355 (1 page).
Examiner's first report, mailed Dec. 22, 2010, for Australian Patent Application No. 2008261137 (3 pages).
Response to the Official Report, filed Feb. 22, 2011, for Australian Patent Application No. 2008261137 (20 pages).
Examiner's report No. 2, mailed Mar. 7, 2011, for Australian Patent Application No. 2008261137 (2 pages).
Response to Official Action, filed Sep. 9, 2010, for Canadian Patent Application No. 2,451,955 (32 pages).
Voluntary Amendment, filed Oct. 28, 2010, for Canadian Patent Application No. 2,451,955 (1 page).
Response to communication of Mar. 8, 2010, filed Sep. 20, 2010, for European Patent Application No. 09156995.4 (6 pages).
Communication pursuant to Article 94(3) EPC, mailed Oct. 5, 2010, for European Patent Application No. 09156995.4 (8 pages).
Transmittal letter for new divisional application and claims, as filed Sep. 28, 2010, for European Patent Application No. 10181323 (6 pages).
Reply to Invitation to Remedy Deficiencies Pursuant to Rule 58 EPC, dated Oct. 15, 2010, filed Dec. 22, 2010, for European Patent Application No. 10185344.8 (10 pages).
Memorandum in Response to Official Action of Aug. 24, 2010, filed Mar. 7, 2011, for Israeli Patent Application No. 159512 (20 pages).
Response and Amendment of Claims, with English translation of the claims, filed Oct. 29, 2010, for Korean Patent Application No. 10-2010-7002067 (53 pages).
Decision for Allowance of the Application, with translation, mailed Feb. 28, 2011, for Korean Patent Application No. 10-2010-7002067 (3 pages).
Dismissal of appeal filed against the final rejection, mailed Dec. 24, 2010, for Korean Patent Application No. 10-2003-7017009 (7 pages).
Voluntary Amendment which conforms to Article 61 of the Industrial Property Law, filed Oct. 18, 2010, for Mexican Patent Application No. PA/a/2004/000134 (27 pages).
Letter from Uhthoff Gomez Vega & Uhthoff, S.C. concerning Official Communication, with a redaction, mailed Dec. 17, 2010, for Mexican Patent Application No. PA/a/2004/000134 (2 pages).
Response to the official action Paper No. 28, filed Dec. 28, 2010, for Philippine Patent Application No. 1-2003-501360 (2 pages).
Request for revival and Response to the Official Action, filed Aug. 19, 2010, for Serbian Patent Application No. P-1030/2003 (4 pages).
Amendment to Response to the Official Action, filed Aug. 30, 2010, for Serbian Patent Application No. P-1030/2003 (11 pages).
Second Official Action, dated Dec. 10, 2010, with English summary from Serbian counsel, for Serbian Patent Application No. P-1030/2003 (5 pages).
Invitation to Respond to Written Opinion, mailed Oct. 29, 2010, for Singapore Patent Application No. 200508119-5 (7 pages).
Response to Written Opinion, filed Mar. 29, 2011, for Singapore Patent Application No. 200508119-5 (6 pages).
Aubin et al., "Osteoprotegerin and its Ligand: A New Paradigm for Regulation of Osteoclastogenesis and Bone Resorption," Osteoporosis International, 11: 905-913 (2000).
Gardnerova et al., "The Use of TNF Family Ligands and Receptors and Agents which Modify their Interaction as Therapeutic Agents," Current Drug Targets, 1: 327-364 (2000).
Hofbauer et al., "The Roles of Osteoprotegerin and Osteoprotegerin Ligand in the Paracrine Regulation of Bone Resorption," J. Bone Mineral Research, 15(1): 2-12 (2000).
Stigbrand et al., "Alternative Technologies to Generate Monoclonal Antibodies," Acta Oncologica, 32(7/8): 841-844 (1993).

Thomas et al., "Breast Cancer Cells Interact with Osteoblasts to Support Osteoclast Formation," Endocrinology, 140(10): 4451-4458 (1999).

Yasuda et al., "A Novel Molecular Mechanism Modulating Osteoclast Differentiation and Function," Bone, 25(1): 109-113 (1999).

*Pschyrembel Klinisches Wörterbuch 257th Edition*, pp. 248 and 1711 (1994).

Official Action and Norwegian Search Report, with translation, mailed Jun. 6, 2011, for Norwegian Patent Application No. 20041018 (7 pages).

Final Office Action for Argentinean Patent Application No. P02 01 02401 (4 pages), with translation (pp. 1-2 of 5), mailed Jul. 11, 2011.

Communication pursuant to Article 94(3) EPC mailed Jul. 4, 2011, for European Patent Application No. 09156995.4 (8 pages).

Official Action for Serbian Patent Application No. P-1030/2003 (3 pages), dated Jun. 28, 2011, with translation (3 pages).

Search and Examination Report for Singapore Patent Application No. 200508119-5, dated Jul. 19, 2011.

* cited by examiner

```
   1 AAGCTTGACC ACCATGGAGT TTGGGCTGAG CTGGCTTTTT CTTGTGGCTA TTTTAAAAGG
  61 TGTCCAGTGT GAGGTGCAGC TGTTGGAGTC TGGGGGAGGC TTGGTACAGC CTGGGGGGTC
 121 CCTGAGACTC TCCTGTGCAG CCTCTGGATT CACCTTTAGC AGCTATGCCA TGAGCTGGGT
 181 CCGCCAGGCT CCAGGGAAGG GGCTGGAGTG GGTCTCAGGT ATTACTGGGA GTGGTGGTAG
 241 TACATACTAC GCAGACTCCG TGAAGGGCCG GTTCACCATC TCCAGAGACA ATTCCAAGAA
 301 CACGCTGTAT CTGCAAATGA ACAGCCTGAG AGCCGAGGAC ACGGCCGTAT ATTACTGTGC
 361 GAAAGATCCA GGGACTACGG TGATTATGAG TTGGTTCGAC CCCTGGGGCC AGGGAACCCT
 421 GGTCACCGTC TCCTCAGCCT CCACCAAGGG CCCATCGGTC TTCCCCCTGG CGCCCTGCTC
 481 CAGGAGCACC TCCGAGAGCA CAGCGGCCCT GGGCTGCCTG GTCAAGGACT ACTTCCCCGA
 541 ACCGGTGACG GTGTCGTGGA ACTCAGGCGC TCTGACCAGC GGCGTGCACA CCTTCCCAGC
 601 TGTCCTACAG TCCTCAGGAC TCTACTCCCT CAGCAGCGTG GTGACCGTGC CCTCCAGCAA
 661 CTTCGGCACC CAGACCTACA CCTGCAACGT AGATCACAAG CCCAGCAACA CCAAGGTGGA
 721 CAAGACAGTT GAGCGCAAAT GTTGTGTCGA GTGCCCACCG TGCCCAGCAC CACCTGTGGC
 781 AGGACCGTCA GTCTTCCTCT TCCCCCCAAA ACCCAAGGAC ACCCTCATGA TCTCCCGGAC
 841 CCCTGAGGTC ACGTGCGTGG TGGTGGACGT GAGCCACGAA GACCCCGAGG TCCAGTTCAA
 901 CTGGTACGTG GACGGCGTGG AGGTGCATAA TGCCAAGACA AAGCCACGGG AGGAGCAGTT
 961 CAACAGCACG TTCCGTGTGG TCAGCGTCCT CACCGTTGTG CACCAGGACT GGCTGAACGG
1021 CAAGGAGTAC AAGTGCAAGG TCTCCAACAA AGGCCTCCCA GCCCCCATCG AGAAAACCAT
1081 CTCCAAAACC AAAGGGCAGC CCCGAGAACC ACAGGTGTAC ACCCTGCCCC CATCCCGGGA
1141 GGAGATGACC AAGAACCAGG TCAGCCTGAC CTGCCTGGTC AAAGGCTTCT ACCCCAGCGA
1201 CATCGCCGTG GAGTGGGAGA GCAATGGGCA GCCGGAGAAC AACTACAAGA CCACACCTCC
1261 CATGCTGGAC TCCGACGGCT CCTTCTTCCT CTACAGCAAG CTCACCGTGG ACAAGAGCAG
1321 GTGGCAGCAG GGGAACGTCT TCTCATGCTC CGTGATGCAT GAGGCTCTGC ACAACCACTA
1381 CACGCAGAAG AGCCTCTCCC TGTCTCCGGG TAAATGATAA GTCGAC  (SEQ ID NO: 1)
```

FIG. 1

```
  1 MEFGLSWLFL VAILKGVQCE VQLLESGGGL VQPGGSLRLS CAASGFTFSS YAMSWVRQAP
 61 GKGLEWVSGI TGSGGSTYYA DSVKGRFTIS RDNSKNTLYL QMNSLRAEDT AVYYCAKDPG
121 TTVIMSWFDP WGQGTLVTVS Sastkgpsvf plapcsrsts estaalgclv kdyfpepvtv
181 swnsgaltsg vhtfpavlqs sglyslssvv tvpssnfgtq tytcnvdhkp sntkvdktve
241 rkccvecppc pappvagpsv flfppkpkdt lmisrtpevt cvvvdvshed pevqfnwyvd
301 gvevhnaktk preeqfnstf rvvsvltvvh qdwlngkeyk ckvsnkglpa piektisktk
361 gqprepqvyt lppsreemtk nqvsltclvk gfypsdiave wesngqpenn ykttppmlds
421 dgsfflyskl tvdksrwqqg nvfscsvmhe alhnhytqks lslspgk (SEQ ID NO: 2)
```

FIG. 2

```
  1 TCTAGACCAC CATGGAAACC CCAGCGCAGC TTCTCTTCCT CCTGCTACTC TGGCTCCCAG
 61 ATACCACCGG AGAAATTGTG TTGACGCAGT CTCCAGGCAC CCTGTCTTTG TCTCCAGGGG
121 AAAGAGCCAC CCTCTCCTGT AGGGCCAGTC AGAGTGTTCG CGGCAGGTAC TTAGCCTGGT
181 ACCAGCAGAA ACCTGGCCAG GCTCCCAGGC TCCTCATCTA TGGTGCATCC AGCAGGGCCA
241 CTGGCATCCC AGACAGGTTC AGTGGCAGTG GGTCTGGGAC AGACTTCACT CTCACCATCA
301 GCAGACTGGA GCCTGAAGAT TTTGCAGTGT TTTACTGTCA GCAGTATGGT AGTTCACCTC
361 GGACGTTCGG CCAAGGGACC AAGGTGGAAA TCAAACGAAC TGTGGCTGCA CCATCTGTCT
421 TCATCTTCCC GCCATCTGAT GAGCAGTTGA AATCTGGAAC TGCCTCTGTT GTGTGCCTGC
481 TGAATAACTT CTATCCCAGA GAGGCCAAAG TACAGTGGAA GGTGGATAAC GCCCTCCAAT
541 CGGGTAACTC CCAGGAGAGT GTCACAGAGC AGGACAGCAA GGACAGCACC TACAGCCTCA
601 GCAGCACCCT GACGCTGAGC AAAGCAGACT ACGAGAAACA CAAAGTCTAC GCCTGCGAAG
661 TCACCCATCA GGGCCTGAGC TCGCCCGTCA CAAAGAGCTT CAACAGGGGA GAGTGTTGAT
721 AAGTCGAC (SEQ ID NO: 3)
```

FIG. 3

```
  1 METPAQLLFL LLLWLPDTTG EIVLTQSPGT LSLSPGERAT LSCRASQSVR
 51 GRYLAWYQQK PGQAPRLLIY GASSRATGIP DRFSGSGSGT DFTLTISRLE
101 PEDFAVFYCQ QYGSSPRTFG QGTKVEIKrt vaapsvfifp psdeqlksgt
151 asvvcllnnf ypreakvqwk vdnalqsgns qesvteqdsk dstyslsstl
201 tlskadyekh kvyacevthq glsspvtksf nrgec (SEQ ID NO: 4)
```

FIG. 6
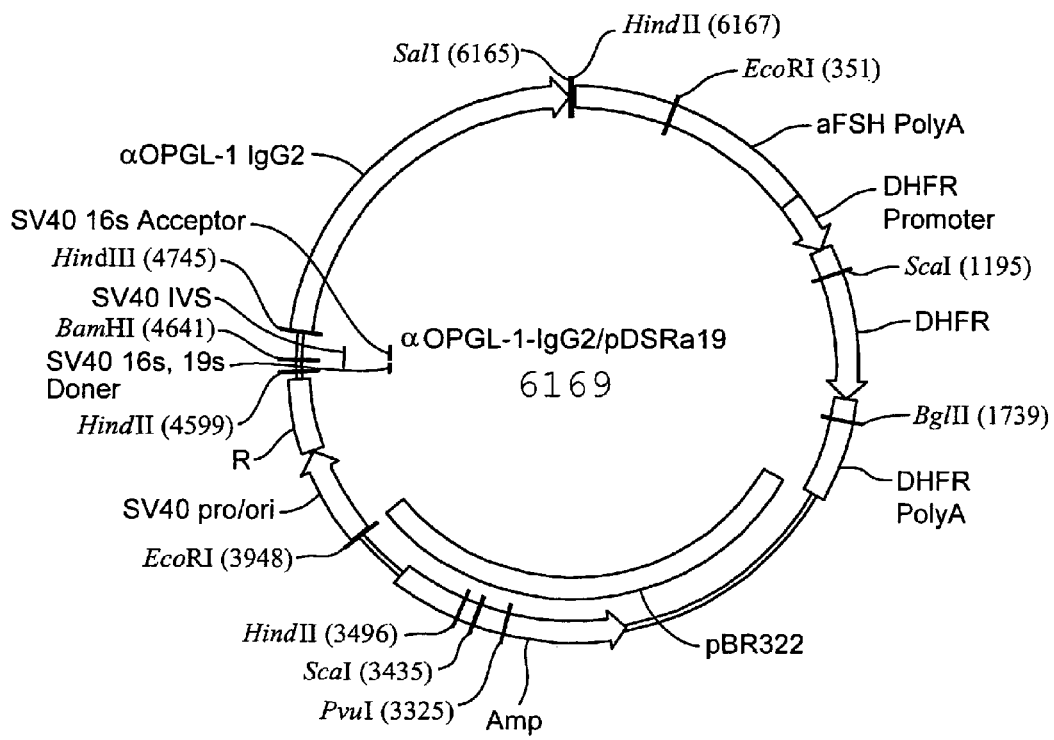
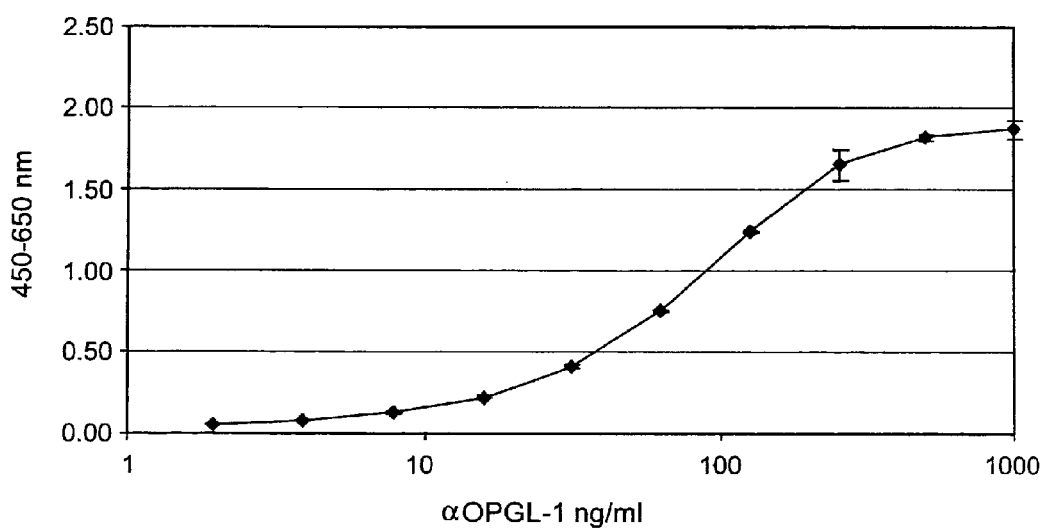
FIG. 7

```
  1 EVQLLESGGG LVQPGGSLRL SCAASGFTFS SYAMSWVRQA
 41 PGKGLEWVSG ITGSGGSTYY ADSVKGRFTI SRDNSKNTLY
 81 LQMNSLRAED TAVYYCAKDP GTTVIMSWFD PWGQGTLVTV
121 SS (SEQ ID NO: 13)
```

```
  1 EIVLTQSPGT LSLSPGERAT LSCRASQSVR GRYLAWYQQK
 41 PGQAPRLLIY GASSRATGIP DRFSGSGSGT DFTLTISRLE
 81 PEDFAVFYCQ QYGSSPRTFG QGTKVEIK (SEQ ID NO: 14)
```

US 8,058,418 B2

POLYNUCLEOTIDES ENCODING HEAVY AND LIGHT CHAINS OF ANTIBODIES TO OPGL

This application is a continuation of U.S. patent application Ser. No. 10/180,648, filed Jun. 25, 2002, now U.S. Pat. No. 7,364,736, which claims priority to U.S. Provisional Application No. 60/301,172, filed Jun. 26, 2001. U.S. patent application Ser. No. 10/180,648 and U.S. Provisional Application No. 60/301,172 are incorporated herein by reference for any purpose.

FIELD OF THE INVENTION

The present invention relates to antibodies that bind osteoprotegerin ligand (OPGL). Compositions and methods for the treatment of bone diseases, such as osteoporosis, bone loss from arthritis, Paget's disease, and osteopenia, are also described.

BACKGROUND OF THE INVENTION

Bone tissue provides support for the body and includes mineral (including calcium and phosphorous), a matrix of collagenous and noncollagenous proteins, and cells. Living bone tissue exhibits a dynamic equilibrium between formation of bone, which is called deposition, and break-down of bone, which is called resorption. Three types of cells found in bone, osteocytes, osteoblasts and osteoclasts, are involved in this equilibrium. Osteoblasts promote formation of bone tissue whereas osteoclasts are associated with resorption. Resorption, or the dissolution of bone matrix and mineral, is a fast and efficient process compared to bone formation and can release large amounts of mineral from bone. Osteoclasts are involved in the regulation of the normal remodeling of skeletal tissue and in resorption induced by hormones. For instance, resorption is stimulated by the secretion of parathyroid hormone in response to decreasing concentrations of calcium ion in extracellular fluids. In contrast, inhibition of resorption is a function of calcitonin. In addition, metabolites of vitamin D alter the responsiveness of bone to parathyroid hormone and calcitonin.

Osteoprotegerin ligand (OPGL), which is a member of the TNF family of cytokines, promotes formation of osteoclasts through binding to the receptor activator of NF-κB (RANK, also called osteoclast differentiation and activation receptor, or ODAR). Osteoprotegerin (OPG), on the other hand, inhibits the formation of osteoclasts by sequestering OPGL and preventing OPGL association with ODAR. Thus, the amount of OPGL associated with ODAR correlates with the equilibrium between bone deposition and resorption.

After skeletal maturity, the amount of bone in the skeleton reflects the balance (or imbalance) of bone formation and bone resorption. Peak bone mass occurs after skeletal maturity prior to the fourth decade. Between the fourth and fifth decades, the equilibrium shifts and bone resorption dominates. The inevitable decrease in bone mass with advancing years starts earlier in females than males and is distinctly accelerated after menopause in some females (principally those of Caucasian and Asian descent).

Osteopenia is a condition relating generally to any decrease in bone mass to below normal levels. Such a condition may arise from a decrease in the rate of bone synthesis or an increase in the rate of bone destruction or both. A common form of osteopenia is primary osteoporosis, also referred to as postmenopausal and senile osteoporosis. This form of osteoporosis is a consequence of the universal loss of bone with age and is often a result of increase in bone resorption with a normal rate of bone formation. Many white females in the United States develop symptomatic osteoporosis. A direct relationship exists between osteoporosis and the incidence of hip, femoral, neck and inter-trochanteric fracture in women 45 years and older. Elderly males may develop symptomatic osteoporosis between the ages of 50 and 70. Osteoporosis may, in certain instances, result from increased levels or activity of OPGL. Thus, it would be useful to have molecules that can regulate the activity of OPGL in osteoclastogenesis.

Several factors have been identified which may contribute to postmenopausal and senile osteoporosis. They include alteration in hormone levels accompanying aging and inadequate calcium consumption attributed to decreased intestinal absorption of calcium and other minerals. Certain treatments have included hormone therapy or dietary supplements in an attempt to retard the process. More recently, anti-resorptive agents such as bisphosphonates and selective estrogen receptor modifiers (SERMs) have emerged for the prevention and treatment of reduced bone mass. Thus, it may be useful to combine those treatments with molecules that can regulate the activity of OPGL in treating certain osteopenic disorders.

SUMMARY OF THE INVENTION

In certain embodiments, the invention provides for an antibody, comprising a heavy chain and a light chain, wherein the heavy chain comprises an amino acid sequence as set forth in SEQ ID NO: 2 or a fragment thereof, and the light chain comprises an amino acid sequence as set forth in SEQ ID NO: 4 or a fragment thereof.

In certain embodiments, the invention provides for an antibody, comprising a heavy chain and a light chain, wherein the heavy chain comprises a variable region comprising an amino acid sequence as set forth in SEQ ID NO: 13 or a fragment thereof, and wherein the light chain comprises a variable region comprising an amino acid sequence as set forth in SEQ ID NO: 14 or a fragment thereof.

In certain embodiments, the invention provides for an antibody comprising a heavy chain and a light chain, wherein the heavy chain comprises an amino acid sequence as set forth in SEQ ID NO: 2 or a fragment thereof.

In certain embodiments, the invention provides for an antibody comprising a heavy chain and a light chain, wherein the heavy chain comprises a variable region comprising an amino acid sequence as set forth in SEQ ID NO: 13 or a fragment thereof.

In certain embodiments, the invention provides for an antibody comprising a heavy chain and a light chain, wherein the light chain comprises an amino acid sequence as set forth in SEQ ID NO: 4 or a fragment thereof.

In certain embodiments, the invention provides for an antibody comprising a heavy chain and a light chain, wherein the light chain comprises a variable region comprising an amino acid sequence as set forth in SEQ ID NO: 14 or a fragment thereof.

In certain embodiments, the invention provides for an antibody, comprising a heavy chain and a light chain, (a) wherein the heavy chain comprises a first variable region, and wherein the first variable region comprises a sequence that has at least 90% identity to the amino acid sequence set forth in SEQ ID NO: 13, and (b) wherein the light chain comprises a second variable region, and wherein the second variable region comprises a sequence that has at least 90% identity to the amino acid sequence set forth in SEQ ID NO: 14, and (c) wherein the antibody interacts with an osteoprotegerin ligand (OPGL).

In certain embodiments, the first variable region comprises a sequence that has at least 95% identity to the amino acid sequence set forth in SEQ ID NO: 13, and the second variable region comprises a sequence that has at, least 95% identity to the amino acid sequence set forth in SEQ ID NO: 14.

In certain embodiments, the first variable region comprises a sequence that has at least 99% identity to the amino acid sequence set forth in SEQ ID NO: 13, and the second variable region comprises a sequence that has at least 99% identity to the amino acid sequence set forth in SEQ ID NO: 14.

In certain embodiments, the invention provides for a heavy chain, comprising an amino acid sequence as set forth in SEQ ID NO:2 or a fragment thereof. In certain embodiments, the invention provides for a heavy chain comprising a variable region and a constant region, wherein the variable region comprises an amino acid sequence as set forth in SEQ ID NO: 13 or a fragment thereof.

In certain embodiments, the invention provides for a light chain, comprising an amino acid sequence as set forth in SEQ ID NO:4 or a fragment thereof. In certain embodiments, the invention provides for a light chain comprising an amino acid sequence as set forth in SEQ ID NO: 14 or a fragment thereof.

In certain embodiments of the invention, single chain antibodies are provided. In certain embodiments of the invention, single chain Fv antibodies are provided. In certain embodiments of the invention, Fab antibodies are provided. In certain embodiments of the invention, Fab' antibodies are provided. In certain embodiments of the invention, (Fab')2 antibodies are provided.

In certain embodiments, a pharmaceutical composition comprising an antibody of the invention is provided. In certain embodiments, a pharmaceutical composition comprising a therapeutically effective amount of an antibody to OPGL is provided.

In certain embodiments, a pharmaceutical composition comprises an antibody to OPGL and at least one therapeutic agent selected from a bone morphogenic factor, transforming growth factor-β (TGF-β), an interleukin-1 (IL-1) inhibitor, IL-1ra, Kineret™, a TNFα inhibitor, a soluble TNFα receptor, Enbrel™, an anti-TNFα antibody, Remicade™, a D2E7 antibody, a parathyroid hormone, an analog of a parathyroid hormone, a parathyroid hormone related protein, an analog of a parathyroid hormone related protein, a prostaglandin, a bisphosphonate, an alendronate, fluoride, calcium, a non-steroidal anti-inflammatory drug (NSAID), a COX-2 inhibitor, Celebrex™, Vioxx™; an immunosuppressant, methotrexate, leflunomide, a serine protease inhibitor, a secretory leukocyte protease inhibitor (SLPI), an IL-6 inhibitor, an antibody to IL-6, an IL-8 inhibitor, an antibody to IL-8, an IL-18 inhibitor, an IL-18 binding protein, an IL-18 antibody, an Interleukin-1 converting enzyme (ICE) modulator, a fibroblast growth factor (FGF), an FGF modulator, a PAF antagonist, a keratinocyte growth factor (KGF), a KGF-related molecule, a KGF modulator; a matrix metalloproteinase (MMP) modulator, a nitric oxide synthase (NOS) modulator, a modulator of glucocorticoid receptor, a modulator of glutamate receptor, a modulator of lipopolysaccharide (LPS) levels, a noradrenaline, a noradrenaline mimetic, and a noradrenaline modulator.

In certain embodiments of the invention, a method of treating an osteopenic disorder is provided, comprising administering a pharmaceutically effective amount of an antibody. In certain embodiments, a method of treating an osteopenic disorder comprising administering a pharmaceutical composition is provided.

In certain embodiments, a method of treating an inflammatory condition with attendant bone loss in a patient comprising administering a pharmaceutical composition is provided.

In certain embodiments, a method of treating an autoimmune condition with attendant bone loss in a patient comprising administering a pharmaceutical composition is provided.

In certain embodiments, a method of treating rheumatoid arthritis in a patient, comprising administering a pharmaceutical composition of the invention is provided.

In certain embodiments of the invention, a method of detecting the level of OPGL in a biological sample is provided, comprising contacting the sample with an antibody.

BRIEF DESCRIPTION OF THE FIGURES

FIG. 1 shows a cDNA sequence encoding the αOPGL-1 antibody heavy chain (SEQ ID NO: 1). The DNA sequence of the heavy chain expression plasmid beginning at the HindIII site, through the SalI site, is shown. The start codon begins at nucleotide 14 and the stop codon begins at nucleotide 1415.

FIG. 2 shows the amino acid sequence of the αOPGL-1 antibody heavy chain (SEQ ID NO: 2). The IgG2 signal peptide is underlined, the variable region is in capital letters and is not underlined, and the constant region is in lower case letters.

FIG. 3 shows a cDNA sequence encoding the αOPGL-1 antibody light chain (SEQ ID NO: 3). The DNA sequence of the kappa chain expression plasmid beginning at the XbaI site, through the SalI site, is shown. The start codon begins at nucleotide 12 and the stop codon begins at nucleotide 717.

FIG. 6 shows a schematic diagram of the αOPGL-1 IgG2 heavy chain expression plasmid, αOPGL-1-IgG2/pDSRa19.

FIG. 7 shows dose-dependent binding of αOPGL-1 to OPGL-coated EIA plates. Ninety-six well EIA plates are coated with recombinant soluble OPGL. Varying concentrations of αOPGL-1 are added to the wells and incubated for about 2 hours at room temperature. Bound antibody is detected with goat anti-Human IgG (Fab')—Horse Radish Peroxidase. The absorbance is read at 450 nm and 650 nm.

DETAILED DESCRIPTION OF CERTAIN PREFERRED EMBODIMENTS

Figures 4, 5:
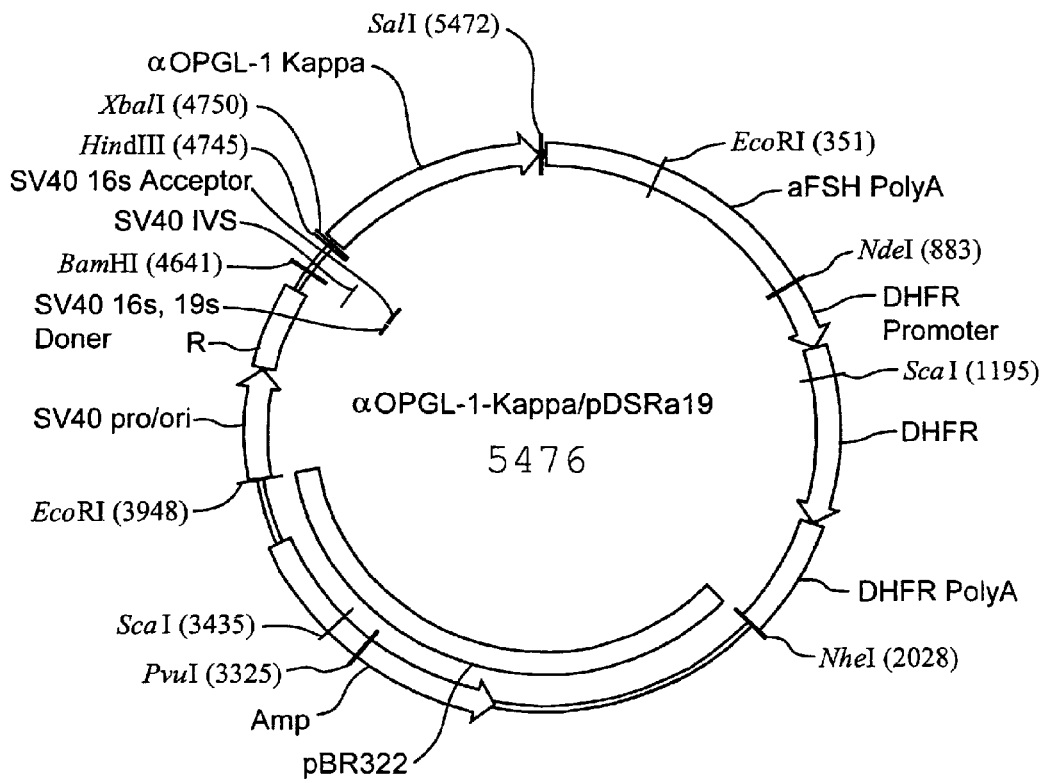
FIG. 4 shows the amino acid sequence of the αOPGL-1 antibody light chain (SEQ ID NO: 4). The kappa signal peptide is underlined, the variable region is in capital letters and is not underlined, and the constant region is in lower case letters.
FIG. 5 shows a schematic diagram of the αOPGL-1 kappa light chain expression plasmid αOPGL-1-Kappa/pDSRa19.

The section headings used herein are for organizational purposes only and are not to be construed as limiting the subject matter described. All references cited in this application are expressly incorporated by reference herein for any purpose.

Definitions

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

The term "isolated protein" referred to herein means a protein encoded by cDNA, recombinant RNA, or synthetic origin or some combination thereof, which (1) is free of at least some proteins with which it would normally be found, (2) is essentially free of other proteins from the same source, e.g., from the same species, (3) is expressed by a cell from a different species, or (4) does not occur in nature.

The term "polypeptide" is used herein as a generic term to refer to native proteins, or sequences that have deletions, additions, and/or substitutions of one or more amino acids of the native sequence. The term "polypeptide" also encompasses αOPGL-1 (as described below, SEQ ID NO: 2 and SEQ ID NO: 4), or sequences that have deletions, additions, and/or substitutions of one or more amino acid of αOPGL-1. According to certain embodiments, the invention comprises the human heavy chain immunoglobulin molecule represented by FIG. 2 (SEQ ID NO: 2) and the human light chain immunoglobulin molecule represented by FIG. 4 (SEQ ID NO: 4), or fragments or analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to components that are in a relationship permitting them to function in their intended manner. For example, a control sequence "operably linked" to a coding sequence is ligated in such a way that expression of the coding sequence is achieved under conditions compatible with the control sequences.

The term "control sequence" as used herein refers to polynucleotide sequences which may effect the expression and processing of coding sequences to which they are ligated. The nature of such control sequences may differ depending upon the host organism. According to certain embodiments, control sequences for prokaryotes may include promoter, ribosomal binding site, and transcription termination sequence. According to certain embodiments, control sequences for eukaryotes may include promoters and transcription termination sequence. In certain embodiments, "control sequences" can include leader sequences and/or fusion partner sequences.

The term "polynucleotide" as referred to herein means a polymeric form of nucleotides of at least 10 bases in length. In certain embodiments, the bases may be ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring, and/or non-naturally occurring oligonucleotide linkages. Oligonucleotides are a polynucleotide subset generally comprising a length of 200 bases or fewer. In certain embodiments, oligonucleotides are 10 to 60 bases in length. In certain embodiments, oligonucleotides are 12, 13, 14, 15, 16, 17, 18, 19, or 20 to 40 bases in length. Oligonucleotides may be single stranded or double stranded, e.g. for use in the construction of a gene mutant. Oligonucleotides of the invention may be sense or antisense oligonucleotides.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. Nucl. Acids Res. 14:9081 (1986); Stec et al. J. Am. Chem. Soc. 106:6077 (1984); Stein et al. Nucl. Acids Res. 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990), the disclosures of which are hereby incorporated by reference for any purpose. An oligonucleotide can include a label for detection.

Identity and similarity of related and polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure*, 5(3) (1978) for the PAM 250 comparison matrix; Henikoff et al., *Proc. Natl. Acad. Sci USA*, 89:10915-10919 (1992) for the BLOSUM 62 comparison matrix) is also used by the algorithm.

In certain embodiments, the parameters for a polypeptide sequence comparison include the following:

Algorithm: Needleman et al.; *J. Mol. Biol.*, 48:443-453 (1970);

Comparison matrix: BLOSUM 62 from Henikoff et al., supra (1992);

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3): 377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997)).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiocochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The term "polypeptide fragment" as used herein refers to a polypeptide that has an amino-terminal and/or carboxy-terminal deletion. In certain embodiments, fragments are at least 5 to 467 amino acids long. It will be appreciated that in certain embodiments, fragments are at least 5, 6, 8, 10, 14, 20, 50, 70, 100, 150, 200, 250, 300, 350, 400, or 450 amino acids long.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al. J. Med. Chem. 30:1229 (1987), which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference for any purpose); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. In certain embodiments, binding fragments are produced by recombinant DNA techniques. In certain embodiments, binding fragments are produced by enzymatic or chemical cleavage of intact antibodies. Binding fragments include, but are not limited to, Fab, Fab', F(ab')2, Fv, and single-chain antibodies.

The term "heavy chain" includes any polypeptide having sufficient variable region sequence to confer specificity for an OPGL. The term "light chain" includes any polypeptide having sufficient variable region sequence to confer specificity for an OPGL. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carbody-terminus. The term "heavy chain", as used herein, encompasses a full-length heavy chain and fragments thereof. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. A Fab fragment is comprised of one light chain and the $C_H1$ and variable regions of one heavy chain. The heavy chain of a Fab molecule cannot form a disulfide bond with another heavy chain molecule. A Fab' fragment contains one light chain and one heavy chain that contains more of the constant region, between the $C_H1$ and $C_H2$ domains, such that an interchain disulfide bond can be formed between two heavy chains to form a F(ab')2 molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain which forms an antigen-binding region. Single chain antibodies are discussed in detail in WO 88/01649 and U.S. Pat. Nos. 4,946,778 and 5,260,203.

A bivalent antibody other than a "multispecific" or "multifunctional" antibody, in certain embodiments, typically is understood to have each of its binding sites identical.

An antibody substantially inhibits adhesion of a ligand to a receptor when an excess of antibody reduces the quantity of receptor bound to counterreceptor by at least about 20%, 40%, 60%, 80%, 85%, or more (as measured in an in vitro competitive binding assay).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. In certain embodiments, an antibody is said to specifically bind an antigen when the dissociation constant is $\leq 1$ µM, in certain embodiments, when the dissociation constant is $\leq 100$ nM, and in certain embodiments, when the dissociation constant is $\leq 10$ nM.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and may be used. Examples of labels for polypeptides include, but are not limited to, the following: radioisotopes or radionuclides (e.g., 3 H, 14 C, 15 N. 35 S, 90 Y, 99 Tc, 111 In, 125 I, 131 I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "osteopenic disorder" includes, but is not limited to, osteoporosis, osteopenia, Paget's disease, lytic bone metastases, periodontitis, rheumatoid arthritis, and bone loss due to immobilization. In addition to these bone disorders, certain cancers are known to increase osteoclast activity and induce bone resorption, such as breast, prostate, and multiple myeloma. These cancers are now known to produce factors that result in the over-expression of OPGL in the bone, and lead to increased osteoclast numbers and activity.

The term "pharmaceutical agent or drug" as used herein refers to a chemical compound or composition capable of inducing a desired therapeutic effect when properly administered to a patient.

The term "modulator," as used herein, is a compound that changes or alters the activity or function of a molecule. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described, e.g., in WO01/83525.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (contaminant species cannot be detected in the composition by conventional detection methods) wherein the composition consists essentially of a single macromolecular species.

The term patient includes human and animal subjects.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Osteoprotegerin Ligand (OPGL), a member of the tumor necrosis factor (TNF) family of cytokines, is involved in the formation of osteoclasts. Increased osteoclast activity correlates with a number of osteopenic disorders, including post-menopausal osteoporosis, Paget's disease, lytic bone metastases, and rheumatoid arthritis. Therefore, a reduction in OPGL activity may result in a decrease in osteoclast activity and may reduce the severity of osteopenic disorders. According to certain embodiments of the invention, antibodies directed to OPGL may be used treat osteopenic disorders, including by not limited to, those mentioned above.

In certain embodiments of the present invention, there is provided a fully human monoclonal antibody against human osteoprotegerin ligand (OPGL). In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule and monoclonal antibody is also provided. In certain embodiments, purified human monoclonal antibody against human OPGL is provided.

The ability to clone and reconstruct megabase-sized human loci in yeast artificial chromosomes (YACs) and to introduce them into the mouse germline provides an approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide a source for production of fully human monoclonal antibodies (MAbs). In certain embodiments, fully human antibodies are expected to minimize the immunogenic and allergic responses intrinsic to mouse or mouse-derivatized Mabs, and thus, in certain embodiments, increase the efficacy and safety of the administered antibodies. In certain embodiments, fully human antibodies may be used in the treatment of chronic and recurring human diseases, such as osteoporosis, inflammation, autoimmunity, and cancer, which may involve repeated antibody administrations.

One can engineer mouse strains deficient in mouse antibody production with large fragments of the human Ig loci in anticipation that such mice would produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains may yield high affinity antibodies against any antigen of interest, including human antigens. Using the hybridoma technology, antigen-specific human MAbs with the desired specificity may be produced and selected.

In certain embodiments, one may use constant regions from species other than human along with the human variable region(s).

Naturally Occurring Antibody Structure

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that may be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

Bispecific or Bifunctional Antibodies

A bispecific or bifunctional antibody typically is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann Clin. Exp. Immunol. 79: 315-321 (1990), Kostelny et al. J. Immunol. 148:1547-1553 (1992).

Preparation of Antibodies

According to certain embodiments, certain antibodies specifically binding to OPGL are encompassed by the invention. In certain embodiments, the antibodies may be produced by immunization with full-length OPGL, soluble forms of OPGL, or a fragment thereof. In certain embodiments, the antibodies of the invention may be polyclonal or monoclonal, and/or may be recombinant antibodies. In certain embodiments, antibodies of the invention are human antibodies prepared, for example, by immunization of transgenic animals capable of producing human antibodies (see, for example, PCT Published Application No. WO 93/12227).

In certain embodiments, the complementarity determining regions (CDRs) of the light and heavy chain variable regions of αOPGL-1 may be grafted to framework regions (FRs) from the same, or another, species. In certain embodiments, the CDRs of the light and heavy chain variable regions of αOPGL-1 may be grafted to consensus human FRs. To create consensus human FRs, in certain embodiments, FRs from several human heavy chain or light chain amino acid sequences are aligned to identify a consensus amino acid sequence. In certain embodiments, the FRs of the αOPGL-1 heavy chain or light chain are replaced with the FRs from a different heavy chain or light chain. In certain embodiments, rare amino acids in the FRs of the heavy and light chains of αOPGL-1 are not replaced, while the rest of the FR amino acids are replaced. Rare amino acids are specific amino acids that are in positions in which they are not usually found in FRs. In certain embodiments, the grafted variable regions from αOPGL-1 may be used with a constant region that is different from the constant region of αOPGL-1. In certain embodiments, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

According to certain embodiments, antibodies of the invention are prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. Technologies utilized for achieving this result are disclosed in the patents, applications, and references disclosed in the specification, herein. In certain embodiments, one may employ methods such as those disclosed in PCT Published Application No. WO 98/24893, which is hereby incorporated by reference for any purpose. See also Mendez et al. Nature Genetics 15:146-156 (1997), which is hereby incorporated by reference for any purpose.

According to certain embodiments, fully human monoclonal antibodies specific for OPGL are produced as follows. Transgenic mice containing human immunoglobulin genes are immunized with the antigen of interest. Lymphatic cells (such as B-cells) from the mice that express antibodies are obtained. Such recovered cells are fused with a myeloid-type cell line to prepare immortal hybridoma cell lines, and such hybridoma cell lines are screened and selected to identify hybridoma cell lines that produce antibodies specific to the antigen of interest. In certain embodiments, the production of a hybridoma cell line that produces antibodies specific to OPGL is provided.

In certain embodiments, antibodies of the invention are produced by hybridoma lines AMG 6.1, AMG 6.4, AMG 6.5, AMG 7.1, and AMG 7.2. In certain embodiments, antibodies of the invention are produced by hybridoma lines AMG 6.1, AMG 6.4, and AMG 6.5. In certain embodiments, the antibodies of the invention bind to OPGL with a dissociation constant (Kd) of between approximately 0.23 and 0.29 nM. In certain embodiments of the invention, the antibodies bind to OPGL with a Kd of less than 0.23 nM.

In certain embodiments, the antibodies of the invention are of the IgG2 isotype. In certain embodiments of the invention, the antibodies comprise a human kappa light chain and a human IgG2 heavy chain. In certain embodiments, the antibodies of the invention have been cloned for expression in mammalian cells. In certain embodiments, the variable regions of the antibodies are ligated to a constant region other than the constant region for the IgG2 isotype.

In certain embodiments, conservative modifications to the heavy and light chains of αOPGL-1 (and corresponding modifications to the encoding nucleotides) will produce antibodies to OPGL having functional and chemical characteristics similar to those of αOPGL-1. In contrast, substantial modifications in the functional and/or chemical characteristics of αOPGL-1 may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of αOPGL-1, or to increase or decrease the affinity of the antibodies to OPGL described herein.

In certain embodiments, antibodies of the present invention can be expressed in cell lines other than hybridoma cell lines. In certain embodiments, sequences encoding particular antibodies can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used may depend upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include, but are not limited to, many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and produce antibodies with constitutive OPGL binding properties.

According to certain embodiments, antibodies of the invention are useful for detecting OPGL in biological samples. In certain embodiments, this allows the identification of cells or tissues which produce the protein. In certain embodiments, antibodies which bind to OPGL and block interaction with other binding compounds may have therapeutic use in modulating osteoclast differentiation and bone resorption. In certain embodiments, antibodies to OPGL may block OPGL binding to ODAR, which may result in a block in the signal transduction cascade and loss of NF-κB mediated transcription activation. Assays for measuring NF-κB-mediated transcription activation using, e.g., a luciferase reporter assay, are known to those skilled in the art.

In certain embodiments, methods are provided of treating a bone disorder comprising administering a therapeutically effective amount of an antibody to OPGL. In certain embodiments, methods are provided of treating a bone disorder comprising administering a therapeutically effective amount of an antibody to OPGL and another therapeutic agent. In certain such embodiments, the additional therapeutic agent is administered in a therapeutically effective amount. In certain embodiments, the bone disorder is a disorder characterized by a net bone loss, including but not limited to, osteopenia and osteolysis. In certain embodiments, treatment with an antibody to OPGL is used to suppress the rate of bone resorption. Therefore, in certain embodiments, treatment may be used to reduce the rate of bone resorption where the resorption rate is above normal, or to reduce bone resorption to below normal levels in order to compensate for below normal levels of bone formation. In certain embodiments, antibodies can be tested for binding to OPGL in the absence or presence of OPG and examined for their ability to inhibit OPGL-mediated osteoclastogenesis and/or bone resorption.

Conditions which may be treated according to certain embodiments include, but are not limited to, the following:

Osteoporosis, including, but not limited to, primary osteoporosis, endocrine osteoporosis (including, but not limited to, hyperthyroidism, hyperparathyroidism, Cushing's syndrome, and acromegaly), hereditary and congenital forms of osteoporosis (including, but not limited to, osteogenesis imperfecta, homocystinuria, Menkes' syndrome, Riley-Day syndrome), and osteoporosis due to immobilization of extremities;

Paget's disease of bone (osteitis deformans) in adults and juveniles;

Osteomyelitis, i.e., an infectious lesion in bone, leading to bone loss;

Hypercalcemia, including, but not limited to, hypercalcemia resulting from solid tumors (including, but not limited to, breast, lung and kidney) and hematologic malignacies (including, but not limited to, multiple myeloma, lymphoma and leukemia), idiopathic hypercalcemia, and hypercalcemia associated with hyperthyroidism and renal function disorders;

Osteopenia, including but not limited to, osteopenia following surgery, osteopenia induced by steroid administration, osteopenia associated with disorders of the small and large intestine, and osteopenia associated with chronic hepatic and renal diseases;

Osteonecrosis, i.e., bone cell death, including, but not limited to, osteonecrosis associated with traumatic injury, osteonecrosis associated with Gaucher's disease, osteonecrosis associated with sickle cell anemia, osteonecrosis associated with systemic lupus erythematosus, osteonecrosis associated with rheumatoid arthritis, osteonecrosis associated with periodontal disease, osteonecrosis associated with osteolytic metastasis, and osteonecrosis associated with other condition; and Loss of cartilage and joint erosion associated with rheumatoid arthritis.

In certain embodiments, an antibody to OPGL may be used alone or with at least one additional therapeutic agents for the treatment of bone disorders. In certain embodiments, an antibody to OPGL is used in conjunction with a therapeutically effective amount of an additional therapeutic agent. Exemplary therapeutic agents that may be administered with an antibody to OPGL include, but are not limited to, the bone morphogenic factors designated BMP-1 through BMP-12; transforming growth factor-β (TGF-β) and TGF-β family members; interleukin-1 (IL-1) inhibitors, including, but not limited to, IL-1ra and derivatives thereof and Kineret™; TNFα inhibitors, including, but not limited to, soluble TNFα receptors, Enbrel™, anti-TNFα antibodies, Remicade™, and D2E7 antibodies; parathyroid hormone and analogs thereof; parathyroid related protein and analogs thereof; E series prostaglandins; bisphosphonates (such as alendronate and others); bone-enhancing minerals such as fluoride and calcium; non-steroidal anti-inflammatory drugs (NSAIDs), including, but not limited to, COX-2 inhibitors, such as Celebrex™ and Vioxx™; immunosuppressants, such as methotrexate or leflunomide; serine protease inhibitors, including, but not limited to, secretory leukocyte protease inhibitor (SLPI); IL-6 inhibitors (including, but not limited to, antibodies to IL-6), IL-8 inhibitors (including, but not limited to, antibodies to IL-8); IL-18 inhibitors (including, but not limited to, IL-18 binding protein and IL-18 antibodies); Interleukin-1 converting enzyme (ICE) modulators; fibroblast growth factors FGF-1 to FGF-10 and FGF modulators; PAF antagonists; keratinocyte growth factor (KGF), KGF-related molecules, and KGF modulators; matrix metalloproteinase (MMP) modulators; Nitric oxide synthase (NOS) modulators, including, but not limited to, modulators of inducible NOS; modulators of glucocorticoid receptor; modulators of glutamate receptor; modulators of lipopolysaccharide (LPS) levels; and noradrenaline and modulators and mimetics thereof.

In certain embodiments, an antibody to OPGL is used with particular therapeutic agents to treat various inflammatory conditions, autoimmune conditions, or other conditions with attendant bone loss. In certain embodiments, in view of the condition and the desired level of treatment, two, three, or more agents may be administered. In certain embodiments, such agents may be provided together by inclusion in the same formulation. In certain embodiments, such agents and an antibody to OPGL may be provided together by inclusion in the same formulation. In certain embodiments, such agents may be provided together by inclusion in a treatment kit. In certain embodiments, such agents and an antibody to OPGL may be provided together by inclusion in a treatment kit. In certain embodiments, such agents may be provided separately. In certain embodiments, when administered by gene therapy, the genes encoding protein agents and/or an antibody to OPGL may be included in the same vector. In certain embodiments, the genes encoding protein agents and/or an antibody to OPGL may be under the control of the same promoter region. In certain embodiments, the genes encoding protein agents and/or an antibody to OPGL may be in separate vectors.

In certain embodiments, the present invention is directed to therapies comprising an antibody to OPGL and at least one interleukin-1 (IL-1) inhibitor, and methods of treatment using such therapies. In certain embodiments, a therapy comprises an antibody to OPGL and an IL-1 inhibitor and at least one additional molecule described herein. In certain embodiments, methods of treatment use IL-1 inhibitors and/or TNF-α inhibitors in conjunction with an antibody to OPGL. In certain embodiments, an antibody to OPGL in combination with IL-1 inhibitors and/or TNF-α inhibitors may be used for treatment of conditions such as asthma, rheumatoid arthritis, and multiple sclerosis.

Interleukin-1 (IL-1) is an anti-inflammatory cytokine. In certain instances, IL-1 is a mediator in many diseases and medical conditions. In certain instances, IL-1 is manufactured by cells of the macrophage/monocyte lineage. In certain instances, IL-1 is produced in two forms: IL-1 alpha (IL-1α) and IL-1 beta (IL-1β).

A disease or medical condition is considered to be an "interleukin-1 mediated disease" if the spontaneous or experimental disease or medical condition is associated with elevated levels of IL-1 in bodily fluids or tissue and/or if cells or tissues taken from the body produce elevated levels of IL-1 in culture. In certain embodiments, such interleukin-1 mediated diseases are also recognized by the following additional two conditions: (1) pathological findings associated with the disease or medical condition can be mimicked experimentally in animals by administration of IL-1 or upregulation of expression of IL-1; and (2) a pathology induced in experimental animal models of the disease or medical condition can be inhibited or abolished by treatment with agents that inhibit the action of IL-1. In certain embodiments, one or more of the above conditions are met in an IL-1-mediated disease. In certain embodiments, all three of the conditions are met in an IL-1-mediated disease.

Acute and chronic interleukin-1 (IL-1)-mediated diseases include, but are not limited to, the following: acute pancreatitis; amyotrophic lateral sclerosis (ALS, or Lou Gehrig's disease); Alzheimer's disease; cachexia/anorexia, including, but not limited to, AIDS-induced cachexia; asthma and other pulmonary diseases; atherosclerosis; autoimmune vasculitis; chronic fatigue syndrome; *Clostridium* associated illnesses, including, but not limited to, *Clostridium*-associated diarrhea; coronary conditions and indications, including, but not limited to, congestive heart failure, coronary restenosis, myocardial infarction, myocardial dysfunction (e.g., related to sepsis), and coronary artery bypass graft; cancer, including, but not limited to, leukemias, including, but not limited to, multiple myeloma leukemia and myelogenous (e.g., AML and CML), and tumor metastasis; diabetes (including, but not limited to, insulin-dependent diabetes); endometriosis; fever; fibromyalgia; glomerulonephritis; graft versus host disease and/or transplant rejection; hemohorragic shock; hyperalgesia; inflammatory bowel disease; inflammatory conditions of a joint, including, but not limited to, osteoarthritis, psoriatic arthritis, and rheumatoid arthritis; inflammatory eye disease, including, but not limited to, those associated with, for example, corneal transplant; ischemia, including, but not limited to, cerebral ischemia (including, but not limited to, brain injury as a result of, e.g., trauma, epilepsy, hemorrhage or stroke, each of which may lead to neurodegeneration); Kawasaki's disease; learning impairment; lung diseases (including, but not limited to, acute respiratory distress syndrome, or ARDS); multiple sclerosis; myopathies (e.g., muscle protein metabolism, including, but not limited to, muscle protein metabolism in sepsis); neurotoxicity (including, but not limited to, such condition induced by HIV); osteoporosis; pain, including, but not limited to, cancer-related pain; Parkinson's disease; periodontal disease; pre-term labor; psoriasis; reperfusion injury; septic shock; side effects from radiation therapy; temporal mandibular joint disease; sleep disturbance; uveitis; and an inflammatory condition resulting from, e.g., strain, sprain, cartilage damage, trauma, orthopedic surgery, infection, or other disease processes.

In certain embodiments, an IL-1 inhibitor may be any protein or molecule capable of specifically preventing activation of cellular receptors to IL-1, which may result from any number of mechanisms. Exemplary mechanisms include, but are not limited to, downregulating IL-1 production, binding free IL-1, interfering with IL-1 binding to its receptor, interfering with formation of the IL-1 receptor complex (i.e., association of IL-1 receptor with IL-1 receptor accessory protein), and interfering with modulation of IL-1 signaling after binding to its receptor.

Certain interleukin-1 inhibitors include, but are not limited to, IL-1 receptor antagonists, including, but not limited to, Kineret™, IL-1ra, IL-1ra variants, and IL-1ra derivatives, which are collectively termed "IL-1ra proteins;" anti-IL-1 receptor monoclonal antibodies (see, e.g., EP 623674, which is hereby incorporated by reference for any purpose); IL-1 binding proteins, including, but not limited to, soluble IL-1 receptors (see, e.g., U.S. Pat. Nos. 5,492,888, 5,488,032, 5,464,937, 5,319,071, and 5,180,812, which are hereby incorporated by reference for any purpose); anti-IL-1 monoclonal antibodies (see, e.g., WO 9501997, WO 9402627, WO 9006371, U.S. Pat. No. 4,935,343, EP 364778, EP 267611 and EP 220063, which are hereby incorporated by reference for any purpose); IL-1 receptor accessory proteins and antibodies thereto (see, e.g., WO 96/23067 and WO 99/37773, which are hereby incorporated by reference for any purpose); inhibitors of interleukin-1 beta converting enzyme (ICE) or caspase I (see, e.g., WO 99/46248, WO 99/47545, and WO 99/47154, which are hereby incorporated by reference for any purpose), which may be used to inhibit IL-1 beta production and secretion; interleukin-1 beta protease inhibitors; and other compounds and proteins that block in vivo synthesis or extracellular release of IL-1.

Exemplary IL-1 inhibitors are disclosed, e.g., in U.S. Pat. Nos. 5,747,444; 5,359,032; 5,608,035; 5,843,905; 5,359,032; 5,866,576; 5,869,660; 5,869,315; 5,872,095; 5,955,480; 5,965,564; International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, 99/36415; European (EP) patent applications 534978 and 894795; and French patent application FR 2762514. The disclosures of all of the aforementioned references are hereby incorporated by reference for any purpose.

Interleukin-1 receptor antagonist (IL-1ra) is a human protein that acts as a natural inhibitor of interleukin-1 and is a member of the IL-1 family, which includes IL-1α and IL-1β. Certain receptor antagonists, including IL-1 ra and variants and derivatives thereof, as well as methods of making and using them, are described in U.S. Pat. No. 5,075,222; WO 91/08285; WO 91/17184; AU 9173636; WO 92/16221; WO 93/21946; WO 94/06457; WO 94/21275; FR 2706772; WO 94/21235; DE 4219626, WO 94/20517; WO 96/22793; WO 97/28828; and WO 99/36541, which are incorporated herein by reference for any purpose. In certain embodiments, an IL-1 receptor antagonist may be glycosylated. In certain embodiments, an IL-1 receptor antagonist may be non-glycosylated.

Three forms of IL-1 ra and variants thereof are described in U.S. Pat. No. 5,075,222 (the '222 patent). The first form, called "IL-1i" in the '222 patent, is characterized as a 22-23 kD molecule on SDS-PAGE with an approximate isoelectric point of 4.8, which elutes from a Mono Q FPLC column at around 52 mM NaCl in Tris buffer, pH 7.6. The second form, IL-1 raβ, is characterized as a 22-23 kD protein, which elutes from a Mono Q column at 48 mM NaCl. Both IL-1 raα and IL-1 raβ are glycosylated. The third form, IL-1 rax, is characterized as a 20 kD protein, which elutes from a Mono Q column at 48 mM NaCl and is non-glycosylated. The '222 patent also describes certain methods for isolating genes that code for the inhibitors, cloning those genes in suitable vectors, transforming and transfecting those genes into certain cell types, and expressing those genes to produce the inhibitors.

In certain embodiments, deletions, insertions, and/or substitutions (individually or collectively referred to as "variant(s)") are made within the amino acid sequences of IL-1 ra. In certain embodiments, an IL-1 ra variant is biologically active (e.g., possesses the ability to inhibit IL-1).

In certain embodiments, the present invention is directed to therapies comprising an antibody to OPGL and at least one TNFα inhibitor, and methods of treatment using such therapies. In certain embodiments, a therapy comprises an antibody to OPGL and a TNFα inhibitor and at least one additional molecule described herein.

Certain diseases and medical conditions are mediated by TNF and may be categorized as inflammatory conditions. As used herein, a "TNF-mediated disease" includes, but is not limited to, a disease or medical condition that is associated with elevated levels of TNF in bodily fluids or tissue and/or in which cells or tissues taken from the body produce elevated levels of TNF in culture. In certain embodiments, a disease is a TNF-mediated disease if (1) pathological findings associated with the disease or medical condition can be mimicked experimentally in animals by the administration or upregulation of expression of TNF and/or (2) a pathology induced in experimental animal models of the disease or medical condition can be inhibited or abolished by treatment with agents that inhibit the action of TNF.

Certain acute and chronic TNF-mediated diseases include, but are not limited to: cachexia and anorexia; cancer, including, but not limited to, leukemia; chronic fatigue syndrome; coronary conditions and/or indications, including, but not limited to, congestive heart failure, coronary restenosis, myocardial infarction, myocardial dysfunction (including but not limited to, such condition related to sepsis), and coronary artery bypass graft; depression; diabetes, including, but not limited to, juvenile onset Type 1 diabetes, diabetes mellitus, and insulin resistance (including, but not limited to, insulin resistance associated with obesity); endometriosis, endometritis, and related conditions; fibromyalgia and analgesia; graft versus host rejection; hyperalgesia; inflammatory bowel diseases, including, but not limited to, Crohn's disease and *Clostridium difficile*-associated diarrhea; ischemia, including, but not limited to, cerebral ischemia, which includes, but is not limited to, brain injury as a result of trauma, epilepsy, hemorrhage, and/or stroke; lung disease, including, but not limited to, adult respiratory distress syndrome, asthma, and pulmonary fibrosis; multiple sclerosis; neuroinflammatory diseases; ocular diseases and conditions, including, but not limited to, corneal transplant, ocular degeneration and uveitis; pain, including, but not limited to, cancer-related pain; pancreatitis; periodontal diseases; Pityriasis rubra pilaris (PRP); prostatitis, including bacterial and non-bacterial prostatitis, and related conditions; psoriasis and related conditions; pulmonary fibrosis; reperfusion injury; rheumatic diseases, including, but not limited to, rheumatoid arthritis, osteoarthritis, juvenile arthritis (including, but not limited to, juvenile rheumatoid arthritis), seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced ("septic") arthritis, Sjögren's syndrome, rheumatic fever, polychondritis and polymyalgia rheumatica and giant cell arteritis); septic shock; side effects from radiation therapy; systemic lupus erythematosus (SLE); temporal mandibular joint disease; thyroiditis; and tissue transplantation and/or an inflammatory condition, e.g., resulting from strain, sprain, cartilage damage, trauma, orthopedic surgery, infection (e.g., HIV, *Clostridium difficile* and related species) or other disease process.

In certain embodiments, TNF inhibitors may act by at least one of downregulating or inhibiting TNF production, binding free TNF, interfering with TNF binding to its receptor, and interfering with modulation of TNF signaling after binding to its receptor. The term "TNF inhibitor" includes, but is not limited to, solubilized TNF receptors, including, but not limited to, soluble tumor necrosis factor receptor type I (sTNF-RI; also called the p55 receptor), soluble tumor necrosis factor receptor type II (also called the p75 receptor), and Enbrel™; antibodies to TNF, including, but not limited to, Remicade™ and D2E7 (see, e.g., U.S. Pat. Nos. 6,090,382 and 6,258,562); antibodies to TNF receptor; sTNF-RI (see, e.g., WO 98/24463), etanercept (Enbrel™), Avakine™; inhibitors of TNF-α converting enzyme (TACE); and other molecules that affect TNF activity.

Exemplary TNF-α inhibitors are described, e.g., in European patent applications EP 308 378; EP 422 339; EP 393 438; EP 398 327; EP 412 486; EP 418 014, EP 417 563, EP 433 900; EP 464 533; EP 512 528; EP 526 905; EP 568 928; EP 607 776, which describes the use of leflunomide for inhibition of TNF-α; EP 663 210; EP 542 795; EP 818 439; EP 664 128; EP 542 795; EP 741 707; EP 874 819; EP 882 714; EP 880 970; EP 648 783; EP 731 791; EP 895 988; EP 550 376; EP 882 714; EP 853 083; EP 550 376; EP 943 616; EP 939 121; EP 614 984; EP 853 083; U.S. Pat. Nos. 5,136,021; 5,929,117; 5,948,638; 5,807,862; 5,695,953; 5,834,435; 5,817,822; 5,830,742; 5,834,435; 5,851,556; 5,853,977; 5,359,037; 5,512,544; 5,695,953; 5,811,261; 5,633,145; 5,863,926; 5,866,616; 5,641,673; 5,869,677; 5,869,511; 5,872,146; 5,854,003; 5,856,161; 5,877,222; 5,877,200; 5,877,151; 5,886,010; 5,869,660; 5,859,207; 5,891,883; 5,877,180; 5,955,480; 5,955,476; 5,955,435; 5,994,351; 5,990,119; 5,952,320; 5,962,481; International patent applications WO 90/13575, WO 91/03553, WO 92/01002, WO 92/13095, WO 92/16221, WO 93/07863, WO 93/21946, WO 93/19777, WO 95/34326, WO 96/28546, WO 98/27298, WO 98/30541, WO 96/38150, WO 96/38150, WO 97/18207, WO 97/15561, WO 97/12902, WO 96/25861, WO 96/12735, WO 96/11209, WO 98/39326, WO 98/39316, WO 98/38859, WO 98/39315, WO 98/42659, WO 98/39329, WO 98/43959, WO 98/45268, WO 98/47863, WO 96/33172, WO 96/20926, WO 97/37974, WO 97/37973, WO 97/47599, WO 96/35711, WO 98/51665, WO 98/43946, WO 95/04045, WO 98/56377, WO 97/12244, WO 99/00364, WO 99/00363, WO 98/57936, WO 99/01449, WO 99/01139, WO 98/56788, WO 98/56756, WO 98/53842, WO 98/52948, WO 98/52937, WO 99/02510, WO 97/43250, WO 99/06410, WO 99/06042, WO 99/09022, WO 99/08688, WO 99/07679, WO 99/09965, WO 99/07704, WO 99/06041, WO 99/37818, WO 99/37625, WO 97/11668, WO 99/50238, WO 99/47672, WO 99/48491; Japanese patent applications 10147531, 10231285, 10259140, and 10130149, 10316570, 11001481, and 127,800/1991; German application no. 19731521; and British-application nos. 2 218 101, 2 326 881, 2 246 569. The disclosures of all of the aforementioned references are hereby incorporated by reference for any purpose.

EP 393 438 and EP 422 339 describe the amino acid and nucleic acid sequences of a soluble TNF receptor type I (also known as sTNFR-I or 30 kDa TNF inhibitor) and a soluble TNF receptor type II (also known as sTNFR-II or 40 kDa TNF inhibitor), which are collectively termed "sTNFRs". EP 393 438 and EP-422 339 also describe modified forms of sTNFR-I and sTNFR-II, including, but not limited to fragments, functional derivatives, and variants. Furthermore, EP 393 438 and EP 422 339 describe methods for isolating genes that code for the inhibitors, cloning the genes into suitable vectors, transforming or transfecting the genes into certain cell types, and expressing the genes to produce the inhibitors.

sTNFR-I and sTNFR-II are members of the nerve growth factor/TNF receptor superfamily of receptors, which includes the nerve growth factor receptor (NGF), the B cell antigen CD40, 4-1 BB, the rat T-cell antigen MRC OX40, the fas antigen, and the CD27 and CD30 antigens (Smith et al. (1990) *Science*, 248:1019-1023). A conserved feature of that group of cell surface receptors is a cysteine-rich extracellular ligand binding domain, which can be divided into four repeated motifs of about forty amino acids that contain 4-6 cysteine residues at positions that are well conserved (Smith et al. (1990), supra).

EP 393 438 teaches a 40 kDa TNF inhibitor Δ51 and a 40 kDa TNF inhibitor Δ53, which are truncated versions of the full-length recombinant 40 kDa TNF inhibitor protein. Δ51 and Δ53 have 51 or 53 amino acids, respectively, deleted from the carboxyl terminus of the mature protein.

Published PCT Application No. WO 98/01555 describes truncated forms of sTNFR-I and sTNFR-II that do not contain the fourth domain (amino acid residues $Thr^{127}$-$Asn^{161}$ of sTNFR-I and amino acid residues $Pro^{141}$-$Thr^{179}$ of sTNFR-II); a portion of the third domain (amino acid residues $Asn^{111}$-$Cys^{126}$ of sTNFR-I and amino acid residues $Pro^{123}$-$Lys^{140}$ of sTNFR-II); and, optionally, do not contain a portion of the first domain (amino acid residues $Asp^1$-$Cys^{19}$ of sTNFR-I and amino acid residues $Leu^1$-$Cys^{32}$ of sTNFR-II). In certain embodiments, the truncated sTNFRs include the proteins represented by the formula $R_1$-$[Cys^{19}$-$Cys^{103}]$-$R_2$ and $R_4$-$[Cys^{32}$-$Cys^{115}]$-$R_5$. These proteins are truncated forms of sTNFR-I and sTNFR-II, respectively.

As used herein, "$R_1$-$[Cys^{19}$-$Cys^{103}]$-$R_2$" represents one or more proteins wherein $[Cys^{19}$-$Cys^{103}]$ is residues 19 through 103 of sTNFR-I, the sequence of which is provided in FIG. 1 of WO 98/01555; wherein $R_1$ represents a methionylated or nonmethionylated amine group of $Cys^{19}$ or one or more amino-terminal amino acid residues selected from $Cys^{18}$ to $Asp^1$; and wherein $R_2$ represents a carboxy group of $Cys^{103}$ or one or more carboxy-terminal amino acid residues selected from Phe104 to $Leu^{110}$.

Exemplary truncated sTNFR-I's of the present invention include, but are not limited to, sTNFR-I 2.6D/C105, sTNFR-I 2.6D/C106, sTNFR-I 2.6D/N105, sTNFR-I 2.3D/d8, sTNFR-I 2.3D/d18, sTNFR-I 2.3D/d15, either methionylated or nonmethionylated, and variants and derivatives thereof. Certain exemplary truncated sTNFR-I's are described, e.g., in published PCT Application No. WO 98/01555.

Figure 8:
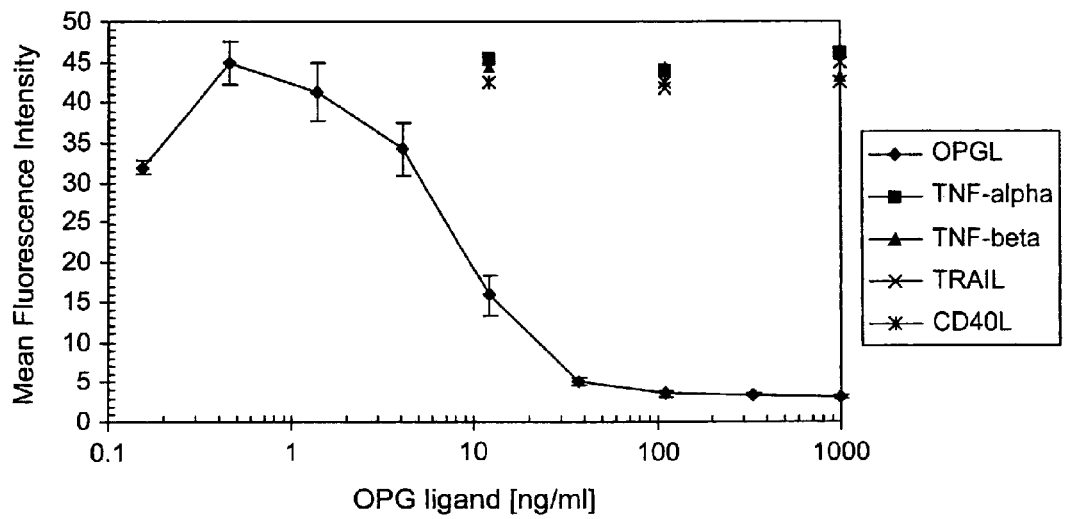
FIG. 8 shows specific binding of αOPGL-1 to membrane-bound OPGL. αOPGL-1 binds to OPGL expressed on a cell surface of transfected CHO REN 218-9 cells in a dose-dependent manner. This binding is competed by exogenously added human OPGL but not by TNF-α, TNF-β, TRAIL, or CD40 ligand. αOPGL-1 (100 ng/ml) is pre-incubated with varying concentrations of soluble OPGL or other ligands and is then incubated with CHO REN 218-9 cells expressing OPGL on the surface. Cells are then incubated for 30 minutes at 2-8° C. with FITC-labeled F(ab')$_2$ Goat anti-Human IgG, Fcγ Fragment Specific. After centrifugation and washing cell surface fluorescence is measured using flow cytometry.

As used herein, "$R_3$-$[Cys^{32}$-$Cys^{115}]$-$R_4$" represents one or more proteins wherein $[Cys^{32}$-$Cys^{115}]$ is residues $Cys^{32}$ through $Cys^{115}$ of sTNFR-II, the sequence of which is provided in FIG. 8 of WO 98/01555; wherein $R_3$ represents a methionylated or nonmethionylated amine group of $Cys^{32}$ or one or more amino-terminal amino acid residues selected from $Cys^{31}$ to $Leu^1$; and wherein $R_4$ represents a carboxy group of $Cys^{115}$ or one or more carboxy-terminal amino acid residues selected from $Ala^{116}$ to $Arg^{122}$.

In certain embodiments, the present invention is directed to therapies comprising an antibody to OPGL and at least one serine protease inhibitor, and methods of treatment using such therapies. In certain embodiments, a therapy comprises an antibody to OPGL and a serine protease inhibitor and at least one additional molecule described herein.

Endogenous proteolytic enzymes may degrade invading organisms, antigen-antibody complexes, and certain tissue proteins that are no longer necessary or useful. Infective agents may introduce additional proteolytic enzymes into the organism. Protease inhibitors may regulate both endogenous and invading proteolytic enzymes.

In certain embodiments, naturally occurring protease inhibitors serve to control endogenous proteases by limiting their reactions locally and temporally. In certain embodiments, protease inhibitors may inhibit proteases introduced into the body by infective agents. In certain instances, tissues that are particularly prone to proteolytic attack and infection, including, but not limited to, those of the respiratory tract, are rich in protease inhibitors.

Protease inhibitors comprise approximately 10% of the human plasma proteins. At least eight inhibitors have been isolated from this source and characterized in the literature. These include, but are not limited to, alpha 2-macroglobulin (alpha 2M), alpha 1-protease inhibitor (alpha 1PI), alpha 1-antichymotrypsin (alpha 1Achy), alpha 1-anticollagenase (alpha 1AC), and inter-alpha-trypsin inhibitor (1-alpha-1).

In certain instances, a disturbance of the protease/protease inhibitor balance can lead to protease-mediated tissue destruction, including, but not limited to, emphysema, arthritis, glomerulonephritis, periodontitis, muscular dystrophy, tumor invasion, and various other pathological conditions. In certain situations, e.g. severe pathological processes such as sepsis or acute leukemia, the amount of free proteolytic enzymes present may increase due to the release of enzyme from secretory cells.

Furthermore, in certain instances, a diminished regulating inhibitor capacity of the organism may also cause alterations in the protease/protease inhibitor balance. A nonlimiting example of such a diminished regulating inhibitor capacity is an alpha 1-protease inhibitor deficiency, which is correlated with the development of pulmonary emphysema.

In certain instances, serious damage to the organism can occur when such aberrant conditions are present unless measures can be taken to control the proteolytic enzymes. Therefore, protease inhibitors have been sought that can be administered to an organism to control proteolytic enzymes.

Leukocyte elastase, trypsin, cathepsin G, and pancreatic elastase are nonlimiting examples of a class of proteases known as serine proteases.

In certain instances, leukocyte elastase, when released extracellularly, degrades connective tissue and other valuable proteins. While a normally functioning organism degrades a certain amount of connective tissue and other proteins, the presence of an excessive amount of leukocyte elastase may be associated with various pathological states, including, but not limited to, emphysema and rheumatoid arthritis. In certain embodiments, to counteract the effects of leukocyte elastase when it is present in amounts greater than normal, a protease inhibitor has been sought which is specific for leukocyte elastase. Such a protease inhibitor may be useful if it were capable of being isolated or prepared in a purified form and in sufficient quantities to be pharmaceutically useful.

Certain leukocyte elastase inhibitors are described, e.g., in Schiessler et al., "Acid-Stable Inhibitors of Granulocyte Neutral Proteases in Human Mucous Secretions: Biochemistry and Possible Biological Function", in *Neutral Proteases of Human Polymorphoneuclear Leucocytes*, Havemann et al. (eds), Urban and Schwarzenberg, Inc. (1978), and in Travis and Salvesen, *Ann. Rev. Biochem.* 52: 655-709 (1983).

In certain instances, trypsin initiates degradation of certain soft organ tissue, such as pancreatic tissue, during a variety of acute conditions, including, but not limited to, pancreatitis. A trypsin inhibitor may be useful if it could be isolated and prepared in a purified form and in sufficient quantities to be pharmaceutically useful.

Cathepsin G is another protease present in leukocytes. In certain embodiments, cathepsin G is capable of degrading a variety of proteins in vitro, including those of the complement pathway. Pancreatic elastase is another protease that may have a role in pancreatitis. Thus, inhibitors for these proteases may also be of pharmaceutical value.

In certain embodiments, the substrate specificity and sensitivity to different inhibitors of serine proteases are believed to result from changes in only a few amino acid residues. By analogy, it may be possible to conceive of a class of serine protease inhibitors in which changes in a relatively few amino acids will result in inhibition of different proteases. In certain embodiments, a member of this class inhibits every serine protease.

An exemplary serine protease inhibitor is secretory leukocyte protease inhibitor (SLPI) and fragments and analogs thereof. Exemplary serine protease inhibitors also include, but are not limited to, anti-leukoprotease (ALP), mucous protease inhibitor (MPI), human seminal plasma inhibitor-I (HUSI-I), bronchial mucus inhibitor (BMI), and cervical mucus inhibitor (CUSI). In certain embodiments, a serine protease inhibitors also may be LPS modulator. See, e.g., Jin et al. (1997), *Cell* 88(3): 417-26. In certain embodiments, these molecules are well-suited for use in conditions leading to bone loss because they are preferentially directed to the cartilage.

Exemplary serine protease inhibitors are described, e.g., in U.S. Pat. Nos. 4,760,130; 5,900,400; and 5,633,227; which are herein incorporated by reference for any purpose. The molecules disclosed in the foregoing references as well as any variants or analogues thereof are collectively termed "serine protease inhibitors."

IL-18 is a pro-inflammatory cytokine that was found to induce interferon-γ and was previously named interferon gamma inducing factor (IGIF). In certain instances, IL-1 has been shown to upregulate IL-18 production, and IL-18 induces production of a number of proinflammatory cytokines, including IL-6 and MMP-1. See, e.g., Dinarello et al. (1998), *J. Leukocyte Biol.* 63: 658-64. In certain instances, caspase I is also important for IL-18 production. Experiments also suggest that TNF-α regulates IL-18 production, and that simultaneous inhibition of TNF-α and IL-18 protects against liver toxicity. See, e.g., Faggioni et al. (2000), *PNAS* 97: 2367-72.

IL-18 acts in vivo through a receptor system reminiscent of the IL-1 system. IL-18 interacts with a cell surface receptor (IL-18R), which interacts with an accessory protein (IL-18RAcP). IL-18-mediated signaling proceeds upon formation of the complex of IL-18, IL-18R, and IL-18RAcP. A natural inhibitor for IL-18 is IL-18 bp. In certain embodiments, IL-18 bp acts as a "decoy receptor" by binding to IL-18 molecules and preventing interaction with IL-18R.

In certain embodiments, the present invention is directed to therapies comprising an antibody to OPGL and at least one IL-18 inhibitor, and methods of treatment using such therapies. In certain embodiments, a therapy comprises an antibody to OPGL and an IL-18 inhibitor and at least one additional molecule described herein. Exemplary conditions that may be treated according to certain embodiments include, but are not limited to, inflammation, autoimmune diseases, IL-1 mediated diseases, and TNF-mediated diseases. Exemplary conditions that may be treated with an antibody to OPGL and at least one IL-18 inhibitor according to certain embodiments include, but are not limited to, arthritis, including, but not limited to rheumatoid arthritis; systemic lupus erythematosus (SLE); graft versus host disease (GvHD); hepatitis; sepsis; and the loss of bone and cartilage accompanying these diseases.

Exemplary IL-18 inhibitors include, but are not limited to, antibodies that bind to IL-18; antibodies that bind to IL-18R; antibodies that bind to IL-18RAcP; IL-18 bp; IL-18R fragments (e.g., a solubilized extracellular domain of the IL-18 receptor); peptides that bind to IL-18 and reduce or prevent its interaction with IL-18R; peptides that bind to IL-18R and reduce or prevent its interaction with IL-18 or with IL-18RAcP; peptides that bind to IL-18RAcP and reduce or prevent its interaction with IL-18R; and small molecules that reduce or prevent IL-18 production or the interaction between any of IL-18, IL-18R, and IL-18RAcP.

Certain IL-18 inhibitors are described, e.g., in U.S. Pat. No. 5,912,324, issued Jul. 14, 1994; EP 0 962 531, published Dec. 8, 1999; EP 712 931, published Nov. 15, 1994; U.S. Pat. No. 5,914,253, issued Jul. 14, 1994; WO 97/24441, published Jul. 10, 1997; U.S. Pat. No. 6,060,283, issued May 9, 2000; EP 850 952, published Dec. 26, 1996; EP 864 585, published Sep. 16, 1998; WO 98/41232, published Sep. 24, 1998; U.S. Pat. No. 6,054,487, issued Apr. 25, 2000; WO 99/09063, published Aug. 14, 1997; WO 99/22760, published Nov. 3, 1997; WO 99/37772, published Jan. 23, 1998; WO 99/37773, published Mar. 20, 1998; EP 0 974 600, published Jan. 26., 2000; WO 00/12555, published Mar. 9, 2000; Japanese patent application JP 111,399/94, published Oct. 31, 1997; Israel patent application IL 121554 A0, published Feb. 8, 1998; which are incorporated herein by reference for any purpose.

In certain embodiments, an antibody to OPGL may be used with at least one therapeutic agent for inflammation. In certain embodiments, an antibody to OPGL may be used with at least one therapeutic agent for an immune disorder. Exemplary therapeutic agents for inflammation and immune disorders include, but are not limited to, corticosteroids, including, but not limited to, prednisolone; nonsterdidal anti-inflammatory drugs (NSAIDs), including, but not limited to, cyclooxygenase type 1 (COX-1) and cyclooxygenase type 2 (COX-2) inhibitors; disease modifying antirheumatic drugs (DMARDs), including, but not limited to, methotrexate, hydroxychloroquine, chloroquine, cyclosporine, gold compounds (such as auranofin, aurothiomalate and aurothioglucose), and leflunomide; type IV phosophodiesterase inhibitors, including, but not limited to, Rolipram and Pentoxifylline; Tacrolimus (FK-506); Sirolimus (rapamycin); mycophenolic acid; 5-lipoxygenase inhibitors, including, but not limited to, Zileuton; modulators of interleukin-6 (IL-6); small molecule modulators of 38 kDa mitogen-activated protein kinase (p38-MAPK); small molecule modulators of intracellular molecules involved in inflammation pathways, wherein such intracellular molecules include, but are not limited to, jnk, IKK, NF-κB, ZAP70, and Ick. Certain exemplary therapeutic agents for inflammation are described, e.g., in C. A. Dinarello and L. L. Moldawer *Proinflammatory and Anti-Inflammatory Cytokines in Rheumatoid Arthritis: A Primer for Clinicians* Third Edition (2001) Amgen Inc. Thousand Oaks, Calif. Certain exemplary therapeutic agents for inflammation and autoimmune diseases include, but are not limited to, interferon gamma (IFN-γ) modulators; modulators of OX40/OX40L (including soluble forms of OX40); modulators of 4-1BB/4-1BB ligand (including soluble forms of 4-1BB); and modulators of B cell-T cell costimulatory pathways, including, but not limited to, modulators of the receptor ligand pairs CD28/B7, CD40/CD40L, ICOS/B7RP1, and AGP-3/TACI/BAFFR (AGP-3 binds to both TACI and BAFFR receptors). Certain exemplary modulators of B cell-T cell costimulatory pathways include, but are not limited to, inhibitors of CD28, B7.1, and B7.2 (including soluble forms of B7.1 or B7.2 and soluble forms of CTLA4, both of which may be fused to a heterologous peptide or protein which reduces or prevents degradation and/or increases half-life, reduces toxicity, reduces immunogenicity, or increases biological activity of a therapeutic protein by increasing solubility or circulating half-life); inhibitors of CD40 and CD40L (including soluble forms of CD40 which may be fused to a heterologous peptide or protein); inhibitors of ICOS and B7RP1 (including soluble forms of ICOS which may be fused to a heterologous peptide or protein) and inhibitors of AGP-3, TACI and BAFFR (including soluble forms of TACI and BAFFR). ICOS, B7RP1 and inhibitors thereof are described, e.g., in WO00/46240. AGP-3, TACI and BAFFR and inhibitors thereof are described, e.g., in WO00/47740, WO01/85872, WO02/15273, WO98/39361, and von Bulow and Bram (1997) *Science* 278:138-140.

In certain embodiments, an antibody to OPGL is used to treat bone loss, including, but not limited to, bone loss resulting from osteolytic destruction of bone caused by malignant or metastatic tumors. In certain embodiments, an antibody to OPGL may be used to treat bone loss associated with cancer. Exemplary cancers include, but are not limited to, breast, prostate, thyroid, kidney, lung, esophogeal, rectal, bladder, cervical, ovarian, and liver cancers, as well as cancer of the gastrointestinal tract. In certain embodiments, an antibody to OPGL may be used to treat bone loss associated with, e.g., certain hematological malignancies, including, but not limited to, multiple myeloma and lymphoma, including Hodgkin's Disease.

In certain embodiments, an antibody to OPGL is administered alone. In certain embodiments, an antibody to OPGL is administered with at least one other therapeutic agent, including, but not limited to, at least one other cancer therapy agent. Exemplary cancer therapy agents include, but are not limited to, radiation therapy and chemotherapy. In certain embodiments, chemotherapy may involve treatment with one or more of the following: anthracyclines, taxol, tamoxifene, doxorubicin, 5-fluorouracil, and other drugs known in the art. In certain embodiments, a cancer therapy agent is a luteinizing hormone-releasing hormone (LHRH) antagonist. In certain embodiments, a LHRH antagonist is a peptide antagonist.

In certain embodiments, an LHRH antagonist comprises the peptide: Ac-D-NaI-4-Cl-Phe-D-Pal-Ser-N-Me-Tyr-D-Asn-Leu-Lys(iPr)-Pro-D-Ala-NH2 (SEQ ID NO: 20), where NaI is 3-(2-napthyl)alaninyl; 4-Cl-Phe is (4'-chlorophenyl)alaninyl; Pal is 3-(3'-pyridyl)alaninyl; and Lys(iPr) is N-epsilon-2-propyl-lysinyl.

In certain embodiments, an LHRH antagonist is an LHRH antagonist decapeptide. Certain exemplary decapeptides are described, e.g., in U.S. Pat. No. 5,843,901, which is herein incorporated by reference for any purpose.

Exemplary therapeutic antibodies according to certain embodiments include, but are not limited to, mouse, mouse-human chimeric, CDR-grafted, humanized and fully human antibodies, and synthetic antibodies, including, but not limited to, those selected by screening antibody libraries. Exemplary antibodies include, but are not limited to, those which bind to cell surface proteins Her2, CDC20, CDC33, mucin-like glycoprotein, and epidermal growth factor receptor (EGFR) present on tumor cells, and optionally induce a cytostatic and/or cytotoxic effect on tumor cells displaying these proteins. Exemplary antibodies also include HERCEPTIN™ (trastuzumab), which may be used to treat breast cancer and other forms of cancer, and RITUXAN™ (rituximab), ZEVA-LIN™ (ibritumomab tiuxetan), and LYMPHOCIDE™ (epratuzumab), which may be used to treat non-Hodgkin's lymphoma and other forms of cancer. Certain exemplary antibodies also include ERBITUX™ (IMC-C225), BEXXAR™ (iodine 131 tositumomab), and Campath.

In certain embodiments, cancer therapy agents are polypeptides which selectively induce apoptosis in tumor cells, including, but not limited to, the TNF-related polypeptide TRAIL. In certain embodiments, an antibody to OPGL may be administered at least one of prior to, concurrent with, and subsequent to treatment with a cancer therapy agent. In certain embodiments, an antibody to OPGL may be administered prophylactically to prevent or mitigate the onset of bone loss by metastatic cancer. In certain embodiments, an antibody to OPGL may be administered for the treatment of an existing condition of bone loss due to metastasis.

In certain embodiments, an antibody to OPGL may be used to prevent and/or treat bone loss associated with multiple myeloma and/or to prevent and/or treat the disease itself. Multiple myeloma is a B cell derived tumor that may result in significant morbidity and/or mortality. In certain instances, a clinical manifestation of multiple myeloma is focal bone loss, which may be due to increased osteoclast activation in localized regions. Many myeloma patients present with bone lesions visible by radiological analysis and suffer from skeletal pain. In certain instances, patients with myeloma are susceptible to pathological fractures of involved bone, which may occur either spontaneously or due to injury. In certain instances, the skeletal lesions that occur during myeloma not only lead to bone fractures, but also deformity and occasionally nerve compression, particularly in the vertebral spine. In some patients, a pathological increase in serum calcium (hypercalcemia) occurs, and may cause significant problems during disease treatment. In certain embodiments, an antibody to OPGL may be administered to patients to reduce or block bone resorption and release of calcium, which may reduce the risk of fractures and spinal deformity.

In certain instances, myeloma cells do not directly participate in bone destruction, but instead produce extracellular signals that lead to osteoclast differentiation and activation. In certain instances, osteoclasts produce high levels of the cytokine IL-6, particularly when they become activated. IL-6 is a B-cell growth factor, and contributes to the growth of both murine and human myeloma cells in vitro. Myeloma cells may also either directly or indirectly produce OPGL, which may result in local bone lysis surrounding the myeloma cells embedded in bone marrow spaces. In certain instances, the normal osteoclasts adjacent to the myeloma cell in turn produce IL-6, which may lead to local expansion of the tumor cells. Myeloma cells expand in a clonal fashion and may occupy bone spaces that are created by inappropriate bone resorption.

It has been observed that OPG administration in rodents induces rapid death of the osteoclast population (see, e.g., Lacey et al. (2000) *Am. J. Pathol.* 157:435-448). A reduction in the number of osteoclasts may counteract the effect of increased IL-6 production by those cells and may therefore affect the growth and survival of myeloma cells within trabecular bone. Thus, in certain embodiments, administration of an antibody to OPGL to a myeloma patient may not only block the hyper resorption of bone, but may also affect the expansion and survival of the tumor itself.

B-cells express the receptor for OPGL, ODAR. Myeloma cells also express ODAR, and in addition may produce OPGL. In certain instances, the expression of both OPGL and ODAR in the same cell population may create an autocrine stimulus that affects survival of the myeloma cell. Thus, in certain embodiments, administration of an antibody to OPGL may reduce tumor cell survival, thereby decreasing or eliminating the tumor burden seen in myeloma patients.

In certain embodiments, the invention provides for pharmaceutical compositions comprising a therapeutically effective amount of an antibody to OPGL together with a pharmaceutically acceptable diluent, carrier, solubilizer, emulsifier; preservative and/or adjuvant.

In certain embodiments, the invention provides for pharmaceutical compositions comprising a therapeutically effective amount of an antibody to OPGL and a therapeutically effective amount of at least one additional therapeutic agents, together with a pharmaceutically acceptable diluent, carrier, solubilizer, emulsifier, preservative and/or adjuvant. In certain embodiments, the at least one additional therapeutic agent is selected from bone morphogenic factors designated BMP-1 through BMP-12; transforming growth factor-β (TGF-β) and TGF-β family members; interleukin-1 (IL-1) inhibitors, including, but not limited to, IL-1ra and derivatives thereof and Kineret™; TNFα inhibitors, including, but not limited to, a soluble TNFα receptor, Enbrel™, anti-TNFα antibodies, Remicade™, and D2E7 antibody; parathyroid hormone and analogs thereof, parathyroid related protein and analogs thereof; E series prostaglandins; bisphosphonates (such as alendronate and others); bone-enhancing minerals such as fluoride and calcium; non-steroidal anti-inflammatory drugs (NSAIDs), including COX-2 inhibitors, such as Celebrex™ and Vioxx™; immunosuppressants, such as methotrexate or leflunomide; serine protease inhibitors such as secretory leukocyte protease inhibitor (SLPI); IL-6 inhibitors (e.g., antibodies to IL-6), IL-8 inhibitors (e.g., antibodies to IL-8); IL-18-inhibitors (e.g., IL-18 binding protein or IL-18 antibodies); Interleukin-1 converting enzyme (ICE) modulators; fibroblast growth factors FGF-1 to FGF-10 and FGF modulators; PAF antagonists; keratinocyte growth factor (KGF), KGF-related molecules, or KGF modulators; matrix metalloproteinase (MMP) modulators; Nitric oxide synthase (NOS) modulators, including modulators of inducible NOS; modulators of glucocorticoid receptor; modulators of glutamate receptor; modulators of lipopolysaccharide (LPS) levels; and noradrenaline and modulators and mimetics thereof.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Edition, A. R. Gennaro, ed., Mack Publishing Company (1990).

In certain embodiments, an antibody to OPGL and/or a therapeutic molecule is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a composition comprising an antibody to OPGL, with or without at least one additional therapeutic agents, may be prepared for storage by mixing the selected composition having the desired degree of purity with optional formulation agents (*Remington's Pharmaceutical Sciences*, supra) in the form of a lyophilized cake or an aqueous solution. Further, in certain embodiments, a composition comprising an antibody to OPGL, with or without at least one additional therapeutic agents, may be formulated as a lyophilizate using appropriate excipients such as sucrose.

In certain embodiments, the pharmaceutical compositions of the invention can be selected for parenteral delivery. In certain embodiments, the compositions may be selected for inhalation or for delivery through the digestive tract, such as orally. The preparation of such pharmaceutically acceptable compositions is within the skill of the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition may be in the form of a pyrogen-free, parenterally acceptable aqueous solution comprising the desired antibody to OPGL, with or without additional therapeutic agents, in a pharmaceutically acceptable vehicle. In certain embodiments, a vehicle for parenteral injection is sterile distilled water in which the antibody to OPGL, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, an antibody to OPGL, with or without at least one additional therapeutic agent, may be formulated as a dry powder for inhalation. In certain embodiments, an inhalation solution comprising an antibody to OPGL, with or without at least one additional therapeutic agent, may be formulated with a propellant for aerosol delivery. In certain embodiments, solutions may be nebulized. Pulmonary administration is further described in PCT application no. PCT/US94/001875, which describes pulmonary delivery of chemically modified proteins.

In certain embodiments, it is contemplated that formulations may be administered orally. In certain embodiments, an antibody to OPGL, with or without at least one additional therapeutic agents, that is administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of the antibody to OPGL and/or any additional therapeutic agents. In certain embodiments, diluents, flavorings, low melting point waxes, vegetable oils, lubricants, suspending agents, tablet disintegrating agents, and binders may also be employed.

In certain embodiments, a pharmaceutical composition may involve an effective quantity of antibodies to OPGL, with or without at least one additional therapeutic agents, in a mixture with non-toxic excipients which are suitable for the manufacture of tablets. In certain embodiments, by dissolving the tablets in sterile water, or another appropriate vehicle, solutions may be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving antibodies to OPGL, with or without at least one additional therapeutic agents, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (U.S. Pat. No. 3,773,919 and EP 058,481), copolymers of L-glutamic acid and gamma ethyl-L-glutamate (Sidman et al., *Biopolymers*, 22:547-556 (1983)), poly(2-hydroxyethyl-methacrylate) (Langer et al., *J. Biomed. Mater. Res.*, 15:167-277 (1981) and Langer, *Chem. Tech.*, 12:98-105 (1982)), ethylene vinyl acetate (Langer et al., supra) or poly-D(−)-3-hydroxybutyric acid (EP 133,988). In certain embodiments, sustained release compositions may also include liposomes, which can be prepared by any of several methods known in the art. See e.g., Eppstein et al., *Proc. Natl. Acad. Sci. USA*, 82:3688-3692 (1985); EP 036,676; EP 088,046 and EP 143,949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally, are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, the present invention is directed to kits for producing a single-dose administration unit. In certain embodiments, the kits may each contain both a first container having a dried protein and a second container having an aqueous formulation. In certain embodiments of this invention, kits containing single and multi-chambered pre-filled syringes (e.g., liquid syringes and lyosyringes) are included.

In certain embodiments, the effective amount of a pharmaceutical composition comprising an antibody to OPGL, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the antibody to OPGL, with or without at least one additional therapeutic agent, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of the antibody to OPGL and/or any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising an antibody to OPGL, with or without at least one additional therapeutic agent, in an ex vivo manner. In such instances, cells, tissues and/or organs that have been removed from the patient are exposed to a pharmaceutical composition comprising an antibody to OPGL, with or without at least one additional therapeutic agent, after which the cells, tissues and/or organs are subsequently implanted back into the patient.

In certain embodiments, an antibody to OPGL and/or any additional therapeutic agents can be delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the present invention.

Example 1

Cloning the αOPGL-1 Heavy and Light Chains

CHO cells expressing the full-length human OPGL cDNA are used to immunize transgenic mice containing human immunoglobulin genes. Lymph nodes from the immunized mice are fused to murine myeloma cells to generate hybridomas. Supernatants from the hybridoma lines are tested in an ELISA assay for antibodies that react with human OPGL. Anti-OPGL expressing hybridoma lines AMG 6.5, AMG 6.4, and AMG 6.1 are found to express antibodies with high affinity for OPGL (Kd's of 0.28 nM, 0.29 nM, and 0.23 nM, respectively), and AMG 6.5 is selected for cloning. Heavy and light chain cDNA clones from AMG 6.5 and AMG 6.4 are identical, and AMG 6.5 is used to clone the αOPGL-1 light chain cDNA, while AMG 6.4 is used to clone the αOPGL-1 heavy chain cDNA.

Cloning of the αOPGL-1 Light Chain

The αOPGL-1 kappa light chain variable region is obtained using PCR amplification methods from first strand cDNA prepared from AMG 6.5 total RNA. First strand cDNA is prepared from AMG 6.5 total RNA using a random primer with an extended 5'-adapter (5'-GGCCGGATAGGCCT-CACNNNNNNT-3' (SEQ ID NO: 15)) and the materials and methods provided by the Gibco SuperScript II™ Preamplification System for First Strand cDNA Synthesis kit (cat. no. 18089-011). The oligonucleotides below are used for the PCR:

5' kappa RACE primer:

```
                                          (SEQ ID NO: 5)
     5'-GAT GAC CCA GTC TCC AGC CAC CCT G-3'
```

3' kappa RACE primer:

```
                                          (SEQ ID NO: 6)
     5'-AAG GGT CAG AGG CCA AAG GAT GG-3'
```

The amplified DNAs are cloned into pCRII-TOPO (Invitrogen) and the resulting plasmids are sequenced. The kappa chain consensus sequence is used to design primers for PCR amplification of the full-length αOPGL-1 kappa chain. The 5' αOPGL-1 kappa primer incorporates a XbaI site (TCTAGA) for cloning and a "CCACC" Kozak sequence before the initiator Met codon. The 3' αOPGL-1 kappa primer incorporates a SalI site (GTCGAC) following the stop codon for cloning.

5' αOPGL-1 kappa primer:

```
5'-CAA CTC TAG A CC ACC ATG GAA ACC CCA GCG-3'   (SEQ ID NO: 7)

XbaI Site Kozak   M   E   T   P   A         (SEQ ID NO: 16)
```

3' αOPGL-1 kappa primer:

```
5'-TTT GAC GTC GAC TTA TCA ACA CTC TCC CCT GTT GAA G-3'   (SEQ ID NO: 8)
         SalI Site*   *   C   E   G   R   N   F           (SEQ ID NO: 17)
```

The full-length αOPGL-1 kappa chain cDNA clone is obtained using the AMG 6.5 first strand cDNA, described above, by PCR amplification with the 5' and 3' αOPGL-1 kappa primers. The PCR reaction generates a 738 bp fragment encoding the 235 amino acid residues (including the 20 amino acid kappa chain signal sequence) of the αOPGL-1 kappa chain (FIG. 4, SEQ ID NO: 4). Following purification using a QIAquick PCR Purification kit (Qiagen cat. no. 28104), this fragment is used to construct the kappa light chain expression vector.

The 738 bp full-length kappa fragment generated above is cut with XbaI and SalI, is purified using the Promega Wizard DNA Clean-Up System (Promega cat. no. A7100), and is cloned into pDSRα19 to generate plasmid αOPGL-1-kappa/pDSRα19 (FIG. 5). pDSRα2 has been described previously (see WO 90/14363, which is herein incorporated by reference for any purpose (see, e.g., FIG. 12)). Briefly, to make pDSRα19, pDSRα2 is modified in the following ways: the FSH polyA is shortened by approximately 1400 base pairs, to 885 base pairs, and now ends at the NdeI site; the dihydrofolate reductase (DHFR) promoter now contains 209 base pairs, having been shortened from the 5' end by approximately 1 kilobase; and an approximately 550 base pair BglII fragment from the DHFR polyA sequence is deleted.

The αOPGL-1 kappa light chain expression clone is sequenced to confirm that it coded for the same peptide that is identified in the AMG 6.5 hybridoma. The final expression vector, αOPGL-1-kappa/pDSRα19, is 5476 bp and contains the 7 functional regions shown in Table 2.

TABLE 2

Features of αOPGL-1-kappa/pDSRα19

| Plasmid Base Pair Number: | |
|---|---|
| 2 to 881 | A transcription termination/polyadenylation signal from the α-subunit of the bovine pituitary glycoprotein hormone (α-FSH) (Goodwin, et al, Nucleic Acids Res. 1983 11: 6873-82; Genbank Accession Number X00004) |
| 882 to 2027 | A mouse dihydrofolate reductase (DHFR) minigene containing the endogenous mouse DHFR promoter, the cDNA coding sequences, and the DHFR transcription termination/polyadenylation signals (Gasser et al, Proc Natl Acad Sci USA. 1982 79: 6522-6.; Nunberg et al, Cell 1980 19: 355-64; Setzer et al, J Biol Chem. 1982 257: 5143-7; McGrogan et al, J Biol Chem. 1985 260: 2307-14) |
| 2031 to 3947 | pBR322 sequences containing the ampicillin resistance marker gene and the origin for replication of the plasmid in E. coli (Genbank Accession Number J01749) |

TABLE 2-continued

Features of αOPGL-1-kappa/pDSRα19

| Plasmid Base Pair Number: | |
|---|---|
| 3949 to 4292 | An SV40 early promoter, enhancer and origin of replication (Takebe et al, Mol Cell Biol. 1988 8: 466-72., Genbank Accession Number J02400) |
| 4299 to 4565 | A translational enhancer element from the HTLV-1 LTR domain (Seiki et al, Proc Natl Acad Sci USA. 1983 80: 3618-22, Genbank Accession Number J02029) |
| 4574 to 4730 | An intron from the SV40 16S, 19S splice donor/acceptor signals (Okayama and Berg, Mol Cell Biol. 1983 3: 280-9, Genbank Accession Number J02400) |
| 4750 to 5476 | The αOPGL-1 Kappa light chain cDNA between the XbaI and SalI sites |

A circular plasmid map of the vector is shown in FIG. 5.

Cloning of the αOPGL-1 Heavy Chain

The αOPGL-1 IgG2 heavy chain is cloned from AMG 6.4 hybridoma double-stranded cDNA produced with the Clontech Marathon™ cDNA Amplification Kit (cat. no. K1802-1). Amplification of AMG 6.4 heavy chain cDNA is accomplished by 5' and 3' rapid amplification of cDNA ends (RACE) techniques performed with human germline IgG2 heavy chain constant region specific primers (shown below) and RACE primers and other materials and methods provided in the Marathon™ cDNA amplification kit.

5' IgG2 RACE primer

```
                                              (SEQ ID NO: 9)
5'-GGC ACG GTC ACC ACG CTG CTG AG-3'
```

3' IgG2 RACE primer

```
                                              (SEQ ID NO: 10)
5'-CCT CCA CCA AGG GCC CAT CGG TCT-3'
```

The 600 bp 5' RACE product and 1200 bp 3' RACE product are cloned into pCR2.1 (Invitrogen) and are sequenced. This sequence information is used to design αOPGL-1 heavy chain specific primers for the cloning of the full-length sequence. The heavy chain 5' primer (5' αOPGL-1 IgG2 Primer) is directed against the sense strand and has a HindIII site and consensus Kozak sequence before the natural start site. The heavy chain 3' primer (3' αOPGL-1 IgG2 Primer) is an antisense primer that contains a SalI site and stop codon after the last amino acid of the heavy chain IgG2 sequence.

5' αOPGL-1 IgG2 Primer:

```
5'-CAGAAGCTTGACCACC ATG GAG TTT GGG CTG AGC TGG CTT TTT CTT GTG GC-3'   (SEQ ID NO: 11)
       HindIII Kozak   M   E   F   G   L   S   W   L   F   L   V   A    (SEQ ID NO: 18)
```

3' αOPGL-1 IgG2 Primer:

```
5'-GCA TGTCGAC TTA TCA TTT ACC CGG AGA CAG GGA GAG-3'   (SEQ ID NO: 12)
        SalI    *   *   K   G   P   S   L   S   L       (SEQ ID NO: 19)
```

The double-stranded cDNA described above is used to generate the full-length heavy chain cDNA by PCR amplification with the 5'- and 3'-αOPGL-1 IgG2 primers. The PCR generates a 1433 bp fragment encoding the 467 amino acid residues (including the 19 amino acid IgG signal sequence) of the αOPGL-1 IgG2 heavy chain protein (FIG. 2, SEQ ID NO: 2). Following purification using a QIAquick PCR Purification kit (Qiagen cat. no. 28104), this fragment is used to construct the heavy chain expression vector as follows.

DNA encoding the full-length IgG2 heavy fragment generated above is cut with HindIII and SalI, purified using a QIAquick Gel Extraction kit (Qiagen cat. no. 28704), and this fragment is cloned into pDSRα19. The resulting expression plasmid is named αOPGL-1-IgG2/pDSRα19 (FIG. 6). All vector components are identical to αOPGL-1-kappa/pDSRα19 vector, described above, except the αOPGL-1 IgG2 heavy chain cDNA replaces the αOPGL-1 kappa light chain cDNA between the XbaI and SalI sites. The αOPGL-1 IgG2 heavy chain expression clone is sequenced to confirm that it coded for the same polypeptide that is identified in the AMG 6.4 hybridoma.

Example 2

αOPGL-1 Expression in CHO Cells

Stable expression of αOPGL-1 antibody is achieved by co-transfection of αOPGL-1-kappa/pDSRα19 and αOPGL-1-IgG2/pDSRα19 plasmids into dihydrofolate reductase deficient (DHFR⁻) Chinese hamster ovary cells (CHO AM-1/D, U.S. Pat. No. 6,210,924) followed by isolation and testing of individual clones.

A 100 mm tissue culture dish is plated with 1.5×10⁶ AM-1/D cells grown in CHO d⁻ medium (DMEM-high glucose, 10% fetal bovine serum, 1% penicillin/streptomycin/glutamine, 1× NaPyruvate, 1% nonessential amino acids (NEAA)) (Gibco®) and 1% ht supplement (Gibco®)) the day before transfections (Day 0). On day one, 400 µl of serum-free RPMI 1640 medium (Gibco®) is aliquoted into a 12×75 mm polypropylene tube. Twenty four microliters of TransIT®-LT1 reagent (Mirus Corporation) is added dropwise to the medium and the mixture is allowed to incubate at room temperature for 10 minutes. A total of 15 µg of linearized plasmid DNA (7.5 µg of αOPGL-1-kappa/pDSRα19 and 7.5 µg of αOPGL-1-IgG2/pDSRα19, digested with Pvu1) is then added dropwise to the mixture and is incubated at room temperature for 10 minutes.

The CHO d-medium is removed from the cells, which are washed with 10 ml of Dulbecco's phosphate buffered saline (Gibco®). Six milliliters of serum-free MEM medium supplemented with HT, L-glu, NEAA, and Na pyruvate (Gibco®) is added to the cells. The DNA/LT1 complex is added dropwise to the plates, which are gently rocked back and forth to distribute the DNA evenly over the cells. After 6 hours in a tissue culture incubator, the medium is replaced with fresh CHO d-medium. Forty eight hours later the cells are split to ten 100 mm culture dishes in CHO select medium (DMEM high glucose, 10% dialyzed fetal bovine serum (FBS), 1% penicillin/streptomycin/glutamine, 1% nonessential amino acids and 1× Na pyruvate) (Gibco®). Medium is changed twice weekly until colonies appeared.

After 10-14 days, colonies are picked using 5 mm cloning discs (Labcore®) soaked in 1× trypsin-EDTA (Gibco®) and are cultured in 24 well tissue culture plates with CHO select medium. When the cells become confluent, serum free media (CHO select medium minus FBS) is added and is then collected 48 hours later. These conditioned media are analyzed for antibody expression by Western blot with horse radish peroxidase (HRP)-conjugated goat anti-human IgG Fc antibody (Pierce, Rockford, Ill.) to detect the αOPGL-1 heavy chain, and goat anti-human kappa chain antibody (Pierce, Rockford, Ill.) followed by HRP-conjugated rabbit anti-goat IgG(H+L) antibody (Pierce, Rockford, Ill.) to detect the αOPGL-1 light chain. The highest expressing clones are expanded and stored in liquid nitrogen.

Example 3

Production of αOPGL-1

Preparation and Creation of Cell Line 125Q

CHO cells producing αOPGL-1 are cloned by two rounds of limiting dilution in 96 well plates under serum-free conditions. The clones are selected based on production and growth characteristics in various suspension vessels. EIAs are performed to select the clone that produces the highest level of αOPGL-1. Growth characteristics, including doubling times and densities are then measured by growing the clones in 100 ml, 250 ml, 500 ml, 1 L, and 3 L spinner flasks, as well as in 3 L Aplikon bioreactors. The clone with the fastest doubling time that reaches the highest density in culture is selected, and is designated Cell Line 125Q. When the clone has expanded to yield sufficient cells to freeze 360 ampules at approximately 1×10⁷ cells/mL, cells are resuspended in a cryopreservative, serum-free medium (90% VM-Soy Batch Medium (see Table 3 for details) supplemented with 10 ml/L nonessential amino acids and 10 ml/L L-Glutamine (Gibco/LTI/Invitrogen), and 10% dimethyl sulfoxide (JT Baker)) and frozen. Ampules are stored in a limited access facility and are submerged in liquid nitrogen in liquid nitrogen dewars.

Based on growth and production in small-scale spinners and larger scale bioreactors, Cell Line 125Q is chosen as the cell line for manufacturing of αOPGL-1.

Figure 19:
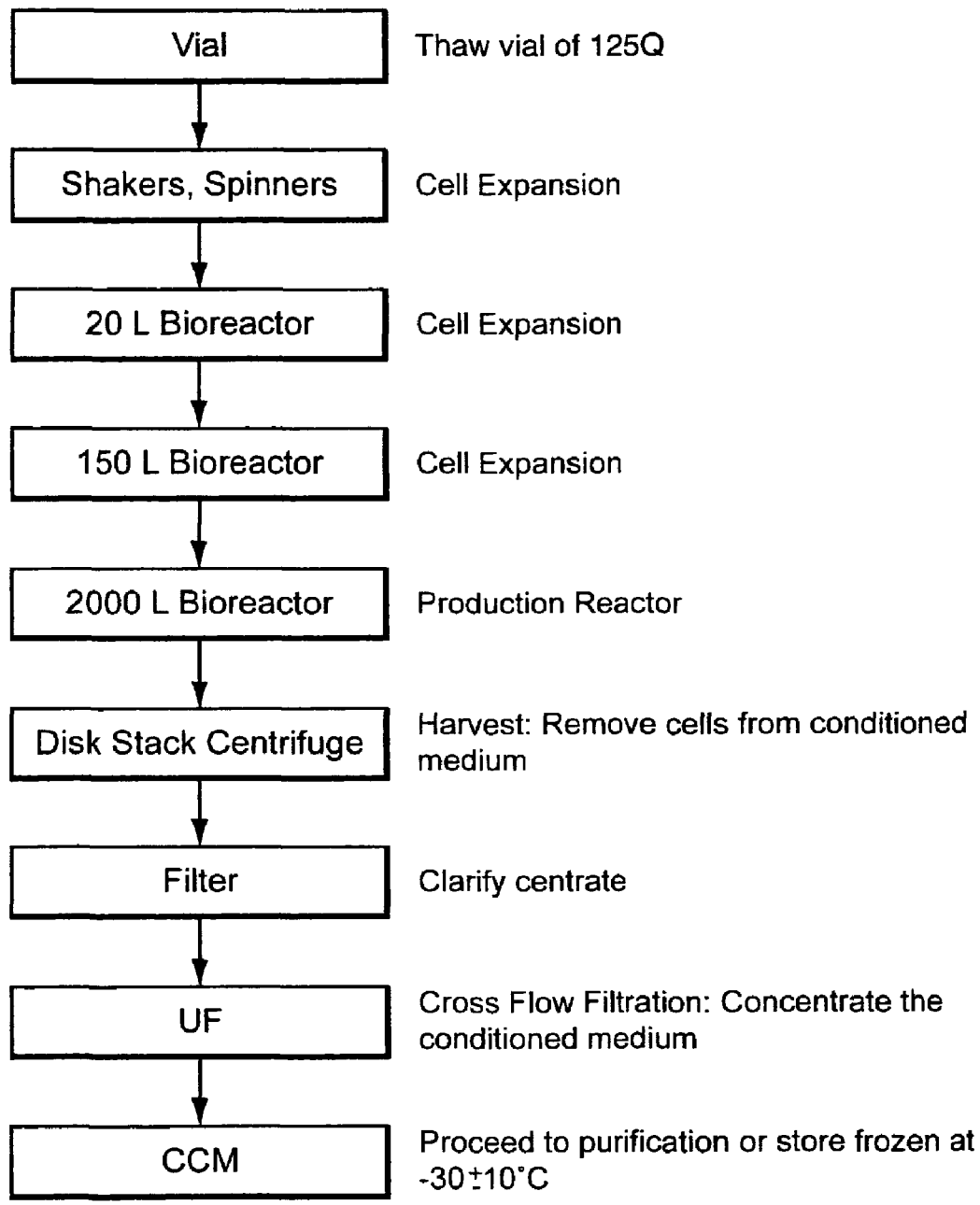
FIG. 19 shows a cell culture process for production of αOPGL-1.

Cell Culture

αOPGL-1 is produced by expression in Cell Line 125Q, a clonal line of CHO cells that expresses αOPGL-1 from plasmids αOPGL-1-kappa/pDSRα19 and αOPGL-1-IgG2/pDSRα19. The cell culture process for αOPGL-1 is shown in FIG. 19. For each production run, cells from a vial of Cell Line 125Q are initially grown in 50 mL of VM-Soy Batch Medium (see Table 3 for composition) supplemented with 10 ml/L nonessential amino acids and 10 ml/L L-glutamine (Gibco/LTI/Invitrogen) (VM-Soy Supp) in 125 ml erlenmeyer shakers at 100 rpm for 5 days. The entire culture is then used to inoculate VM-Soy Supp in a 500 ml spinner flask to $3 \times 10^5$ viable cells/ml (3E5 vc/ml), and is grown with 70 rpm spinning for 3-4 days. The entire culture from the 500 ml spinner flask is then used to inoculate VM-Soy Supp in a 3 L spinner flask to 3E5 vc/ml, and is grown with 70 rpm spinning for 3-4 days.

The culture from the 3 L spinner flask is then split to two 3 L spinner flasks at 3E5 vc/ml in VM-Soy Supp without phenol red and grown under the same conditions. These spinner flask cultures are then used to inoculate four additional spinner flasks at 3E5 vc/ml in VM-Soy Supp without phenol red, and grown under the same conditions. Four liters of culture from the four 3 L spinner flasks is used to inoculate 10 L of VM-Soy Supp without phenol red in a 20 L bioreactor, and the bioreactor is run in fed-batch mode for 7-10 days. In fed-batch mode, a nutrient feed containing concentrated media components ("Feed", as set forth below in Table 3) is added to maintain cell growth and culture viability.

The entire culture from the 20 L bioreactor is then used to inoculate 70 L of VM-Soy Supp without phenol red in a 150 L bioreactor, and the bioreactor is run in fed-batch mode for 9-10 days. Finally, the entire culture from the 150 L bioreactor is used to inoculate approximately 880 L of VM-Soy (without supplement or phenol red) in a 2000 L bioreactor, and the bioreactor is run in fed-batch mode. The rate of feed during fed-batch mode is determined such that the glucose level in the culture is maintained at 0.6 g/L for each bioreactor. The cell density and glucose concentration are measured daily and the rate of feed adjusted accordingly.

Production in the 2000 L bioreactor lasts for approximately two weeks during which time αOPGL-1 is constitutively produced by the cells and secreted into the cell culture medium.

The production reactor is controlled at set pH, temperature, and dissolved oxygen level: pH is 7.0 and is controlled by carbon dioxide gas and sodium carbonate addition; dissolved oxygen is 120 mmHg and is controlled by air, nitrogen, and oxygen gas flows. Cells are maintained at 37° C. throughout the process. All gases are passed through membrane filters of pore size 0.22 μm or less.

At the end of production, the cell broth is fed into a disk stack centrifuge and the culture supernatant is separated from the cells. The centrate is further clarified through a Cuno 90SP depth filter followed by a 0.2 μm Posidyne filter (Pall Co.). The clarified conditioned media is then concentrated by tangential flow ultrafiltration (UF) using 50 kD NMWL membranes (Millipore Biomax 50). The conditioned media is concentrated 15- to 30-fold. The resulting concentrated conditioned medium (CCM) is then either processed through purification or frozen for purification at a later date. The production process is summarized in FIG. 19.

Cell Culture Medium

The cell culture medium for use throughout the entire cell culture process is based on Dulbecco's Modified Eagle's Medium/Ham's Nutrient F12 (DMEM/F12, 1:1), and contains supplemental levels of amino acids, additional nutrients and salts, a soy hydrolysate and recombinant human insulin (Nucellin® Zn, Eli Lilly). The components are listed in Table 3. This media is referred to as VM-Soy. Media solutions are filtered through membrane filters of 0.2 μm pore size prior to use.

TABLE 3

Cell Culture Media Components
COMPONENTS FOR BASAL Media and FEEDS

| COMPONENT | VMSoy Batch Medium (mg/L) | FEED (mg/L) |
|---|---|---|
| DMEM/F12 COMPONENTS Inorganic salts | | |
| $CaCl_2$ (anhyd.) | 116.60 | 233.2 |
| $CuSO_4 \cdot 5H_2O$ | 0.0026 | 0.0052 |
| $Fe(NO_3)_3 \cdot 9H_2O$ | 0.1000 | 0.2 |
| $FeSO_4 \cdot 7H_2O$ | 0.8340 | 1.668 |
| KCl | 311.80 | 623.6 |
| $MgCl_2$ (anhyd.) | 57.280 | 114.56 |
| $MgSO_4$ (anhyd.) | 97.680 | 195.36 |
| NaCl | 905.990 | 1811.98 |
| $NaH_2PO_4 \cdot H_2O$ | 125.00 | 250 |
| $Na_2HPO_4$ | 142.040 | 284.08 |
| $ZnSO_4 \cdot 7H_2O$ | 0.8640 | 1.728 |
| Other Components | | |
| D-Glucose | 3151.00 | 12302 |
| Na Hypoxanthine | 5.40 | 10.8 |
| Linoleic acid | 0.090 | 0.18 |
| Lipoic acid | 0.2060 | 0.412 |
| Phenol Red | 8.10 | 16.2 |
| Putrescine•2HCl | 0.1620 | 0.324 |
| Sodium Pyruvate | 110.00 | 220 |
| Amino acids | | |
| L-Alanine | 26.70 | 53.4 |
| L-Arginine HCl | 295.00 | 590 |
| L-Asparagine•H2O | 45.00 | 90 |
| L-Aspartic acid | 39.90 | 79.8 |
| L-Cysteine•HCl•H2O | 35.120 | 70.24 |
| L-Cystine•2HCl | 62.580 | 125.16 |
| L-Glutamic acid | 44.10 | 88.2 |
| L-Glutamine | 657.00 | 1314 |
| Glycine | 52.50 | 105 |
| L-Histidine•HCl•H2O | 62.950 | 125.9 |
| L-Isoleucine | 108.940 | 217.88 |
| L-Leucine | 118.10 | 236.2 |
| L-Lysine HCl | 182.50 | 365 |
| L-Methionine | 34.480 | 68.96 |
| L-Phenylalanine | 70.960 | 141.92 |
| L-Proline | 57.50 | 115 |
| L-Serine | 73.50 | 147 |
| L-Threonine | 106.90 | 213.8 |
| L-Tryptophan | 18.040 | 36.08 |
| L-Tyrosine•2Na•2H2O | 111.580 | 223.16 |
| L-Valine | 105.70 | 211.4 |
| Vitamins | | |
| Biotin | 0.0073 | 0.0146 |
| D-Ca Pantothenate | 4.480 | 8.96 |
| Choline Chloride | 17.960 | 35.92 |
| Folic Acid | 5.30 | 10.6 |
| i-Inositol | 25.20 | 50.4 |
| Niacinamide | 4.040 | 8.08 |
| Pyridoxal HCl | 4.00 | 8 |
| Pyridoxine HCl | 0.0620 | 0.124 |
| Riboflavin | 0.4380 | 0.876 |
| Thiamine HCl | 4.340 | 8.68 |
| Thymidine | 0.3635 | 0.727 |
| Vitamin B12 | 1.360 | 2.72 |
| ADDITIONAL COMPONENTS | | |
| Nucellin Zn, (rhu insulin) | 5.00 | 15 |
| Selenous Acid | 0.0050 | 0.015 |
| Ethanolamine | 0.0012 | 0.0037 |
| Triiodothyronine | 0.000040 | 0.00012 |
| Hydrocortisone | 0.020 | 0.06 |
| Ferric Citrate | 122.450 | 122.450 |
| Pluronic F-68 | 1000.00 | 500 |
| Soy Hydrolysate | 6000.00 | 6000.00 |
| NaHCO3 | 3000.00 | 3000.00 |
| NaCl | 3500.00 | |

Purification Process

αOPGL-1 expressed in CHO cells is secreted into the extracellular medium. A series of steps may be used to generate pure material. The process uses hydrophobic charge induction, cation exchange, and hydrophobic interaction chromatography along with a low pH step and viral filter. These procedures are described below.

A. Hydrophobic Charge Induction Chromatography (HCIC)

This chromatography step removes the majority of host cell proteins and DNA. The concentrated conditioned media (CCM) is filtered through a Cuno 30SP filter and then through a Cuno VRO7 charged cellulose-based filter, and then loaded on to an MEP HyperCel resin. After loading, the column is washed with equilibration buffer (20 mM Tris pH 7.2). The antibody is eluted from the resin using a low pH buffer (20 mM Sodium Acetate, pH 5.0). As it is eluted from the column, the product is collected based on the absorbance at 280 nm of the column effluent.

B. Viral Inactivation

The MEP pool is titrated to pH 3.7 and is held for approximately 60 minutes to inactivate potentially contaminating retrovirus. Following the hold step, the pH is adjusted to approximately 6.0.

C. Viral Filtration

The pH-adjusted pool is filtered through a Millipore Viresolve NFR filter or equivalent. The antibody flows through the filter while potentially contaminating viruses ≧50 nm are retained.

D. Cation Exchange Chromatography (CEX)

The antibody is further purified by cation exchange chromatography using SP Sepharose HP (Amersham Pharmacia) or equivalent. The cation exchange chromatography step removes additional CHO cell proteins, DNA, lower molecular weight proteins, and aggregated forms of αOPGL-1. The viral filtered pool is loaded onto the cation exchange resin. After loading, the column is washed with equilibration buffer (20 mM NaMES pH 6.2). The antibody is then eluted with a linear gradient of increasing salt (20 mM NaMES pH 6.2, 0 M NaCl to 20 mM NaMES pH 6.2, 0.3 M NaCl). As it is eluted from the column, the product is collected based on the absorbance at 280 nm of the column effluent.

E. Hydrophobic Interaction Chromatography (HIC)

The antibody is further purified by hydrophobic interaction chromatography using Phenyl Toyopearl 650S (Tosoh Biosep) or equivalent. The hydrophobic interaction chromatography step is used as a polishing step and removes additional CHO cell proteins, DNA, lower molecular weight proteins, and aggregated forms of αOPGL-1. The cation exchange pool is conditioned before loading onto the column by addition of ammonium sulfate to a conductivity of >105 mS/cm at 15-25° C. After loading, the column is washed with the equilibration buffer (1M Potassium Phosphate pH 8). The antibody is then eluted with a linear gradient of decreasing salt concentration (1M Potassium Phosphate, 0 mM Tris pH 8 to 0 M Potassium Phosphate, 20 mM Tris pH 8). As it is eluted from the column, the product is collected based on the absorbance at 280 nm of the column effluent.

F. Concentration and Diafiltration

The HIC column pool is concentrated and diafiltered into formulation buffer by tangential flow ultrafiltration using 50 kD NMWL membranes (Millipore Biomax 50). The formulation buffer includes 10 mM Acetate, 5% Sorbitol, pH 5.2 and αOPGL-1 is at 30 mg/mL.

Final Filtration and Storage

The purified bulk is passed through a 0.22 μm PVDF filter (Millipore), is sampled, and stored at approximately −30° C. in a secured freezer.

Example 4

Binding Specificity of αOPGL-1

Antibodies that are produced in CHO cells that are transfected with the two expression vectors as discussed in Examples 1 and 2 may be used in the following examples 4, 5, and 6.

Human OPG binds and neutralizes OPGL in rats, mice and cynomolgus monkeys, as well as in humans. αOPGL-1 binds human OPGL with high affinity but does not bind significantly to murine OPGL (Table 4).

TABLE 4

Affinity of αOPGL-1 to Cell Membrane Expressed OPGL of Human, *Cynomolgus* Monkey, or Mouse Sequence.

| OPGL Species | αOPGL-1 $ED_{50}$ (ng/ml) |
| --- | --- |
| Human | 16 |
| *Cynomolgus* | 19 |
| Mouse | No Specific Binding |

OPGL of these species is expressed in CHO cells as the full-length, membrane-bound protein. Binding of αOPGL-1 to the cell surface expressed OPGL is assessed by FACS analysis of cells incubated with αOPGL-1 and a FITC-labeled secondary antibody to human IgG2. αOPGL-1 binds human and *cynomolgus* OPGL but there is no specific binding to mouse OPGL.

In addition, human OPG has been reported to show weak binding to tumor necrosis factor-related apoptosis-inducing ligand (TRAIL) (Truneh et al, 2000), a related member of the TNF family, which shows DNA and amino acid sequence homology to OPGL (Lacey et al., 1998). However, OPG does not detectably bind to other TNF-related proteins such as TNFα, TNFβ, or CD40 ligand.

αOPGL-1 binds specifically to OPGL on EIA plates (FIG. 7). Recombinant soluble OPGL (2 μg/ml) is coated onto 96-well EIA plates at room temperature for 16 to 24 hours. After blocking with 1% BSA in PBS, varying concentrations of αOPGL-1 (approximately 2 ng/ml to 1000 ng/ml) diluted in 1% BSA/PBS are added to the wells and the plates are incubated for about 2 hours at room temperature. Bound antibody is detected with goat anti-Human IgG (Fab')-HRP using TMB-H2O2 (tetramethylbenzidine and hydrogen peroxide) substrate cocktail. The absorbance is read at 450 nm and 650 nm.

αOPGL-1 binds specifically OPGL expressed on the surface of transfected cells (FIG. 8). αOPGL-1 (100 ng/ml) diluted in FACS Buffer (PBS, 0.1% BSA, 0.01% Sodium Azide) is preincubated with varying concentrations of OPGL, TNFa, TNFb, TRAIL, or CD40 ligand (approximately 0.1 ng/ml to 1.000 ng/ml), and is then added to approximately 200,000 CHO REN 218-9 cells, which are CHO cells stably expressing membrane-bound OPGL on the cell surface. After 1 hour at 2-8° C., unbound antibody is removed by centrifugation and washing. Cells are then incubated for 30 minutes at 2-8° C. with FITC-labeled F(ab')$_2$ Goat anti-Human IgG (Fcγ fragment specific). After centrifugation and washing, cell surface fluorescence is measured using flow cytometry. FIG. 8 shows that binding of αOPGL-1 to CHO REN 218-9 cells is specific, and is competitively reduced by addition of soluble OPGL, but not by addition of TNFa, TNFb, TRAIL, or CD40 ligand.

Figure 9:
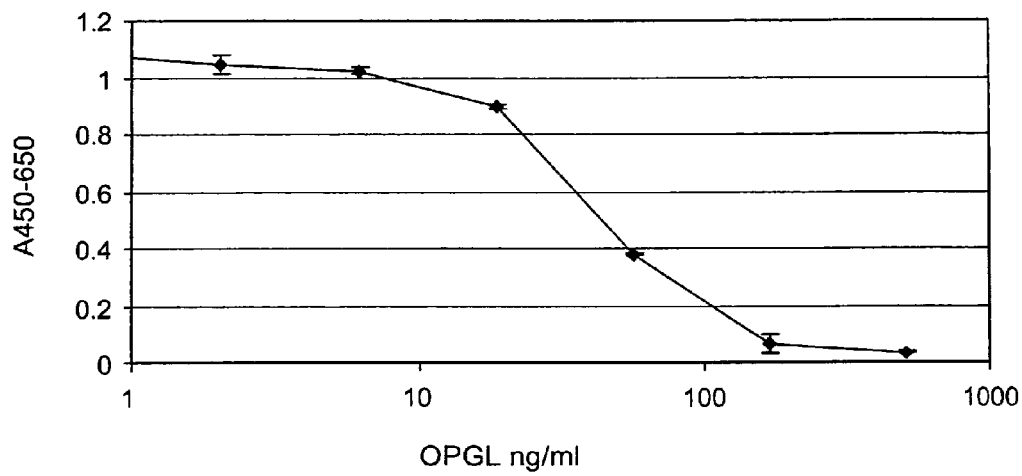
FIG. 9 shows inhibition of αOPGL-1 binding to OPGL-coated EIA plates by soluble OPGL. αOPGL-1 binding to OPGL on an EIA plate is reduced competitively by exogenously added soluble OPGL.
Figure 10:
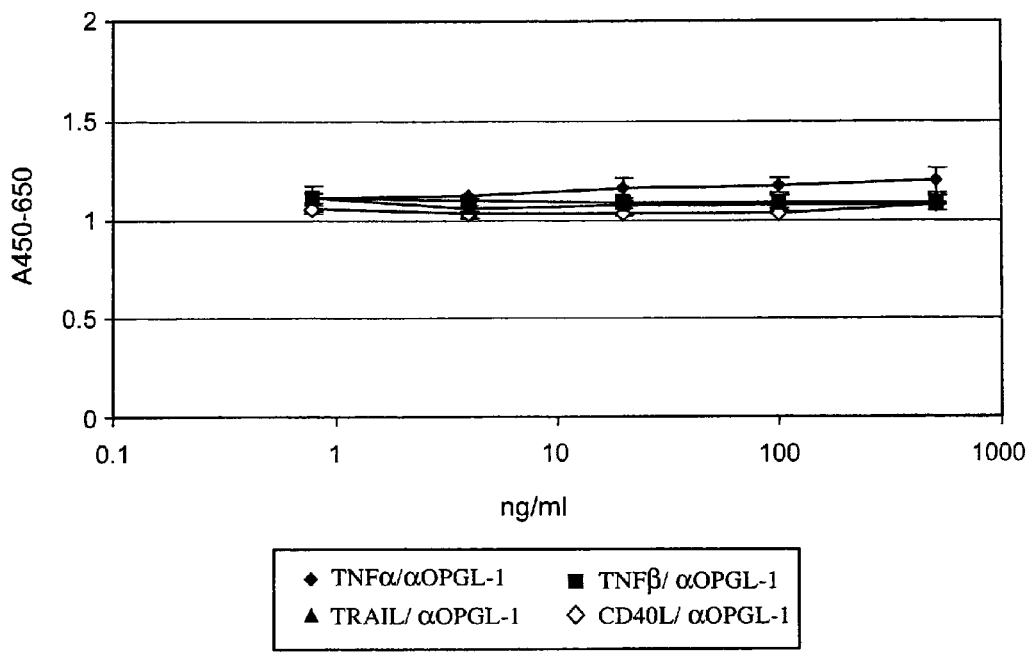
FIG. 10 shows specific binding of αOPGL-1 to OPGL-coated EIA plates. αOPGL-1 binding to OPGL on an EIA plate is not reduced by exogenously added TNF-α, TNF-β, TRAIL, or CD40 Ligand.

In competition experiments, αOPGL-1 binding to OPGL on EIA plates is inhibited by addition of exogenous OPGL (FIG. 9), but not by the addition of TNFα, TNFβ, TRAIL, or CD40 ligand (FIG. 10). This procedure is performed in substantially the same manner as above, for binding of αOPGL-1 to OPGL on EIA plates, except a constant concentration of αOPGL-1 (100 ng/mL) is preincubated with varying concentrations of soluble OPGL or other ligands (approximately 1 ng/ml to 1000 ng/ml for each) before it is added to the OPGL-coated plates.

Example 5

αOPGL-1 Neutralizing Activity

Inhibition of Osteoclast Formation

RAW 264.7 (ATCC No. TIB-71, Manassas, Va.) is a murine macrophage cell line that was derived from an Abelson murine leukemia virus-induced tumor. RAW 264.7 cells will differentiate to osteoclast-like cells in the presence of OPGL. The basic assay for generation of osteoclasts in culture from RAW cells in the presence of OPGL has been described in detail in Simonet et al (1997) *Cell* 89 p. 309, and Lacey et al (1998) *Cell* 93 p. 165, which are herein incorporated by reference for any purpose.

RAW cells are stimulated by ligand to differentiate into osteoclast-like cells, and the differentiation can be measured by TRAP activity, a property of osteoclasts. Thus, the effect of αOPGL-1 on osteoclastogenesis can be measured.

RAW cells are incubated for 4 days in the presence of a constant amount of OPGL (40 ng/ml) and varying amounts of αOPGL-1 (6.3 ng/ml to 200 ng/ml) in cell culture medium (DMEM, 10% FBS, 0.292 mg/ml L-Glut, 100 units/ml Penicillin G, 100 μg/ml Streptomycin sulfate). At the end of 4 days, the cells are stained for tartrate-resistant acid phosphatase (TRAP) activity by permeabilization and acidification, followed by treatment with para-nitrophenylphosphate for 5 minutes. Briefly, the media is aspirated off of the cells, and 100 μl of citrate buffer (410 ml 0.1M citric acid, 590 ml 0.1 M citrate, trisodium salt, 1 mL triton X-100) is added to each well and the plates are incubated for 3 to 5 minutes at room temperature. One hundred microliters of PNPP solution is then added (157.8 mg acid phosphatase reagent (Sigma 104-100), 7.2 ml tartrate solution (Sigma cat. no. 387-3), and 22.8 ml citrate buffer), and plates are incubated for 3 to 5 minutes at room temperature. The reaction is terminated by addition of 50 μl 0.5 M NaOH solution.

Figure 11:
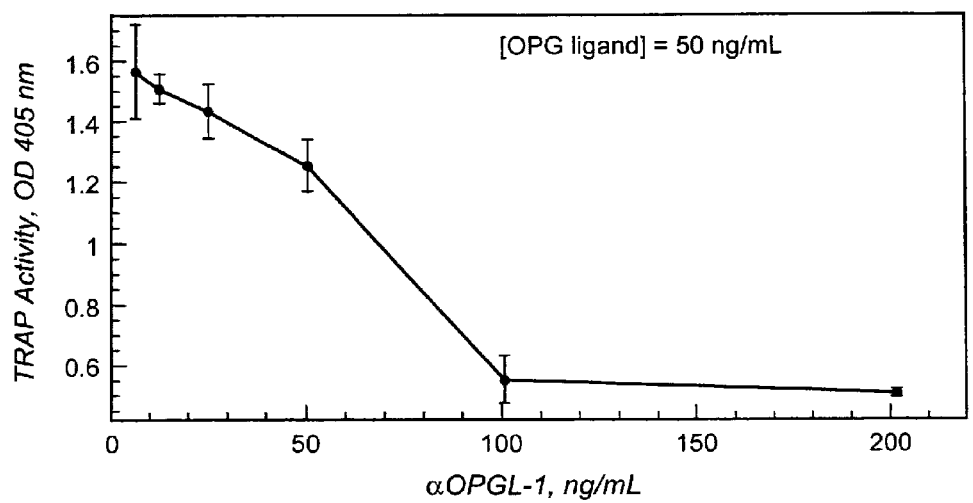
FIG. 11 shows dose-dependent inhibition of osteoclast formation by αOPGL-1. The dose-dependent inhibition by αOPGL-1 of OPGL-induced TRAP activity in RAW 264.7 cells is shown.

TRAP will convert para-nitrophenylphosphate to para-nitrophenol, which can be quantitated by optical density measurement at 405 nm. The TRAP activity, which is a surrogate marker for osteoclast development, therefore correlates with the optical density at 405 nm. A plot of optical density versus αOPGL-1 concentration is shown in FIG. 11, and demonstrates that αOPGL-1 inhibits osteoclast formation in this assay.

Inhibition of OPGL Binding to its Receptor

The potency of αOPGL-1 is demonstrated by its ability to block the binding of OPG ligand to its cognate receptor, the osteoclast differentiation and activating receptor (ODAR, also known as RANK). This assay uses homogeneous time resolved fluorescent resonance (HTRF) to detect binding of αOPGL-1 to Europium-conjugated osteoprotegerin ligand (Eu-OPGL). If αOPGL-1 inhibits Eu-OPGL binding to ODAR, fluorescent output will decrease, and the amount of αOPGL-1 present will be inversely related to the amount of fluorescence.

OPGL is labeled with europium, which emits light at 620 nm when excited with 337 nm light. ODAR is fused to FLAG and to Fc, and the Fc-ODAR-FLAG fusion protein is labeled with an anti-FLAG antibody linked to allophycocyanin (APC), a fluorophore which emits 665 nm light when excited by light at 620 nm. Therefore, when Eu-labeled OPG ligand binds to the Fc-ODAR-FLAG/anti-FLAG-APC complex, the tertiary complex will emit 665 nm light when excited with light at 337 nm.

Eu-OPGL at 0.05 μg/ml is preincubated with various concentrations (0.1 to 150 ng/ml) of αOPGL-1 in assay buffer (50 mM Tris pH 8, 100 mM NaCl, 0.05% NaN$_3$, 0.1% BSA, and 0.05% Tween 20) at room temperature for approximately one hour (Preincubation mix). A mixture of Fc-ODAR-FLAG (1 μg/ml) and anti-FLAG-APC (2.5 μg/ml) is also prepared in assay buffer and incubated at room temperature for one hour (Fluorochrome mix). Equal volumes of Preincubation mix and Fluorochrome mix are then combined and incubated at room temperature for 3 hours. The fluorescence is measured by reading plates on the Packard Discovery HTRF microplate analyzer using an excitation wavelength of 337 nm and an emission wavelength of 665 nm.

Figure 12:
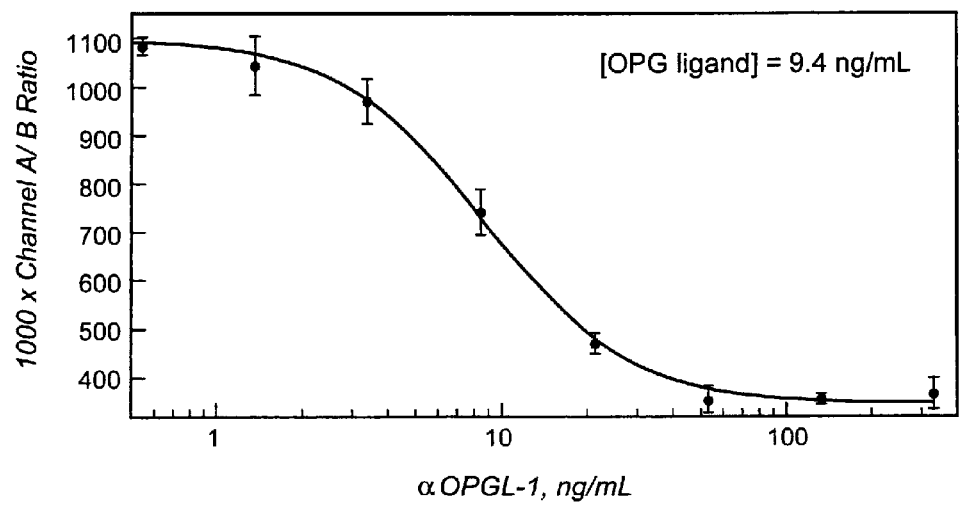
FIG. 12 shows dose-dependent inhibition of OPGL binding to ODAR by αOPGL-1. The dose-dependent inhibition by αOPGL-1 of europium-labeled OPGL binding to ODAR-FLAG/anti-FLAG-APC is shown.

When αOPGL-1 is preincubated with Eu-OPG ligand and is then mixed with Fc-ODAR-FLAG/anti-FLAG-APC, the fluorescence intensity at 665 nm decreases in a dose-dependent manner, as shown in FIG. 12, demonstrating that αOPGL162 can effectively inhibit OPGL binding to ODAR.

Example 6

Pharmacokinetics in Cynomolgus Monkeys

Six male and six female cynomolgus monkeys, not greater than 4.5 years of age and weighing 2 to 4 kg are assigned to 4 dose groups. Group 1 consists of 3 males and 3 females. Groups 2, 3, and 4 each consists of 1 male and 1 female. Animals in Group 1 are administered a single SC dose of 1 mg/kg αOPGL-1, while animals in Groups 2, 3 and 4 are administered single IV doses of 0.1, 1.0, or 10.0 mg/kg of αOPGL-1, respectively.

Animals are dosed with αOPGL-1 expressed from transfected Chinese hamster ovary (CHO) cells. Serum samples are taken for determination of αOPGL-1 levels, antibody analysis, and analysis of the bone turnover marker serum N-telopeptide (serum N-Tx), alkaline phosphatase (ALP), and serum calcium (serum Ca). Urine is also collected for analysis of N-telopeptide (urine N-Tx) and creatinine.

Figure 13:
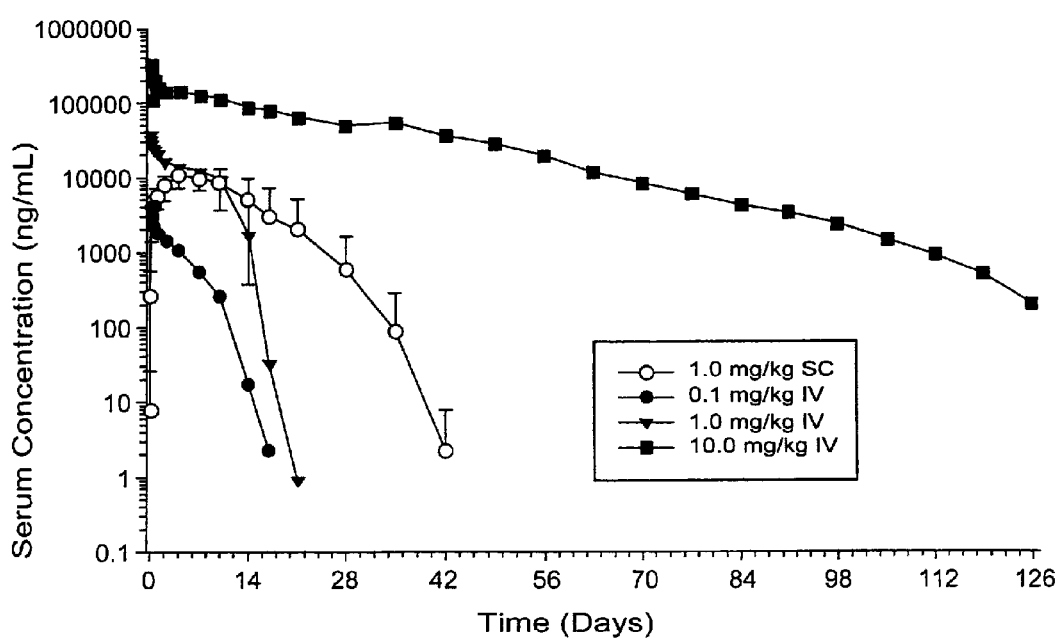
FIG. 13 shows the mean serum concentration time profiles after administering a single dose of αOPGL-1 to Cynomolgus Monkeys. Doses of 0.1, 1, and 10.0 mg/kg were administered intravenously (n=2 per dose) and doses of 1.0 mg/kg were administered subcutaneously (n=6).

The serum concentration-time profiles following IV administration are characterized by a tri-phasic distribution (FIG. 13). Initially, there is a rapid distribution phase, followed by a significantly slower plateau phase, which appears to be concentration-dependent. The third observed phase is a rapid elimination phase.

Non-compartmental analysis of complete serum concentration-time profiles using WinNonlin Professional (v1.5), and exponential analysis of the data up to 14 days after test article administration and above 10,000 ng/mL using SAAM II (v1.1.2) are utilized to investigate the pharmacokinetics of αOPGL-1 in monkeys. The initial volume of distribution from all IV doses averages 28.9 ml/kg, similar to plasma volume. Steady state volume ($V_{SS}$) of distribution averages 39 ml/kg across all IV doses. Exponential analysis indicates that αOPGL-1 has an average distribution half-life ($t_{1/2\alpha}$) of 6.02 hours, an extended secondary phase with a half-life ($t_{1/2\beta}$) that increases with dose from 86.9 hours at a dose of 0.1 mg/kg to a maximum of 444 hours at a dose of 10.0 mg/kg. Terminal elimination half-life ($t_{1/2z}$) estimated non-compartmentally averages 31 hours across all IV dose groups. Clearance (CL, CL/F) of αOPGL-1 is found to be non-linear, with animals receiving IV doses of 10 mg/kg having an average clearance (0.120 ml/hr/kg) that is 3.3-fold lower than those receiving 0.1 mg/kg (0.401 ml/hr/kg).

After administering subcutaneously, absorption is slow, with average peak concentrations ($C_{max}$) of 11,600 ng/ml at 132 hr. There is high variability in the range of exposure after SC administration, resulting in an average clearance of 0.387±0.281 ml/hr/kg and mean residence time of 202±80.1 hours. Average bioavailability is 89%.

Figure 14:
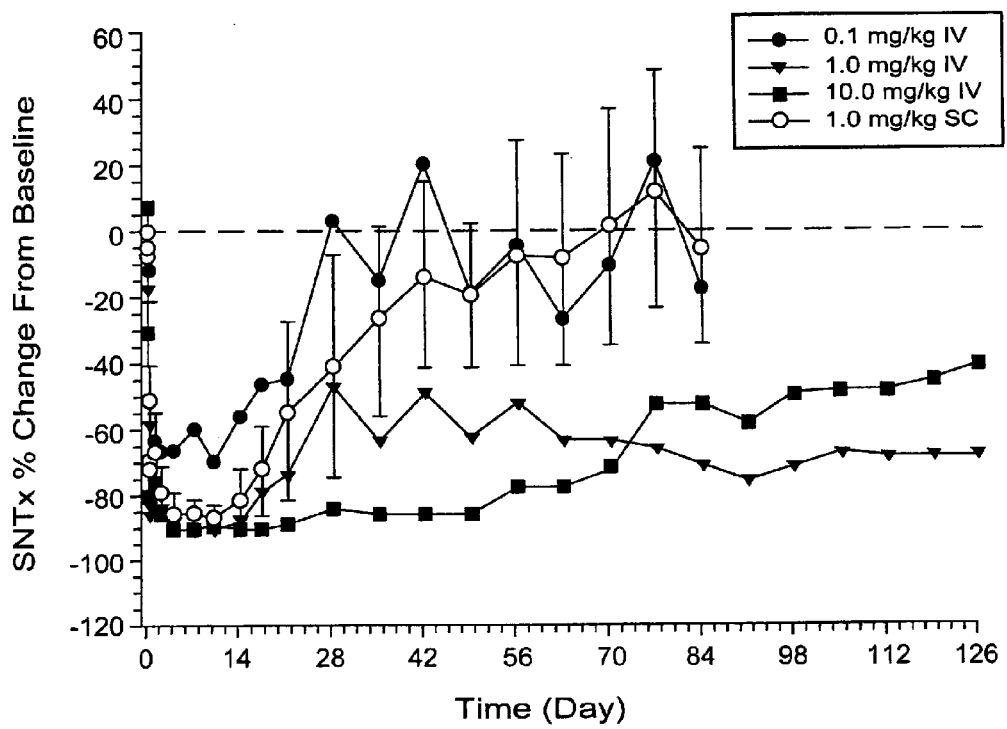
FIG. 14 shows the mean percent change in serum N-Tx concentration after administering a single dose of αOPGL-1 to Cynomolgus Monkeys. Doses of 0.1, 1, and 10.0 mg/kg were administered intravenously (n=2 per dose) and doses of 1.0 mg/kg were administered subcutaneously (n=6).
Figure 15:
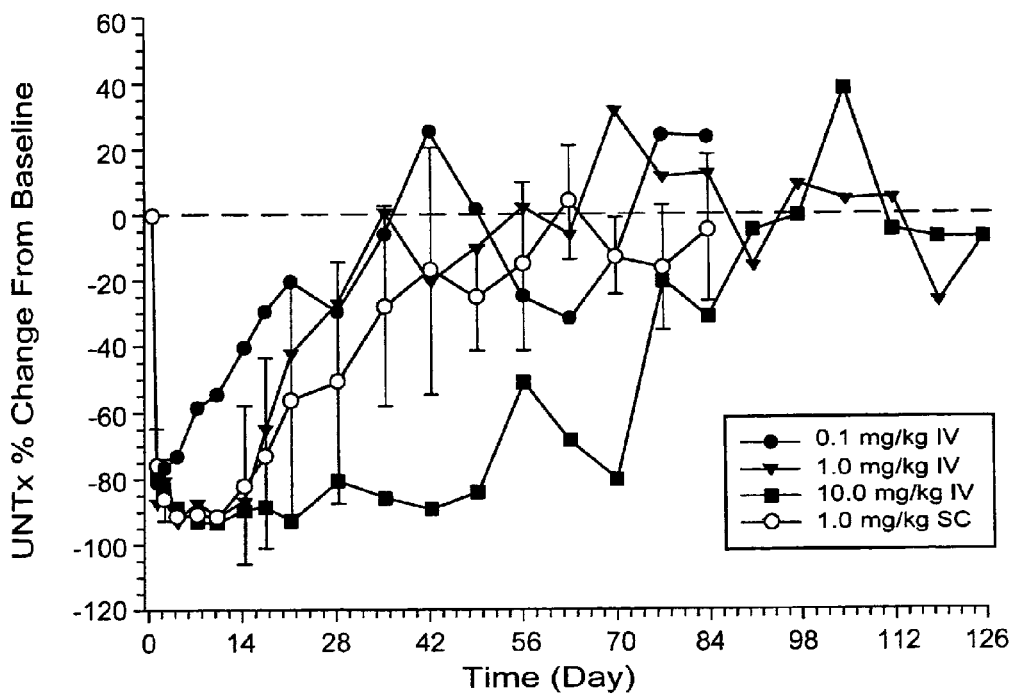
FIG. 15 shows the mean percent change in urine N-Tx concentration after administering a single dose of αOPGL-1 to Cynomolgus Monkeys. Doses of 0.1, 1, and 10.0 ma/kg were administered intravenously (n=2 per dose) and doses of 1.0 mq/kq were administered subcutaneously (n=6).

The preceding data are summarized in Table 5.

αOPGL-1 causes a rapid decrease in serum N-Tx levels within 24 hours post dose (FIG. 14). The average time of maximum effect is observed to occur between 12 hours and 7 days post dose as IV doses increase from 0.1 to 10 mg/kg, and between 12 hours and 11 days in animals receiving a SC dose of 1.0 mg/kg. Maximum effect increases with dose from approximately 80 to 91% over the dose range of 0.1 to 1 mg/kg. However, at higher doses no further suppression is observed with maximum inhibition of 91%. Mean levels of serum N-Tx return to baseline by day 28 after administering 0.1 mg/kg IV and by day 70 after administering 1 mg/kg SC. Urine N-Tx shows similar trends to those of serum N-Tx, except that all groups return to baseline values by study day 105 (FIG. 15).

Figure 20:
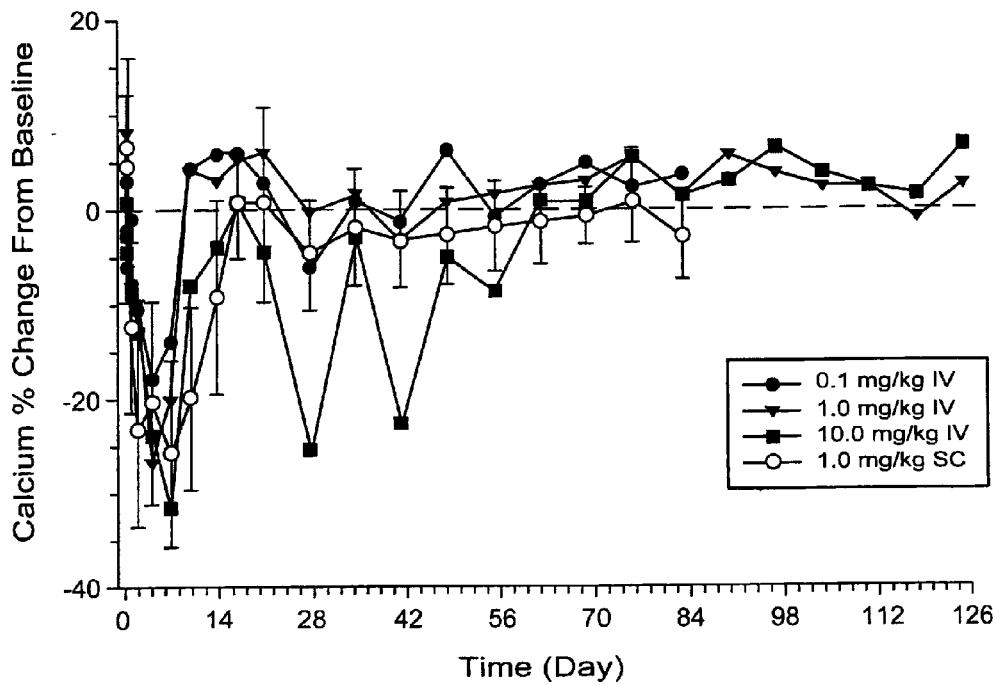
FIG. 20 shows the serum calcium percent change from baseline after administering a single dose of αOPGL-1 to Cynomolgus monkeys.

Suppression of serum Ca increases with dose to a mean nadir of 31.6% below the baseline average seven days after IV administration of 10.0 mg/kg. All other dose groups have mean decreases in serum Ca of less than 26.4% from their baseline averages. By day 17 all serum Ca levels in treated animals return to within 10% of their baseline averages (FIG. 20).

Figure 21:
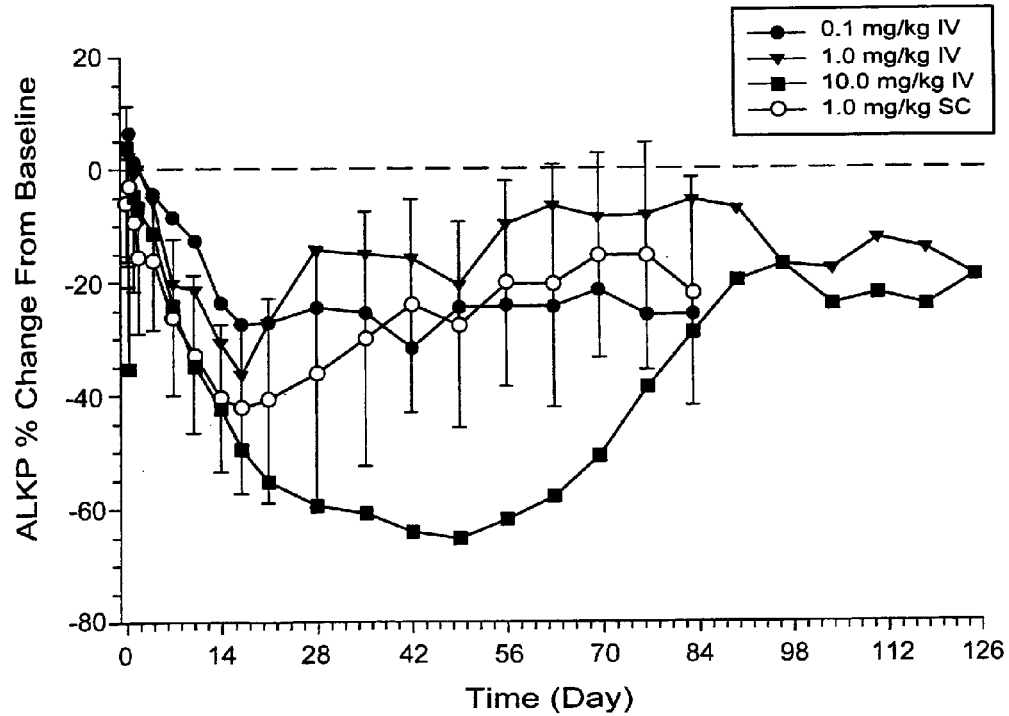
FIG. 21 shows the mean serum Alkaline Phosphatase percent change from baseline after administering a single dose of αOPGL-1 to Cynomolgus monkeys.

As bone resorption and formation are intimately linked, changes in bone formation markers (ALP) are also observed with a much slower decline in ALP levels and a more prolonged suppression than the formation marker, N-Tx (FIG. 21). Observing bone resorption markers decrease prior to bone formation markers (ALP) following dosing with αOPGL-1 confirms that the αOPGL-1 is a bone anti-resorptive agent.

Figures 16, 17, 18:
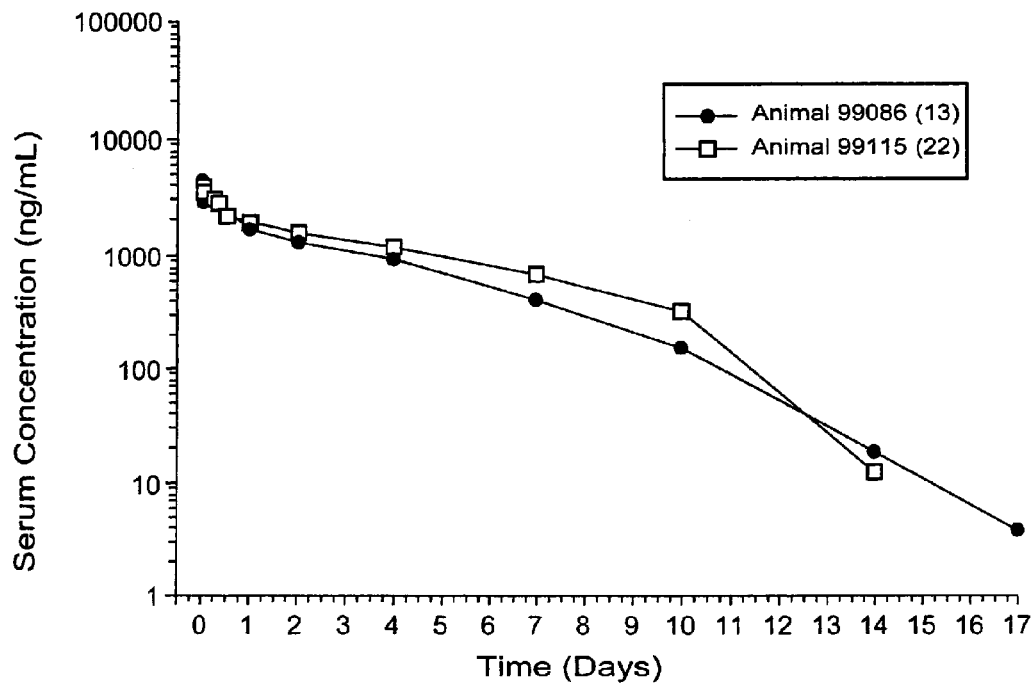
FIG. 16 shows antibody positive (open symbols) and negative (closed symbols) serum-concentration time profiles after administering a single dose of 0.1 mg/kg αOPGL-1 to Cynomolgus Monkeys.
FIG. 17 shows the amino acid sequence of the αOPGL-1 antibody heavy chain variable region (SEQ ID NO: 13).
FIG. 18 shows the amino acid sequence of the αOPGL-1 antibody light chain variable region (SEQ ID NO: 14).

The majority of animals (9 of 12) develop antibodies to αOPGL-1. The incidence of antibodies to αOPGL-1 is not dose or route dependent. It is not possible to assess the effect of antibodies to αOPGL-1 on αOPGL-1 pharmacokinetics above 0.1 mg/kg when no dose group has both antibody negative and positive animals. At 0.1 mg/kg IV, the majority of αOPGL-1 is cleared prior to antibody development and therefore, effects on αOPGL-1 disposition are not observed (FIG. 16).

TABLE 5

Mean (±SD) Non-Compartmental Pharmacokinetic Parameters[a] in Cynomolgus Monkeys After Administering a Single Dose of αOPGL-1 IV and SC Non-Compartmental Parameter Estimates

| Parameter | Unit | 1.0 mg/kg SC (n = 6) | | 0.1 mg/kg IV (n = 2) | 1.0 mg/kg IV (n = 2) | 10 mg/kg IV (n = 2) |
|---|---|---|---|---|---|---|
| | | Mean | SD | Mean | Mean | Mean |
| $T_{max}$ | hr | 132 | 60.2 | 0 | 0 | 0 |
| $C_{max}$ | ng/ml | 11600 | 3410 | 4330 | 38200 | 326000 |
| $t_{1/2z}$ | hr | 34.9 | 11.1 | 30.7 | 31.4 | ND[b] |
| $AUC_{(0-\infty)}$ | μg * hr/ml | 3520 | 1750 | 253 | 3950 | 99900 |
| CL, CL/F | ml/hr/kg | 0.387 | 0.281 | 0.401 | 0.256 | 0.120 |
| MRT | hr | 202 | 80.1 | 84.8 | 124 | 519 |
| Vss | ml/kg | N/A[c] | N/A | 33.7 | 31.7 | 55.9 |

[a] Values are reported to 3 significant figures

[b] Not Determined, PK samples end during plateau (β) phase hence terminal phase is not observed

[c] Not Applicable

We claim:

1. A composition comprising a first polynucleotide and a second polynucleotide, wherein the first polynucleotide encodes a heavy chain comprising CDR1, CDR2, and CDR3 of SEQ ID NO: 13 and the second polynucleotide encodes a light chain comprising CDR1, CDR2, and CDR3 of SEQ ID NO: 14,
wherein an antibody comprising the heavy chain and the light chain interacts with a human osteoprotegerin ligand (OPGL) and inhibits binding of human OPGL to an osteoclast differentiation and activation receptor (ODAR).

2. The composition of claim 1, wherein the first polynucleotide and the second polynucleotide are part of the same nucleic acid molecule.

3. The composition of claim 1, wherein the first polynucleotide and the second polynucleotide are operably linked such that they encode a single-chain antibody.

4. The composition of claim 3, wherein the single-chain antibody is a single-chain Fv antibody.

5. The composition of claim 1, which encodes a Fab antibody.

6. The composition of claim 1, which encodes a Fab' antibody.

7. The composition of claim 1, which encodes a F(ab')₂ antibody.

8. The composition of claim 1, which encodes a fully human antibody.

9. A vector comprising at least one polynucleotide selected from a first polynucleotide that encodes the amino acid sequence of SEQ ID NO: 13 and a second polynucleotide that encodes the amino acid sequence of SEQ ID NO: 14.

10. The vector of claim 9, wherein the vector comprises at least one polynucleotide selected from a first polynucleotide that encodes the amino acid sequence of SEQ ID NO: 2 and a second polynucleotide that encodes the amino acid sequence of SEQ ID NO: 4.

11. A host cell comprising at least one vector of claim 9.

12. A method of producing an antibody that interacts with OPGL, comprising expressing a first polynucleotide and a second polynucleotide in an isolated host cell, wherein the first polynucleotide encodes a heavy chain comprising CDR1, CDR2, and CDR3 of SEQ ID NO: 13 and the second polynucleotide encodes a light chain comprising CDR1, CDR2, and CDR3 of SEQ ID NO: 14, and wherein an antibody comprising the heavy chain and the light chain interacts with a human osteoprotegerin ligand (OPGL) and inhibits binding of human OPGL to an osteoclast differentiation and activation receptor (ODAR).

13. The method of claim 12, wherein the first polynucleotide encodes the amino acid sequence of SEQ ID NO: 2 and the second polynucleotide encodes the amino acid sequence of SEQ ID NO: 4.

14. The method of claim 12, wherein the first polynucleotide encodes an amino acid sequence comprising the amino acid sequence as set forth in SEQ ID NO: 2 from residue 20 to residue 467, and the second polynucleotide encodes an amino acid sequence comprising the amino acid sequence as set forth in SEQ ID NO: 4 from residue 21 to residue 235.

15. A composition comprising a first polynucleotide and a second polynucleotide, wherein the first polynucleotide encodes a heavy chain comprising the amino acid sequence as set forth in SEQ ID NO: 13 and the second polynucleotide encodes a light chain, wherein an antibody comprising the heavy chain and the light chain interacts with a human osteoprotegerin ligand (OPGL) and inhibits binding of human OPGL to an osteoclast differentiation and activation receptor (ODAR).

16. The composition of claim 15, wherein the first polynucleotide encodes a heavy chain comprising the amino acid sequence as set forth in SEQ ID NO: 2 from residue 20 to residue 467.

17. The composition of claim 15, wherein the first polynucleotide encodes a heavy chain consisting of the amino acid sequence as set forth in SEQ ID NO: 2 from residue 20 to residue 467.

18. The composition of claim 15, wherein the second polynucleotide encodes a light chain comprising the amino acid sequence as set forth in SEQ ID NO:14.

19. The composition of claim 16, wherein the second polynucleotide encodes a light chain comprising the amino acid sequence as set forth in SEQ ID NO:14.

20. The composition of claim 17, wherein the second polynucleotide encodes a light chain comprising the amino acid sequence as set forth in SEQ ID NO:14.

21. The composition of claim 15, wherein the second polynucleotide encodes a light chain comprising the amino acid sequence as set forth in SEQ ID NO: 4 from residue 21 to residue 235.

22. The composition of claim 17, wherein the second polynucleotide encodes a light chain comprising the amino acid sequence as set forth in SEQ ID NO: 4 from residue 21 to residue 235.

23. The composition of claim 15, wherein the second polynucleotide encodes a light chain consisting of the amino acid sequence as set forth in SEQ ID NO: 4 from residue 21 to residue 235.

24. The composition of claim 16, wherein the second polynucleotide encodes a light chain consisting of the amino acid sequence as set forth in SEQ ID NO: 4 from residue 21 to residue 235.

25. The composition of claim 15, wherein the first polynucleotide encodes a heavy chain comprising the amino acid sequence as set forth in SEQ ID NO: 2 from residue 20 to residue 467, and the second polynucleotide encodes a light chain comprising the amino acid sequence as set forth in SEQ ID NO: 4 from residue 21 to residue 235.

26. The composition of claim 15, wherein the first polynucleotide encodes a heavy chain consisting of the amino acid sequence as set forth in SEQ ID NO: 2 from residue 20 to residue 467, and the second polynucleotide encodes a light chain consisting of the amino acid sequence as set forth in SEQ ID NO: 4 from residue 21 to residue 235.

27. A composition comprising a first polynucleotide and a second polynucleotide, wherein the first polynucleotide encodes a heavy chain and the second polynucleotide encodes a light chain comprising the amino acid sequence as set forth in SEQ ID NO:14, wherein an antibody comprising the heavy chain and the light chain interacts with a human osteoprotegerin ligand (OPGL) and inhibits binding of human OPGL to an osteoclast differentiation and activation receptor (ODAR).

28. The composition of claim 27, wherein the second polynucleotide encodes a light chain comprising the amino acid sequence as set forth in SEQ ID NO: 4 from residue 21 to residue 235.

29. The composition of claim 27, wherein the second polynucleotide encodes a light chain consisting of the amino acid sequence as set forth in SEQ ID NO: 4 from residue 21 to residue 235.

30. A method of producing an antibody that interacts with OPGL, comprising expressing a first polynucleotide and a second polynucleotide in an isolated host cell, wherein the first polynucleotide encodes a heavy chain comprising the amino acid sequence set forth in SEQ ID NO:13 and the second polynucleotide encodes a light chain, and wherein an antibody comprising the heavy chain and the light chain interacts with a human osteoprotegerin ligand (OPGL) and inhibits binding of human OPGL to an osteoclast differentiation and activation receptor (ODAR).

31. A method of producing an antibody that interacts with OPGL, comprising expressing a first polynucleotide and a second polynucleotide in an isolated host cell, wherein the first polynucleotide encodes a heavy chain and the second polynucleotide encodes a light chain comprising the amino acid sequence of SEQ ID NO: 14, and wherein an antibody comprising the heavy chain and the light chain interacts with a human osteoprotegerin ligand (OPGL) and inhibits binding of human OPGL to an osteoclast differentiation and activation receptor (ODAR).

32. The method of claim 31, wherein the first polynucleotide encodes a heavy chain comprising the amino acid sequence of SEQ ID NO: 13.

33. An antibody produced by the method of any one of claims 12, and 30, and 31.

34. The composition of claim 15 or 27, wherein the first polynucleotide and the second polynucleotide are part of the same nucleic acid molecule.

35. The composition of claim 15 or 27, wherein the first polynucleotide and the second polynucleotide are operably linked such that they encode a single-chain antibody.

36. The composition of claim 35, wherein the single-chain antibody is a single-chain Fv antibody.

37. The composition of claim 15 or 27, which encodes a Fab antibody.

38. The composition of claim 15 or 27, which encodes a Fab' antibody.

39. The composition of claim 15 or 27, which encodes a F(ab')$_2$ antibody.

40. The composition of claim 15 or 27, which encodes a fully human antibody.

* * * * *

UNITED STATES PATENT AND TRADEMARK OFFICE
CERTIFICATE OF CORRECTION

| | | |
|---|---|---|
| PATENT NO. | : 8,058,418 B2 | Page 1 of 1 |
| APPLICATION NO. | : 11/981664 | |
| DATED | : November 15, 2011 | |
| INVENTOR(S) | : Boyle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 523 days.

Signed and Sealed this
Twentieth Day of March, 2012

David J. Kappos
*Director of the United States Patent and Trademark Office*

SEQUENCE LISTING

<160> NUMBER OF SEQ ID NOS: 20

<210> SEQ ID NO 1
<211> LENGTH: 1426
<212> TYPE: DNA
<213> ORGANISM: Mus musculus

<400> SEQUENCE: 1

```
aagcttgacc accatggagt ttgggctgag ctggcttttt cttgtggcta ttttaaaagg      60
tgtccagtgt gaggtgcagc tgttggagtc tgggggaggc ttggtacagc ctgggggtc     120
cctgagactc tcctgtgcag cctctggatt cacctttagc agctatgcca tgagctgggt     180
ccgccaggct ccagggaagg ggctggagtg ggtctcaggt attactggga gtggtggtag     240
tacatactac gcagactccg tgaagggccg gttcaccatc tccagagaca attccaagaa     300
cacgctgtat ctgcaaatga acagcctgag agccgaggac acggccgtat attactgtgc     360
gaaagatcca gggactacgg tgattatgag ttggttcgac ccctggggcc agggaaccct     420
ggtcaccgtc tcctcagcct ccaccaaggg cccatcggtc ttccccctgg cgccctgctc     480
caggagcacc tccgagagca gcggccct gggctgcctg gtcaaggact acttccccga     540
accggtgacg gtgtcgtgga actcaggcgc tctgaccagc ggcgtgcaca ccttcccagc     600
tgtcctacag tcctcaggac tctactccct cagcagcgtg gtgaccgtgc cctccagcaa     660
cttcggcacc cagacctaca cctgcaacgt agatcacaag cccagcaaca ccaaggtgga     720
caagacagtt gagcgcaaat gttgtgtcga gtgcccaccg tgcccagcac cacctgtggc     780
aggaccgtca gtcttcctct ccccccaaa cccaaggac accctcatga tctcccggac     840
ccctgaggtc acgtgcgtgg tggtggacgt gagccacgaa gaccccgagg tccagttcaa     900
ctggtacgtg gacggcgtgg aggtgcataa tgccaagaca aagccacggg aggagcagtt     960
caacagcacg ttccgtgtgg tcagcgtcct caccgttgtg caccaggact ggctgaacgg    1020
caaggagtac aagtgcaagg tctccaacaa aggcctccca gccccatcg agaaaaccat    1080
ctccaaaacc aaagggcagc ccgagaaacc acaggtgtac accctgcccc catcccggga    1140
ggagatgacc aagaaccagg tcagcctgac ctgcctggtc aaaggcttct accccagcga    1200
catcgccgtg gagtgggaga gcaatgggca gccggagaac aactacaaga ccacacctcc    1260
catgctggac tccgacggct ccttcttcct ctacagcaag ctcaccgtgg acaagagcag    1320
gtggcagcag gggaacgtct tctcatgctc cgtgatgcat gaggctctgc acaaccacta    1380
cacgcagaag agcctctccc tgtctccggg taaatgataa gtcgac                  1426
```

<210> SEQ ID NO 2
<211> LENGTH: 467
<212> TYPE: PRT
<213> ORGANISM: Mus musculus

<400> SEQUENCE: 2

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60
```

```
Glu Trp Val Ser Gly Ile Thr Gly Ser Gly Gly Ser Thr Tyr Tyr Ala
 65              70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145             150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225             230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305             310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385             390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 3
```

-continued

```
<211> LENGTH: 728
<212> TYPE: DNA
<213> ORGANISM: Mus musculus

<400> SEQUENCE: 3
tctagaccac catggaaacc ccagcgcagc ttctcttcct cctgctactc tggctcccag      60
ataccaccgg agaaattgtg ttgacgcagt ctccaggcac cctgtctttg tctccagggg     120
aaagagccac cctctcctgt agggccagtc agagtgttcg cggcaggtac ttagcctggt     180
accagcagaa acctggccag gctcccaggc tcctcatcta tggtgcatcc agcagggcca     240
ctggcatccc agacaggttc agtggcagtg gtctgggaca gacttcact ctcaccatca      300 gcagactgga gcctgaagat tttgcagtgt tttactgtca gcagtatggt agttcacctc     360
ggacgttcgg ccaagggacc aaggtggaaa tcaaacgaac tgtggctgca ccatctgtct     420
tcatcttccc gccatctgat gagcagttga atctggaac tgcctctgtt gtgtgcctgc     480
tgaataactt ctatcccaga gaggccaaag tacagtggaa ggtggataac gccctccaat     540
cgggtaactc ccaggagagt gtcacagagc aggacagcaa ggacagcacc tacagcctca     600
gcagcaccct gacgctgagc aaagcagact acgagaaaca caagtctac gcctgcgaag     660 tcacccatca gggcctgagc tcgcccgtca caaagagctt caacagggga gagtgttgat     720
aagtcgac                                                              728

<210> SEQ ID NO 4
<211> LENGTH: 235
<212> TYPE: PRT
<213> ORGANISM: Mus musculus

<400> SEQUENCE: 4

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Arg Gly Arg Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
                100                 105                 110

Gly Ser Ser Pro Arg Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
```

```
                210               215               220
        Pro Val Thr Lys Ser Phe Asn Arg Gly Glu Cys
        225               230               235
```

<210> SEQ ID NO 5
<211> LENGTH: 25
<212> TYPE: DNA
<213> ORGANISM: Artificial Sequence
<220> FEATURE:
<223> OTHER INFORMATION: 5' kappa RACE primer

<400> SEQUENCE: 5
gatgacccag tctccagcca ccctg                                    25

<210> SEQ ID NO 6
<211> LENGTH: 23
<212> TYPE: DNA
<213> ORGANISM: Artificial Sequence
<220> FEATURE:
<223> OTHER INFORMATION: 3' kappa RACE primer

<400> SEQUENCE: 6
aagggtcaga ggccaaagga tgg                                      23

<210> SEQ ID NO 7
<211> LENGTH: 30
<212> TYPE: DNA
<213> ORGANISM: Artificial Sequence
<220> FEATURE:
<223> OTHER INFORMATION: 5' anti-OPGL-1 kappa primer

<400> SEQUENCE: 7
caactctaga ccaccatgga aaccccagcg                               30

<210> SEQ ID NO 8
<211> LENGTH: 37
<212> TYPE: DNA
<213> ORGANISM: Artificial Sequence
<220> FEATURE:
<223> OTHER INFORMATION: 3' anti-OPGL-1 kappa primer

<400> SEQUENCE: 8
tttgacgtcg acttatcaac actctcccct gttgaag                       37

<210> SEQ ID NO 9
<211> LENGTH: 23
<212> TYPE: DNA
<213> ORGANISM: Artificial Sequence
<220> FEATURE:
<223> OTHER INFORMATION: 5' IgG2 RACE primer

<400> SEQUENCE: 9
ggcacggtca ccacgctgct gag                                      23

<210> SEQ ID NO 10
<211> LENGTH: 24
<212> TYPE: DNA
<213> ORGANISM: Artificial Sequence
<220> FEATURE:
<223> OTHER INFORMATION: 3' IgG2 RACE primer

<400> SEQUENCE: 10
cctccaccaa gggcccatcg gtct                                     24

<210> SEQ ID NO 11
<211> LENGTH: 51

-continued

```
<210> SEQ ID NO 11
<211> LENGTH: 51
<212> TYPE: DNA
<213> ORGANISM: Artificial Sequence
<220> FEATURE:
<223> OTHER INFORMATION: 5' anti-OPGL-1 IgG2 Primer

<400> SEQUENCE: 11
cagaagcttg accaccatgg agtttgggct gagctggctt tttcttgtgg c          51

<210> SEQ ID NO 12
<211> LENGTH: 37
<212> TYPE: DNA
<213> ORGANISM: Artificial Sequence
<220> FEATURE:
<223> OTHER INFORMATION: 3' anti-OPGL-1 IgG2 Primer

<400> SEQUENCE: 12
gcatgtcgac ttatcattta cccggagaca gggagag                          37

<210> SEQ ID NO 13
<211> LENGTH: 122
<212> TYPE: PRT
<213> ORGANISM: Mus musculus

<400> SEQUENCE: 13
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
        115                 120

```
<210> SEQ ID NO 14
<211> LENGTH: 108
<212> TYPE: PRT
<213> ORGANISM: Mus musculus

<400> SEQUENCE: 14
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys

<210> SEQ ID NO 15
<211> LENGTH: 24
<212> TYPE: DNA
<213> ORGANISM: Artificial Sequence
<220> FEATURE:
<223> OTHER INFORMATION: random primer
<220> FEATURE:
<221> NAME/KEY: misc_feature
<222> LOCATION: (18)..(23)
<223> OTHER INFORMATION: N is A, C, G, or T

<400> SEQUENCE: 15
ggccggatag gcctcacnnn nnnt                                            24

<210> SEQ ID NO 16
<211> LENGTH: 5
<212> TYPE: PRT
<213> ORGANISM: Artificial Sequence
<220> FEATURE:
<223> OTHER INFORMATION: translation of portion of 5' anti-OPGL-1 kappa
      primer

<400> SEQUENCE: 16

Met Glu Thr Pro Ala
1               5

<210> SEQ ID NO 17
<211> LENGTH: 6
<212> TYPE: PRT
<213> ORGANISM: Artificial Sequence
<220> FEATURE:
<223> OTHER INFORMATION: translation of portion of 3' anti-OPGL-1 kappa
      primer

<400> SEQUENCE: 17

Cys Glu Gly Arg Asn Phe
1               5

<210> SEQ ID NO 18
<211> LENGTH: 12
<212> TYPE: PRT
<213> ORGANISM: Artificial Sequence
<220> FEATURE:
<223> OTHER INFORMATION: translation of portion of 5' anti-OPGL-1 IgG2
      Primer

<400> SEQUENCE: 18

Met Glu Phe Gly Leu Ser Trp Leu Phe Leu Val Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: translation of portion of 3' anti-OPGL-1 IgG2
      Primer

<400> SEQUENCE: 19

Lys Gly Pro Ser Leu Ser Leu
1               5

<210> SEQ ID NO 20
<211> LENGTH: 10
<212> TYPE: PRT
<213> ORGANISM: Artificial Sequence
<220> FEATURE:

```
<223> OTHER INFORMATION: LHRH antagonist peptide
<220> FEATURE:
<221> NAME/KEY: MISC_FEATURE
<222> LOCATION: (1)..(1)
<223> OTHER INFORMATION: Xaa is Ac-D-Nal, where Nal is
      3-(2-napthyl)alaninyl
<220> FEATURE:
<221> NAME/KEY: MISC_FEATURE
<222> LOCATION: (2)..(2)
<223> OTHER INFORMATION: Xaa is (4'-chlorophenul)alaninyl
<220> FEATURE:
<221> NAME/KEY: MISC_FEATURE
<222> LOCATION: (3)..(3)
<223> OTHER INFORMATION: Xaa is D-Pal, where Pal is
      3-(3'-pyridyl)alaninyl
<220> FEATURE:
<221> NAME/KEY: MISC_FEATURE
<222> LOCATION: (5)..(5)
<223> OTHER INFORMATION: Xaa is N-methyl tyrosine
<220> FEATURE:
<221> NAME/KEY: MISC_FEATURE
<222> LOCATION: (6)..(6)
<223> OTHER INFORMATION: Xaa is D-asparagine
<220> FEATURE:
<221> NAME/KEY: MISC_FEATURE
<222> LOCATION: (8)..(8)
<223> OTHER INFORMATION: Xaa is N-epsilon-2-propyl-lysinyl
<220> FEATURE:
<221> NAME/KEY: MISC_FEATURE
<222> LOCATION: (10)..(10)
<223> OTHER INFORMATION: Xaa is D-alanine-NH2

<400> SEQUENCE: 20

Xaa Xaa Xaa Ser Xaa Xaa Leu Xaa Pro Xaa
1               5                   10
```